(12) United States Patent
Grushka

(10) Patent No.: US 7,395,215 B2
(45) Date of Patent: Jul. 1, 2008

(54) PORTABLE PERSONAL HEALTH INFORMATION PACKAGE

(76) Inventor: Amos Grushka, 8 Hazaz Street, Herzlia (IL) 46404

( * ) Notice: Subject to any disclaimer, the term of this patent is extended or adjusted under 35 U.S.C. 154(b) by 470 days.

(21) Appl. No.: 10/290,301

(22) Filed: Nov. 8, 2002

(65) Prior Publication Data
US 2003/0088439 A1    May 8, 2003

Related U.S. Application Data

(60) Provisional application No. 60/331,098, filed on Nov. 8, 2001.

(51) Int. Cl.
G06Q 10/00 (2006.01)
(52) U.S. Cl. ............... 705/2; 705/3; 600/200
(58) Field of Classification Search ......... 600/300–301; 705/2–4
See application file for complete search history.

(56) References Cited

U.S. PATENT DOCUMENTS

| | | | |
|---|---|---|---|
| 3,921,318 A | 11/1975 | Calavetta | 40/626 |
| 3,958,690 A | 5/1976 | Gee, Sr. | 206/232 |
| 4,236,332 A | 12/1980 | Domo | 283/76 |
| 4,911,478 A | 3/1990 | Oshikoshi et al. | 283/109 |
| 5,143,405 A | 9/1992 | Daneshvar | 281/31 |
| 5,171,039 A | 12/1992 | Dusek | 283/75 |
| 5,197,763 A | 3/1993 | Whalen | 283/76 |
| 5,215,334 A | 6/1993 | Presson et al. | 283/76 |
| 5,337,290 A | 8/1994 | Ventimiglia et al. | 368/10 |
| 5,528,021 A * | 6/1996 | Lassus et al. | 235/380 |
| 5,659,741 A * | 8/1997 | Eberhardt | 707/104.1 |
| 5,887,742 A | 3/1999 | Lewis | 220/253 |
| 5,899,998 A * | 5/1999 | McGauley et al. | 707/104.1 |
| 5,924,074 A * | 7/1999 | Evans | 705/3 |
| 5,995,965 A | 11/1999 | Experton | 709/10 |
| 6,082,776 A * | 7/2000 | Feinberg | 283/72 |

(Continued)

OTHER PUBLICATIONS

"Graphic User Interface-Based Nuclear Medicine Reporting System" by Joseph J. Sanger; Journal of Nuclear Medicine, 1993; vol. 34, p. 515-522. (Retrieved from the Internet on Jan. 18, 2008 (URL: http://jnm.snmjounrls.org/cgi/reprint/34/3/515.pdf.*

(Continued)

Primary Examiner—Joseph Thomas
Assistant Examiner—Vivek Koppikar
(74) Attorney, Agent, or Firm—James Creighton Wray; Clifford D. Hyra

(57) ABSTRACT

A health information package that a person carries with him at all times with all his health data, and enables him to grant caregivers instant access to all or any part of his health data, whenever the information is needed, at all points of care anywhere in the world, in computer readable and eye readable forms. A database management software program is contained in a portable computer readable storage device of the package. A blank data recording form and an updated health overview, organized by body organ systems, problems, types and sub-types of data can be printed when desired. With the package, any standard personal computer can be used to record, update, link, integrate and display health data from birth to death. The owner has absolute control on the availability, completeness, accuracy, integrity, privacy, confidentiality, security, backups and access to his health data that are stored on the package.

69 Claims, 61 Drawing Sheets

U.S. PATENT DOCUMENTS

| | | | | |
|---|---|---|---|---|
| 6,140,936 | A | * | 10/2000 | Armstrong .................. 340/5.74 |
| 6,397,190 | B1 | * | 5/2002 | Goetz ............................ 705/3 |
| 6,523,009 | B1 | * | 2/2003 | Wilkins ......................... 705/3 |
| 6,611,846 | B1 | * | 8/2003 | Stoodley ................... 707/104.1 |
| 6,778,834 | B2 | * | 8/2004 | Laitinen et al. ............. 455/450 |
| 7,107,236 | B2 | * | 9/2006 | Lei ............................. 705/27 |
| 2002/0082868 | A1 | * | 6/2002 | Pories et al. .................... 705/3 |
| 2002/0194028 | A1 | * | 12/2002 | Johnston et al. ................ 705/3 |
| 2005/0039127 | A1 | * | 2/2005 | Davis ......................... 715/708 |
| 2005/0125256 | A1 | * | 6/2005 | Schoenberg et al. ........... 705/2 |

OTHER PUBLICATIONS

Grushka, Amos; *A.M.O.S. An all-purpose medical data and display system*; Proceedings of MIE-90; Aug. 20-23, 1990; Glasgow, Scotland; pp. 61-65.

Wallace, Simon; *Personalmedic—The portable electronic health record*; Proceedings of TEHRE 2000, Nov. 2000, London, England.

Martin, Stan; *Medical ID card*; Internet Worldwideweb entry, www.healthhistories.com; Jan. 13, 2002.

* cited by examiner

```
Volume in drive A is MILLER N
Volume label (11 characters, ENTER for none)?
Delete current volume label (Y/N)? n Insert SOURCE diskette in drive A:
Press any key to continue . . . .
Copying 80 tracks, 18 sectors per track, 2 side(s)
Reading from source diskette . . . .
Insert TARGET diskette in drive A:
Press any key to continue . . . .
Writing to target diskette . . . .
Do you wish to write another duplicate of this disk (Y/N)?
```

FIG 2

```
CURSOR    <-- -->         UP    DOWN           DELETE              Insert Mode:  Ins
Char:      ^   ^   Record:                     Char:      Del      Exit:        ^End
Field: Home End    Page:   PgUp  PgDn          Field:      ^Y      Abort:        Esc
Pan:       ^   ^   Help:   F1                  Record:     ^U      Set Options: ^Home
```

```
SYS NO T DATA-------------------------- DETAILS------- SQ SUB DATE------
 34 /31  Miller Nancy                   Atlanta, GA. USA      DOB Aug12,1936
???  1  s syncope                                      1  ana 24.09.1963
???  1  s syncope                          37          2  ana 18.02.1966
???  2  s cough, non productive                           ana 1968,69,70
???  3  s vertigo                        severe           ana 02-08-1983
???  4  s frontal hard mass, left                         pex 08.08.1983
???  5  l high SAP (serum alk. phosphatase)  5-6mm        bid 28-08-1984
cvs  1  d varicose veins, legs           100/85           pex 17.04.1978
cvs  2  d thrombophlebitis, leg, lt.     Lt. > Rt.        pex +- 06/1982
cvs  2  d thrombophlebitis, left calf                     pex 03.02.1986
cvs  3  d hypertension, fluctuating                       cln since 1972
      ↖32                                   ↙35  ↙23                  ↙41
         ↖33
```

FIG. 3

```
CURSOR    <-- -->         UP    DOWN           DELETE              Insert Mode:  Ins
Char:      ^   ^   Record:                     Char:      Del      Exit:        ^End
Field: Home End    Page:   PgUp  PgDn          Field:      ^Y      Abort:        Esc
Pan:       ^   ^   Help:   F1                  Record:     ^U      Set Options: ^Home
```

FIG. 3a

| SYS | NO | T | DATA | DETAILS | SQ | SUB DATE |
|---|---|---|---|---|---|---|
| | | | Miller Nancy  42 | Atlanta, GA. USA | | DOB Aug12,1936 |
| ??? | 1 | s | syncope | | 1 | ana 24.09.1963 |
| ??? | 1 | s | syncope | | 2 | ana 18.02.1966 |
| ??? | 2 | s | cough, non productive | severe | | ana 1968,69,70 |
| ??? | 3 | s | vertigo | | | ana 02-08-1983 |
| ??? | 4 | s | frontal hard mass, left | | | pex 08.08.1983 |
| ??? | 5 | l | high SAP (serum alk. phosphatase) | | | bld 28-08-1984 |
| cvs | 1 | d | varicose veins, legs | 5-6mm | | pex 17.04.1978 |
| cvs | 2 | d | thrombophlebitis, leg, lt. | 100/85 | | pex +- 06/1982 |
| cvs | 2 | d | thrombophlebitis, left calf | Lt. > Rt. | | pex 03.02.1986 |
| cvs | 3 | d | hypertension, fluctuating | | | cln since 1972 |
| cvs | 3 | f | hypertension | mother | | ana at age 30 |
| cvs | 3 | f | hypertension ⟵ 29 | sister | | ana at age 25 |
| cvs | 3 | l | hypertension | 150/110 | | pex 07.12.1977 |
| cvs | 3 | l | cardiomegaly | isotope scan | | iso 29.04.1980 |
| cvs | 3 | S | HYPERTENSIVE RETINOPATHY | GRADE 1 | | pex 13.06.1964 |
| cvs | 3 | T | DIGOXIN | 0,25mgx1 qd | | tab 1965->1966 |

| Bottom | Top | Lock | Record No. | Freeze | Find 03:00:48 pm |
|---|---|---|---|---|---|
| SYS NO T | DATA | | | DETAILS | SQ SUB DATE |
| | 44 Miller Nancy | | 43 | Atlanta, GA. USA | DOB Aug12,1936 |
| ??? 1 s | syncope | | | | 1 ana 24.09.1963 |
| ??? 1 s | syncope | | | | 2 ana 18.02.1966 |
| ??? 2 s | cough, non productive | | | severe | ana 1968,69,70 |
| ??? 3 s | vertigo | | | | ana 02-08-1983 |
| ??? 4 s | frontal hard mass, left | | | | pex 08.08.1983 |
| ??? 5 l | high SAP (serum alk. phosphatase) | | | 5-6mm | bld 28-08-1984 |
| cvs 1 d | varicose veins, legs | | | 100/85 | pex 17.04.1978 |
| cvs 2 d | thrombophlebitis, leg, lt. | | | Lt. > Rt. | pex +- 06/1982 |
| cvs 2 d | thrombophlebitis, left calf | | | | pex 03.02.1986 |
| cvs 3 d | hypertension, fluctuating | | 29 | | cln since 1972 |
| cvs 3 f | hypertension | | | mother | ana at age 30 |
| cvs 3 f | hypertension | | | sister | ana at age 25 |
| cvs 3 l | hypertension | | | 150/110 | pex 07.12.1977 |
| cvs 3 l | cardiomegaly | | | isotope scan | iso 29.04.1980 |
| cvs 3 S | HYPERTENSIVE RETINOPATHY | | 23 | GRADE 1 | pex 13.06.1964 |
| cvs 3 T | DIGOXIN | | | 0,25mgx1 qd | tab 1965->1966 |

FIG 5

| Bottom | | | Top | Lock | Record No. | Freeze | Find 03:05:56 pm |
|---|---|---|---|---|---|---|---|
| SYS | NO | T | DATA | | DETAILS | | SQ SUB DATE |
| mus | 6 | D | TENNIS ELBOW, RT. | | | | cln 18.08.1983 |
| mus | 7 | D | TENNIS ELBOW, LEFT | | | | cln 26.09.1985 |
| mus | 8 | T | REPAIR OF POST OP. ABDOM. HERNIA | | | | sur 02.06.1986 |
| psy | 1 | d | schizophrenia, acute episode | hospitalized | | | cln 07.03.1976 |
| psy | 1 | d | psychotic episode | hospitalized | | | cln 07.06.1964 |
| psy | 1 | d | schizophrenia, acute event | hospitalized | | | cln 14.06.1986 |
| psy | 1 | d | schizophrenia, paranoid | | | | cln 2-4/1964 |
| psy | 1 | f | schizophrenia | father | | | ana at age 55 |
| psy | 1 | t | halidol | | | | tab Start 1987 |
| psy | 1 | t | phenergan | | | | tab Start 1987 |
| res | 1 | d | chornic obstructive lung disease | | | | cln 08.06.1983 |
| res | 1 | l | obstructive lung disease | pul. funct. tests | | | pft 08.06.1983 |
| res | 1 | s | heavy smoker | 80-100 cig. qd | | 1 | ana from age13 |
| res | 1 | s | EXERTIONAL DYSPNEA | | | 2 | ana since 1977 |
| res | 1 | t | ventolin | inhalation | | | inh 1983 (May) |
| skn | 1 | d | urticaria after anti-tetanus | | | | cln 25.09.1963 |
| skn | 2 | d | urticaria after toxoid | | | | cln 02.11.1970 |
| skn | 3 | d | drug eruptions (sulpha and iodine) | | | | cln August1977 |
| skn | 4 | d | erysipelas cruris, right | | | | cln 27.03.1977 |
| skn | 4 | d | erysipelas, Lt. leg, recc. | x5 | | | cln 1978-1983 |

FIG 6

Bottom    Top------    43  Lock  46 Record No.      Freeze      Find   05:52:39 pm
SYS NO T DATA------    Change number of columns to lock to: 5              DATE------
        Miller Nancy                                                       Aug12,1936
??? 1 s syncope                                             48  2    ana   24.09.1963
??? 1 s syncope                                      45              ana   18.02.1966
??? 2 s cough, non productive         severe                         ana   1968,69,70
??? 3 s vertigo                                                      ana   02-08-1983
??? 4 s frontal hard mass, left                                      pex   08.08.1983
??? 5 l high SAP (serum alk. phosphatase)                            bid   28-08-1984
cvs 1 d varicose veins, legs          5-6mm                          pex   17.04.1978
cvs 2 d thrombophlebitis, leg, lt.    100/85                         pex + - 06/1982
cvs 2 d thrombophlebitis, left calf   Lt. > Rt.                      pex   03.02.1986
cvs 3 d hypertension, fluctuating                                    cln since 1972
cvs 3 f hypertension                  mother                         ana at age 30
cvs 3 f hypertension                  sister                         ana at age 25
cvs 3 l hypertension                  150/110                        pex   07.12.1977
cvs 3 l cardiomegaly                  isotope scan                   iso   29.04.1980
cvs 3 S HYPERTENSIVE RETINOPATHY      GRADE 1            23          pex   13.06.1964
cvs 3 T DIGOXIN                       0,25mgx1 qd                    tab   1965->1966

FIG 7

| SYS | NO | T | DATA | DETAILS | SOURCE |
|---|---|---|---|---|---|
| ??? | | | Miller Nancy | Atlanta, GA. USA | patient |
| ??? | 1 | s | syncope | | husband |
| ??? | 1 | s | syncope | | husband |
| ??? | 2 | s | cough, non productive | severe | patient |
| ??? | 3 | s | vertigo | | patient |
| ??? | 4 | s | frontal hard mass, left | 5-6mm | MD Johnson |
| ??? | 5 | l | high SAP (serum alk. phosphatase) | | report (chem.) |
| cvs | 1 | d | varicose veins, legs | 100/85 | MD Smith |
| cvs | 2 | d | thrombophlebitis, leg, lt. | Lt. > Rt. | MD Smith |
| cvs | 2 | d | thrombophlebitis, left calf | | MD Smith |
| cvs | 3 | d | hypertension, fluctuating ← 29 | | record (clinic) |
| cvs | 3 | f | hypertension | mother | patient |
| cvs | 3 | f | hypertension | sister | patient |
| cvs | 3 | l | hypertension | 150/110 | RN Gilbert |
| cvs | 3 | l | cardiomegaly | isotope scan | report (iso) |
| cvs | 3 | S | HYPERTENSIVE RETINOPATHY | GRADE 1 | MD Ophthatmol. |
| cvs | 3 | T | DIGOXIN | 0,25mgx1 qd | record (clinic) |

| SYS | NO | T | DATA | SUB | DATE | TIME |
|---|---|---|---|---|---|---|
| | | | Miller Nancy | DOB | Aug12,1936 | |
| ??? | 1 | s | syncope | ana | 24.09.1963 | morning |
| ??? | 1 | s | syncope | ana | 18.02.1966 | evening |
| ??? | 2 | s | cough, non productive | ana | 1968,69,70 | in summers |
| ??? | 3 | s | vertigo | ana | 02-08-1983 | whole day |
| ??? | 4 | s | frontal hard mass, left | pex | 08.08.1983 | |
| ??? | 5 | l | high SAP (serum alk. phosphatase) | bld | 28-08-1984 | |
| cvs | 1 | d | varicose veins, legs | pex | 17.04.1978 | |
| cvs | 2 | d | thrombophlebitis, leg, lt. | pex | +- 06/1982 | |
| cvs | 2 | d | thrombophlebitis, left calf | pex | 03.02.1986 | -14.02.1986 |
| cvs | 3 | d | hypertension, fluctuating | cln | since 1972 | |
| cvs | 3 | f | hypertension | ana | at age 30 | |
| cvs | 3 | f | hypertension | ana | at age 25 | |
| cvs | 3 | l | hypertension | pex | 07.12.1977 | 08:30 AM |
| cvs | 3 | l | cardiomegaly | iso | 29.04.1980 | |
| cvs | 3 | S | HYPERTENSIVE RETINOPATHY | pex | 13.06.1964 | |
| cvs | 3 | T | DIGOXIN | tab | 1965->1966 | |

FIG 9

```
Bottom      Top      Lock         Record No.   54 Freeze    Find  06:14:37 pm
SYS NO T DATA------------------------------------------------------    TE-------
       T    Miller Nancy               Enter new record number: 19      g12,1936
??? 1  s    syncope                                          /          .09.1963
                                                            56  2
??? 1  s    syncope                                                ana 18.02.1966
??? 2  s    cough, non productive              severe      53     ana 1968,69,70
??? 3  s    vertigo                                                ana 02-08-1983
??? 4  s    frontal hard mass, left                                pex 08.08.1983
??? 5  l    high SAP (serum alk. phosphatase)   5-6mm              bld 28-08-1984
cvs 1  d    varicose veins, legs                100/85             pex 17.04.1978
cvs 2  d    thrombophlebitis, leg, lt.          Lt. > Rt.          pex +- 06/1982
cvs 2  d    thrombophlebitis, left calf                            pex 03.02.1986
cvs 3  d    hypertension, fluctuating                              cln since 1972
cvs 3  f    hypertension                        mother             ana at age 30
cvs 3  f    hypertension                        sister             ana at age 25
cvs 3  l    hypertension                        150/110            pex 07.12.1977
cvs 3  l    cardiomegaly                        isotope scan       iso 29.04.1980
cvs 3  S    HYPERTENSIVE RETINOPATHY            GRADE 1            pex 13.06.1964
cvs 3  T    DIGOXIN                             0,25mgx1 qd        tab 1965->1966
```

| SYS | NO | T | DATA | DETAILS | SQ | SUB | DATE |
|---|---|---|---|---|---|---|---|
| gur | 2 | 1 | small right kidney | in ultrasound | 1 | usd | 29.04.1980 |
| gur | 2 | 1 | no visualization, right kidney | isotope scanning | 2 | iso | 28.07.1980 |
| gyn | 1 | d | menopause | | | ana | at age 43 |
| gyn | 2 | d | endometrial glandular hyperplasia | | | cln | 06.03.1978 |
| gyn | 2 | 1 | uterine curretage | | | sur | 06.03.1978 |
| gyn | 2 | 1 | uterine curretage | | | sur | 28.03.1979 |
| gyn | 2 | 1 | uterine curretage | for PMB | | sur | 10.12.1980 |
| gyn | 2 | 1 | uterine curretage | | | sur | 30.01.1982 |
| gyn | 2 | 1 | uterine curretage | for PMB | | sur | 14.05.1985 |
| gyn | 2 | 1 | atypical glandular hyperplasia | | 1 | his | 28.03.1979 |
| gyn | 2 | s | post-menopausal bleeding | at the age of 48 | | ana | 01.03.1978 |
| gyn | 2 | s | meno-metrorrhagia | | | ana | 24.03.1971 |
| gyn | 2 | s | vaginal bleeding | | | ana | 27.08.1981 |
| gyn | 2 | s | post menopausal bleeding | | | ana | 03.02.1983 |
| gyn | 2 | s | post menopausal bleeding | | | ana | 10.05.1985 |
| gyn | 3 | 1 | trichomonas vaginalis | vaginal smear | | bct | 27.10.1983 |
| heb | 1 | 1 | hepatomegaly | isotope scan | | iso | 23.07.1980 |

FIG 11

```
Bottom      Top     Lock        Record No.                      Freeze  59  Find  03:33:34 pm
SYS  NO  T  DATA----------------------------  Enter field name to freeze:  DATE           --
???   1  s  Miller Nancy                                                                   36
???   1  s  syncope                                                         2  ana 18.02.1966  63
???   2  s  syncope                                                            ana 1968,69,70
???   2  s  cough, non productive              severe                           ana 02-08-1983
???   3  s  vertigo                                                             pex 08.08.1983
???   4  s  frontal hard mass, left            5-6mm                            bld 28-08-1984
???   5  l  high SAP (serum alk. phosphatase)                                   pex 17.04.1978
cvs   1  d  varicose veins, legs               Lt. > Rt.                        pex +- 06/1982
cvs   2  d  thrombophlebitis, leg, lt.                          29              pex 03.02.1986
cvs   2  d  thrombophlebitis, left calf                                         cln since 1972
cvs   3  d  hypertension, fluctuating                                           ana at age 30
cvs   3  f  hypertension                       mother                           ana at age 25
cvs   3  f  hypertension                       sister                           pex 07.12.1977
cvs   3  l  hypertension                       150/110                          iso 29.04.1980
cvs   3  l  cardiomegaly                       isotope scan                     pex 13.06.1964
cvs   3  S  HYPERTENSIVE RETINOPATHY           GRADE 1                          tab 1965->1966
cvs   3  T  DIGOXIN                            0,25mgx1 qd
```

```
Bottom      Top      Lock       Record No.     Freeze   [MET]  Find   06:30:46 pm
SYS NO T DATA------------------------- Enter search string: [MET]            -- --
         Miller Nancy                                                        36
??? 1  s syncope                                                             63
??? 1  s syncope                                          2    ana 18.02.1966
??? 2  s cough, non productive       severe                    ana 1968,69,70
??? 3  s vertigo                                               ana 02-08-1983
??? 4  s frontal hard mass, left                                pex 08.08.1983
??? 5  l high SAP (serum alk. phosphatase)  5-6mm              bid 28-08-1984
cvs 1  d varicose veins, legs                                  pex 17.04.1978
cvs 2  d thrombophlebitis, leg, lt.  100/85                    pex +- 06/1982
cvs 2  d thrombophlebitis, left calf  Lt. > Rt.                pex 03.02.1986
cvs 3  d hypertension, fluctuating                             cln since 1972
cvs 3  f hypertension                mother                    ana at age 30
cvs 3  f hypertension                sister                    ana at age 25
cvs 3  l hypertension                150/110                   pex 07.12.1977
cvs 3  l cardiomegaly                isotope scan              iso 29.04.1980
cvs 3  S HYPERTENSIVE RETINOPATHY    GRADE 1                   pex 13.06.1964
cvs 3  T DIGOXIN                     0,25mgx1 qd               tab 1965->1966
```

FIG 13

| SYS | NO | T | DATA | DETAILS | SQ | SUB | DATE |
|---|---|---|---|---|---|---|---|
| met | 1 | d | obesity, severe | | | cln | since 1947 |
| met | 1 | l | overweight, severe | 136 kg | | pex | 17.05.1965 |
| met | 1 | l | overweight, severe | 143 kg | | pex | 17.04.1978 |
| met | 1 | l | overweight, severe | 161 kg | | pex | 26.10.1983 |
| met | 1 | t | gastric bypass + gastrostomy | for overweight+++ | | sur | 20.12.1983 |
| met | 2 | l | hyperuricemia | 9.5 mg% | | bld | 12.08.1982 |
| met | 2 | l | hyperuricemia | 9.4 mg% | | bld | 17.12.1982 |
| met | 2 | l | hyperuricemia | 7.6-8.9 mg% | | bld | 01-02/1983 |
| met | 2 | l | hyperuricosuria | 600 mg/24h | 1 | urn | 18.03.1983 |
| met | 2 | t | allopurinol | 100mgx2 | | tab | since 4/83 |
| mus | 1 | L | BI-MALEOLAR FRACTURE, ANKLE, RT. | | | xrs | 21.05.1965 |
| mus | 1 | T | OPEN REDUCTION OF FRACTURE | | | sur | 24.05.1965 |
| mus | 2 | d | arthritis, rheumatoid | | | cln | 21.01.1966 |
| mus | 2 | s | painfull swelling of joints | | | ana | since 1963 |
| mus | 3 | d | discopathy | L4-L5 | | cln | since 1971 |
| mus | 3 | l | osteophyte, L5 | isotope scan | | iso | 28.07.1980 |
| mus | 3 | l | herniation of lumbar discus | L4-L5 | | xrs | 04.06.1971 |

FIG 14

```
mus 1   L  BI-MALEOLAR FRACTURE, ANKLE, RT.          xrs  21.05.1965
mus 1   T  OPEN REDUCTION OF FRACTURE                sur  24.05.1965
mus 2   d  arthritis, rheumatoid                     cln  21.01.1964
mus 2   s  painfull swelling of joints               ana  since 1963
mus 3   d  discopathy                                cln  since 1971
mus 3   l  herniation of lumbar discus            1  xrs  04.06.1971
mus 3   l  osteophyte, L5                         2  iso  28.07.1980
mus 3   s  LBP                                       ana  Since 2/71
mus 4   s  shoulder pain                             ana  01.01.1981  -17.01.1981
mus 4   T  VOLTAREN                                  tab  January/81
mus 5   L  DEG. CHANGES, CERVICAL VERTEBRAE          xrs  00.02.1983
mus 5   s  cervical pain                             ana  18.01.1983  -23.01.1983
mus 5   S  CERVICAL PAIN                             ana  28.06.1984  -12.07.1984
mus 6   D  TENNIS ELBOW, RT.                         cln  18.08.1983
mus 7   D  TENNIS ELBOW, LEFT                        cln  26.09.1985
mus 8   T  REPAIR OF POST OP. ABDOM. HERNIA          sur  02.06.1986
```

```
skn 1  d urticaria after anti-tetanus          cln 25.09.1963
skn 2  d urticaria after toxoid                cln 02.11.1970
skn 3  d drug eruptions (sulpha and iodine)    cln August1977
skn 4  d erysipelas cruris, right              cln 27.03.1977
skn 4  d erysipelas, Lt. leg, recc.            cln 1978-1983
```
↖ 79

```
mother   ana at age 30
sister   ana at age 25
father   ana at age 55
```
← 83

```
cvs 3  f hypertension
cvs 3  f hypertension
psy 1  f schizophrenia
```
← 84

FIG 19

| | | | | |
|---|---|---|---|---|
| ??? | 1 | s | syncope | | ana 24.09.1963 |
| ??? | 1 | s | syncope | | ana 18.02.1966 |
| ??? | 2 | s | cough, non productive | severe | ana 1968,69,70 |
| ??? | 3 | s | vertigo | | ana 02-08-1983 |
| ??? | 4 | s | frontal hard mass, left | 5-6mm | pex 08.08.1983 |
| cvs | 3 | S | HYPERTENSIVE RETINOPATHY | GRADE 1 | pex 13.06.1964 |
| cvs | 4 | s | systolic murmur | grade 2/6 | pex 23.12.1982 |
| cvs | 5 | s | aortic insufficiency | | pex 04.08.1985 |
| cvs | 6 | s | chest pain | after effort | ana 31.07.1963 |
| cvs | 6 | s | chest pain | retro-sternal | ana 01.01.1981 |
| cvs | 6 | s | chest pain | rad. Lt. shoulder | ana 02.03.1983 |
| cvs | 6 | s | chest pain | like pressure | ana 16.06.1983 |
| gyn | 2 | s | post-menopausal bleeding | | ana at age 48 |
| gyn | 2 | s | meno-metrorrhagia | | ana 24.03.1971 |
| gyn | 2 | s | vaginal bleeding | | ana 27.08.1981 |
| gyn | 2 | s | post menopausal bleeding | | ana 03.02.1983 |
| gyn | 2 | s | post menopausal bleeding | | ana 10.05.1985 |
| mus | 2 | s | painfull swelling of joints | | ana since 1963 |
| mus | 3 | s | LBP | | ana Since 2/71 |

Press any key to continue...

FIG 20

| | | | | | |
|---|---|---|---|---|---|
| ??? | 5 | 1 | high SAP (serum alk. phosphatase) | 100/85 | bld 28-08-1984 |
| cvs | 3 | 1 | hypertension | 150/110 | pex 07.12.1977 |
| cvs | 3 | 1 | cardiomegaly | isotope scan | iso 29.04.1980 |
| cvs | 5 | 1 | aortic insufficiency | echo-cardiogram | eco 22.01.1986 |
| ent | 1 | 1 | high ASLO | 350 | bld 28.06.1961 |
| git | 2 | 1 | narrow gastro-jejun. anastomosis | post op. | xrs 20.09.1984 |
| gur | 2 | 1 | small right kidney | in ultrasound | usd 29.04.1980 |
| gur | 2 | 1 | no visualization, right kidney | isotope scanning | iso 28.07.1980 |
| gyn | 2 | 1 | uterine curretage | | sur 06.03.1978 |
| gyn | 2 | 1 | uterine curretage | | sur 28.03.1979 |
| gyn | 2 | 1 | uterine curretage | | sur 10.12.1980 |
| gyn | 2 | 1 | uterine curretage | | sur 30.01.1982 |
| gyn | 2 | 1 | uterine curretage | for PMB | sur 14.05.1985 |
| gyn | 2 | 1 | atypical glandular hyperplasia | | his 28.03.1979 |
| gyn | 3 | 1 | trichomonas vaginalis | vaginal smear | bct 27.10.1983 |
| heb | 1 | 1 | hepatomegaly | isotope scan | iso 23.07.1980 |
| heb | 2 | 1 | septum in gallbladder | in ultrasound | usd 14.06.1985 |
| met | 1 | 1 | overweight, severe | 136 kg | pex 17.05.1965 |
| met | 1 | 1 | overweight, severe | 143 kg | pex 17.04.1978 |

Press any key to continue... ~88

```
cvs 1  d varicose veins, legs                         Lt. > Rt.        pex 17.04.1978
cvs 2  d thrombophlebitis, leg, lt.                                    pex +- 06/1982
cvs 2  d thrombophlebitis, left calf                                   pex 03.02.1986
cvs 3  d hypertension, fluctuating                                     cln since 1972
ent 1  d follicular tonsillitis                                        pex 22.6.61-->
gur 1  d urinary tract infections (x3)                                 urn 1-7/1962
gur 1  d urinary tract infection                                       urn 25.12.1962
gur 1  d urinary tract infection         B. proteus                    urn 31.05.1964
gur 1  d urinary tract infection         E.coli                        urn ?June 1966
gur 1  d urinary tract infection         Pseudomonas                   urn 27.08.1984
gyn 1  d menopause                                                     ana at age 43
gyn 2  d endometrial glandular hyperplasia                             cln 06.03.1978
met 1  d obesity, severe                                               cln since 1947
mus 2  d arthritis, rheumatoid                                         cln 21.01.1964
mus 3  d discopathy                      L4-L5                         cln since 1971
mus 6  D TENNIS ELBOW, RT.                                             cln 18.08.1983
mus 7  D TENNIS ELBOW, LEFT                                            cln 26.09.1985
psy 1  d schizophrenia, acute episode                                  cln 07.03.1976
psy 1  d psychotic episode                                             cln 07.06.1964
Press any key to continue...
```

FIG 22

```
cvs  3  T  DIGOXIN                           0,25mgx1 qd           tab 1965->1966
cvs  3  T  FUSID                             40mg qod              tab 1965->1966
cvs  6  T  ADALAT                            10mgx3 qd             tab since 1981
git  1  t  appendectomy                                            sur 4June 1946
git  2  t  re-gastro-enterostomy             bypass stenosis       sur end of 84
met  1  t  gastric bypass + gastrostomy      for overweight+++     sur 20.12.1983
met  2  t  allopurinol                       100mgx2               tab since 4/83
mus  1  T  OPEN REDUCTION OF FRACTURE                              sur 24.05.1965
mus  4  T  VOLTAREN                          50mgx3                tab January/81
mus  8  T  REPAIR OF POST OP. ABDOM. HERNIA                        sur 02.06.1986
psy  1  t  halidol                                                 tab Start 1987
psy  1  t  phenergan                                               tab Start 1987
res  1  t  ventolin                          inhalation            inh 1983 (May)
```

FIG 23

```
cvs 3   T DIGOXIN       0.25mgx1 qd    tab 1965->1966
cvs 3   T FUSID         40mg qod       tab 1965->1966
cvs 6   T ADALAT        10mgx3 qd      tab since 1981
met 2   t allopurinol   100mgx2        tab since 4/83
mus 4   T VOLTAREN      50mgx3         tab January/81
psy 1   t halidol                      tab Start 1987
psy 1   t phenergan                    tab Start 1987
                                            ↖ 94
```

```
???  5  1 high SAP (serum alk. phosphatase)  100/85         bld 28-08-1984
ent  1  1 high ASLO                          350            bld 28.06.1961
met  2  1 hyperuricemia                      9.5 mg%        bld 12.08.1982
met  2  1 hyperuricemia                      9.4 mg%        bld 17.12.1982
met  2  1 hyperuricemia                      7.6-8.9 mg%    bld 01-02/1983
```

SEARCH ON WHAT FIELD? SUB —96
LOOK FOR WHAT SUB? XRS
97a ↙    ↘98
← 97

SEARCH ON WHAT FIELD?
LOOK FOR WHAT ?
97a ↙
← 97

```
git 2  1 narrow gastro-jejun. anastomosis   post op.                xrs 20.09.1984
mus 1  L BI-MALEOLAR FRACTURE, ANKLE, RT.                           xrs 21.05.1965
mus 3  1 herniation of lumbar discus        L4-L5                   xrs 04.06.1971
mus 5  L DEG. CHANGES, CERVICAL VERTEBRAE                           xrs 00.02.1983
```
← 100    ← 98

SEARCH ON WHAT FIELD? SUB — 103
LOOK FOR WHAT SUB? PEX — 105

```
??? 4   s frontal hard mass, left                              pex 08.08.1983
cvs 1   d varicose veins, legs                                 pex 17.04.1978
cvs 2   d thrombophlebitis, leg, lt.        5-6mm              pex +- 06/1982
cvs 2   d thrombophlebitis, left calf       Lt. > Rt.          pex 03.02.1986
cvs 3   l hypertension                      150/110            pex 07.12.1977
cvs 3   S HYPERTENSIVE RETINOPATHY          GRADE 1            pex 13.06.1964
cvs 4   s systolic murmur                   grade 2/6          pex 23.12.1982
cvs 5   s aortic insufficiency                                 pex 04.08.1985
ent 1   d follicular tonsillitis                               pex 22.6.61-->
met 1   l overweight, severe                136 kg             pex 17.05.1965
met 1   l overweight, severe                143 kg             pex 17.04.1978
met 1   l overweight, severe                161 kg             pex 26.10.1983
     ↙100                                        ↙105                ↙107
```

FIG 29

SEARCH ON WHAT FIELD? DATA —— 111
LOOK FOR WHAT DATA? CHEST PAIN }— 113

```
after effort      ana 31.07.1963
retro-sternal     ana 01.01.1981
rad. Lt. shoulder ana 02.03.1983
like pressure     ana 16.06.1983
```

← 115

```
cvs 6 s chest pain
cvs 6 s chest pain
cvs 6 s chest pain
cvs 6 s chest pain
```

SYS — 129
NO — 128
T
DATA
DETAILS
SQ
SUB
DATE
TIME
SOURCE

131

```
SYS NO T DATA------------------------------  DETAILS-------  SQ SUB DATE-------
psy 1 d schizophrenia, acute episode         hospitalized       cln 07.03.1976
psy 1 d psychotic episode                    hospitalized       cln 07.06.1964
psy 1 d schizophrenia, acute event           hospitalized       cln 14.06.1986
psy 1 d schizophrenia, paranoid                                 cln 2-4/1964
psy 1 f schizophrenia                        father             ana at age 55
psy 1 t halidol                                                 tab Start 1987
psy 1 t phenergan                                               tab Start 1987
res 1 d chornic obstructive lung disease                        cln 08.06.1983
res 1 l obstructive lung disease             pul. funct. tests  pft 08.06.1983
res 1 s heavy smoker                         80-100 cig. qd   1 ana from age13
res 1 s EXERTIONAL DYSPNEA                                    2 ana since 1977
res 1 t ventolin                             inhalation         inh 1983 (May)
skn 1 d urticaria after anti-tetanus                            cln 25.09.1963
skn 2 d urticaria after toxoid                                  cln 02.11.1970
skn 3 d drug eruptions (sulpha and iodine)                      cln August1977
skn 4 d erysipelas cruris, right                                cln 27.03.1977
skn 4 d erysipelas, Lt. leg, recc.           x5                 cln 1978-1983

===> Add new records? (Y/N) 137        133

FIG 34
```

| SYS | NO | T | DATA | DETAILS | SQ | SUB | DATE |
|-----|----|----|------|---------|----|----|------|
| psy | 1 | d | psychotic episode | hospitalized | | cln | 07.06.1964 |
| psy | 1 | d | schizophrenia, acute event | hospitalized | | cln | 14.06.1986 |
| psy | 1 | d | schizophrenia, paranoid | | | cln | 2-4/1964 |
| psy | 1 | f | schizophrenia | father | | ana | at age 55 |
| psy | 1 | t | halidol | | | tab | Start 1987 |
| psy | 1 | t | phenergan | | | tab | Start 1987 |
| res | 1 | d | chornic obstructive lung disease | | | cln | 08.06.1983 |
| res | 1 | l | obstructive lung disease | pul. funct. tests | | pft | 08.06.1983 |
| res | 1 | s | heavy smoker | 80-100 cig. qd | 1 | ana | from age13 |
| res | 1 | s | EXERTIONAL DYSPNEA | | 2 | ana | since 1977 |
| res | 1 | t | ventolin | inhalation | | inh | 1983 (May) |
| skn | 1 | d | urticaria after anti-tetanus | | | cln | 25.09.1963 |
| skn | 2 | d | urticaria after toxoid | | | cln | 02.11.1970 |
| skn | 3 | d | drug eruptions (sulpha and iodine) | | | cln | August1977 |
| skn | 4 | d | erysipelas cruris, right | | | cln | 27.03.1977 |
| skn | 4 | d | erysipelas, Lt. leg, recc. | x5 | | cln | 1978-1983 |

FIG 35

```
SYS NO T DATA------------------- SQ SUB DATE------ TIME------
 1  1 d URTI                         cln
 1  1 s cough                      1 sym       07:00
 1  1 s myalgia      ← 29          2 sym       14:00
 1  1 s hoarsness                  3 sym       18:30
 1  1 s running nose               4 sym       19:30
 1  1 s sore throat                5 sym       19:30
 1  1 s coldness sensation         6 sym       20:35
 1  1 t Robitussin                   syr      >26.12.2000
```

FIG 36b

REPLACE WHAT FIELD? SYS
REPLACE WITH WHAT SYS? RES
ARE YOU SURE (Y/N)

FIG 36c

REPLACE WHAT FIELD? DATE
REPLACE WITH WHAT DATE? 13.02.2002
ARE YOU SURE (Y/N)

```
SYS NO T DATA------------------        SQ SUB DATE-------  TIME-------
RES  1 d URTI                           1 cln 13.02.2002  07:00
RES  1 s cough                          2 sym 13.02.2002  14:00
RES  1 s myalgia                        3 sym 13.02.2002  18:30
RES  1 s hoarsness        ⟵ 29          4 sym 13.02.2002  19:30
RES  1 s running nose                   5 sym 13.02.2002  19:30
RES  1 s sore throat                    6 sym 13.02.2002  20:35
RES  1 s coldness sensation               syr 13.02.2002 >26.02.2002
RES  1 t Robitussin
```

FIG 36d

```
      PORTABLE HEALTH INFORMATION PACKAGE

HEALTH VIEW

** ==========================================
*  Smith Robert      167        data: 1995-2000         DOB 12.JAN.35
** ================\→cvs======================
   169
*  ↙  1
d  myocardial infarction       anteroseptal             cln 25.02.1995
l  anteroseptal MI, acute      QS in V1-V4              ecg 25.02.1995
l  narrow coronaries (LAD, RC, CIR)  100% 99% 70%       ang 03.03.1995
s  chest pain, severe          on effort                ana 24.02.1995
t  coronary artery bypass graft  x3 coronaries          sur 06.03.1995

** ==================================== git
*    1
d  duodenal ulcer              by endoscopy             cln 15.12.1998
l  duodenal ulcer                                       end 15.12.1998
s  heartburn                   before meals             ana since 7/98
t  omeprazole (Losec)          20 mg qd                 cap 16.12.1998

** ==================================== res
*    1
d  upper respiratory tract infection                    cln 22.11.2000
t  robitussin syrup            1 tablespoon q3h         syr 23.11.2000

```
              PORTABLE HEALTH INFORMATION PACKAGE

HEALTH VIEW

**  =================================================

*   Smith Robert        167   data: 1-6/2001        DOB 12.JAN.35

**  ============================================ cvs

*    . 1
t   aspirin                   100 mg x1 qd          tab 02.05.2001

**  ============================================ eye

*  169  . 1
d   glaucoma                  bilateral             cln 24.02.2001
1   increased intraocular pressure  46 mm Hg (bilat.)  pex 24.02.2001
s   blurred vision                                  ana 1/2001-->>

**  ============================================ git

*    . 2
d   bleeding duodenal ulcer   after aspirin         cln 12.06.2001
1   anemia                    9,1 g%                bld 10.06.2001
1   positive occult blood in stool  +++             stl 10.06.2001
1   bleeding duodenal ulcer   by endoscopy          end 12.06.2001
s   sudden weakness           +profuse sweating     ana 09.06.2001
s   black stool               x3                    ana 09.06.2001
t   blood transfusion         2 packs               iv  10.06.2001
t   lansoprazole (zoton)      15 mg x1 qd           cap 14.06.2001

```
                    PORTABLE HEALTH INFORMATION PACKAGE

HEALTH VIEW

**  ==============================
*
    Smith Robert                            data: 1995-6/2001    DOB 12.JAN.35

**  ============================== cvs

*        . 1
d   myocardial infarction                   anteroseptal         cln 25.02.1995
l   anteroseptal MI, acute                  QS in V1-V4          ecg 25.02.1995
l   narrow coronaries (LAD, RC, CIR)        100% 99% 70%         ang 03.03.1995
s   chest pain, severe                      on effort            ana 24.02.1995
t   coronary artery bypass graft    167     x3 coronaries        sur 06.03.1995
t   aspirin                                 100 mg x1 qd         tab 02.05.2001

**  ============================== eye
      169
*        . 1
d   glaucoma                                bilateral            cln 24.02.2001
l   increased intraocular pressure          46 mm Hg (bilat.)    pex 24.02.2001
s   blurred vision                                               ana 1/2001-->>

**  ============================== git

*        . 1
d   duodenal ulcer                                               cln 15.12.1998
l   duodenal ulcer                          by endoscopy         end 15.12.1998
s   heartburn                               before meals         ana since 7/98
t   omeprazole (Losec)                      20 mg qd             cap 16.12.1998

*        . 2
d   bleeding duodenal ulcer                 after aspirin        cln 12.06.2001
l   anemia                                  9,1 g%               bld 10.06.2001
l   positive occult blood in stool          +++                  stl 10.06.2001
l   bleeding duodenal ulcer                 by endoscopy         end 12.06.2001
s   sudden weakness                         +profuse sweating    ana 09.06.2001
s   black stool                             x3                   ana 09.06.2001
t   blood transfusion                       2 packs              iv  10.06.2001
t   lansoprazole (zoton)                    15 mg x1 qd          cap 14.06.2001

**  ============================== res

*        . 1
d   upper respiratory tract infection                            cln 22.11.2000
t   robitussin syrup                        1 tablespoon q3h     syr 23.11.2000

DATA RECORDING FORM [_____ _____]
first date  last date

NAME:_____ ID-NUMBER:_____ TEL:_____

| SYS | NO | T | DATA | DETAILS | SQ | SUB | DATE+TIME |
|-----|----|----|------|---------|-----|-----|-----------|

VERIFIED BY:_____ SIGNATURE:_____ DATE:_____

FIG 40

Structure for database:

```
Field  Field Name   Type        Width
    1  SYS          Character       3
    2  NO           Character       2
    3  T    205     Character       1
203 4  DATA         Character      34
    5  DETAILS      Character      17
    6  SQ           Character       2
    7  SUB          Character       3
    8  DATE         Character      10
    9  TIME         Character      11    209
   10  SOURCE       Character      15
** Total **                        99
                    207
```

FIG 41   201

```
                                            ┌─ 211
Record#  SYS NO T DATA                              DETAILS            SQ SUB
      1  skn 1  d urticaria after anti-tetanus                            cln
      2  skn 2  d urticaria after toxoid                                  cln
      3  skn 1  d drug eruptions (sulpha and iodine)                      cln
      4  skn 4  d erysipelas cruris, right                                cln
      5  skn 4  d erysipelas, Lt. leg, recc.      x5                      cln
      6  cvs 2  d thrombophlebitis, leg, lt.                              pex
214   7  cvs 2  d thrombophlebitis, left calf                             pex
      8  cvs 1  d varicose veins, legs            Lt. > Rt.               pex
      9  cvs 3  d hypertension, fluctuating                               cln
     10  cvs 3  l hypertension            ──┐     150/110                 pex
     11  res 1  s heavy smoker              └ 213  80-100 cig. qd     1   ana
     12  git 1  t appendectomy                                            sur
     13  ent 1  d follicular tonsillitis                                  pex
     14  ent 1  l high ASLO                       350                     bld
     15  gur 1  d urinary tract infections (x3)                           urn
     16  gur 1  d urinary tract infection                                 urn
     17  gur 1  d urinary tract infection         B. proteus              urn
     18  gur 1  d urinary tract infection         E.coli                  urn
     19  gur 2  l small right kidney              in ultrasound       1   usd
     20  gur 2  l no visualization, right kidney  isotope scanning    2   iso
     21  gur 1  d urinary tract infection         Pseudomonas             urn
     22  gyn 1  d menopause                                               ana
     23  gyn 2  d endometrial glandular hyperplasia                       cln
     24  gyn 2  s post-menopausal bleeding                                ana
     25  gyn 2  l uterine curretage                                       sur
     26  gyn 2  s meno-metrorrhagia                                       ana
     27  gyn 2  l uterine curretage                                       sur
     28  gyn 2  l atypical glandular hyperplasia                      1   his
     29  gyn 2  l uterine curretage               for PMB                 sur
     30  gyn 2  s vaginal bleeding                                        ana
     31  gyn 2  l uterine curretage                                       sur
     32  gyn 2  s post menopausal bleeding                                ana
     33  gyn 2  l uterine curretage               for PMB                 sur
     34  gyn 2  s post menopausal bleeding                                ana
     35  gyn 3  l trichomonas vaginalis           vaginal smear           bct
     36  met 1  d obesity, severe                                         cln
     37  met 1  l overweight, severe              136 kg                  pex
     38  met 1  l overweight, severe              143 kg                  pex
     39  met 1  l overweight, severe              161 kg                  pex
     40  met 1  t gastric bypass + gastrostomy    for overweight+++       sur
     41  git 2  l narrow gastro-jejun. anastomosis post op.               xrs
     42  git 2  t re-gastro-enterostomy           bypass stenosis         sur
     43  met 2  l hyperuricemia                   9.5 mg%                 bld
     44  met 2  l hyperuricosuria                 600 mg/24h          1   urn
     45  met 2  l hyperuricemia                   9.4 mg%                 bld
     46  met 2  l hyperuricemia                   7.6-8.9 mg%             bld
     47  met 2  t allopurinol                     100mgx2                 tab
     48  psy 1  d schizophrenia, acute episode    hospitalized            cln
     49  psy 1  d psychotic episode               hospitalized            cln
     50  psy 1  d schizophrenia, acute event      hospitalized            cln
     51  psy 1  t halidol                                                 tab
     52  psy 1  t phenergan                                               tab
     53  cvs 6  s chest pain                      after effort            ana
     54  cvs 6  s chest pain                      retro-sternal           ana
     55  cvs 6  s chest pain                      rad. Lt. shoulder       ana
     56  cvs 6  s chest pain                      like pressure           ana
     57  ??? 2  s cough, non productive           severe                  ana
     58  ??? 3  s vertigo                                                 ana
     59  ??? 4  s frontal hard mass, left         5-6mm                   pex
     60  ??? 5  l high SAP (serum alk. phosphatase) 100/85                bld
     61  ??? 1  s syncope                                             1   ana
     62  ??? 1  s syncope                                             2   ana
```

FIG 42

|Record#|SYS|NO|T|DATA|DETAILS|SQ|SUB|
|---|---|---|---|---|---|---|---|
| | | ↙222 | | | ↙221 | | |
|63| | | |Miller Nancy|Atlanta, GA. USA| |DOB|
|61|???|1|s|syncope| |1|ana|
|62|???|1|s|syncope| |2|ana|
|57|???|2|s|cough, non productive|severe| |ana|
|58|???|3|s|vertigo| | |ana|
|59|???|4|s|frontal hard mass, left|5-6mm| |pex|
|60|???|5|l|high SAP (serum alk. phosphatase)|100/85| |bld|
|8|cvs|1|d|varicose veins, legs|Lt. > Rt.| |pex|
|6|cvs|2|d|thrombophlebitis, leg, lt.| | |pex|
|7|cvs|2|d|thrombophlebitis, left calf| | |pex|
|9|cvs|3|d|hypertension, fluctuating| | |cln|
|92|cvs|3|f|hypertension|mother| |ana|
|95|cvs|3|f|hypertension|sister| |ana|
|10|cvs|3|l|hypertension|150/110| |pex|
|64|cvs|3|l|cardiomegaly|isotope scan| |iso|
|71|cvs|3|S|HYPERTENSIVE RETINOPATHY|GRADE 1| |pex|
|69|cvs|3|T|DIGOXIN|0,25mgx1 qd| |tab|
|70|cvs|3|T|FUSID|40mg qod| |tab|
|65|cvs|4|s|systolic murmur|grade 2/6| |pex|
|67|cvs|5|l|aortic insufficiency|echo-cardiogram| |eco|
|66|cvs|5|s|aortic insufficiency| | |pex|
|53|cvs|6|s|chest pain|after effort| |ana|
|54|cvs|6|s|chest pain|retro-sternal| |ana|
|55|cvs|6|s|chest pain|rad. Lt. shoulder| |ana|
|56|cvs|6|s|chest pain|like pressure| |ana|
|68|cvs|6|T|ADALAT|10mgx3 qd| |tab|
|13|ent|1|d|follicular tonsillitis| | |pex|
|14|ent|1|l|high ASLO|350| |bld|
|12|git|1|t|appendectomy| | |sur|
|41|git|2|l|narrow gastro-jejun. anastomosis|post op.| |xrs|
|42|git|2|t|re-gastro-enterostomy|bypass stenosis| |sur|
|15|gur|1|d|urinary tract infections (x3)| | |urn|
|16|gur|1|d|urinary tract infection| | |urn|
|17|gur|1|d|urinary tract infection|B. proteus| |urn|
|18|gur|1|d|urinary tract infection|E.coli| |urn|
|21|gur|1|d|urinary tract infection|Pseudomonas| |urn|
|19|gur|2|l|small right kidney|in ultrasound|1|usd|
|20|gur|2|l|no visualization, right kidney|isotope scanning|2|iso|
|22|gyn|1|d|menopause| | |ana|
|23|gyn|2|d|endometrial glandular hyperplasia| | |cln|
|25|gyn|2|l|uterine curretage| | |sur|
|27|gyn|2|l|uterine curretage| | |sur|
|29|gyn|2|l|uterine curretage|for PMB| |sur|
|31|gyn|2|l|uterine curretage| | |sur|
|33|gyn|2|l|uterine curretage|for PMB| |sur|
|28|gyn|2|l|atypical glandular hyperplasia| |1|his|
|24|gyn|2|s|post-menopausal bleeding| | |ana|
|26|gyn|2|s|meno-metrorrhagia| | |ana|
|30|gyn|2|s|vaginal bleeding| | |ana|
|32|gyn|2|s|post menopausal bleeding| | |ana|
|34|gyn|2|s|post menopausal bleeding| | |ana|
|35|gyn|3|l|trichomonas vaginalis|vaginal smear| |bct|
|88|heb|1|l|hepatomegaly|isotope scan| |iso|
|89|heb|2|l|septum in gallbladder|in ultrasound| |usd|
|36|met|1|d|obesity, severe| | |cln|
|37|met|1|l|overweight, severe|136 kg| |pex|
|38|met|1|l|overweight, severe|143 kg| |pex|
|39|met|1|l|overweight, severe|161 kg| |pex|
|40|met|1|t|gastric bypass + gastrostomy|for overweight+++| |sur|
|43|met|2|l|hyperuricemia|9.5 mg%| |bld|
|45|met|2|l|hyperuricemia|9.4 mg%| |bld|
|46|met|2|l|hyperuricemia|7.6-8.9 mg%| |bld|

FIG 43

PORTABLE HEALTH INFORMATION PACKAGE

HEALTH VIEW    ╱— 225

```
**  ================================
                        ╱ 226
 *                           Atlanta, GA. USA      DOB Aug12.1936
   Miller Nancy
**  ================================ ???╲227

*         1                                       ana 24.09.1963
 s  syncope                                        ana 18.02.1966
 s  syncope

*         2                           severe      ana 1968,69,70
 s  cough, non productive

*         3                                       ana 02-08-1983
 s  vertigo

*         4                           5-6mm       pex 08.08.1983
 s  frontal hard mass, left

*         5                           100/85      bld 28-08-1984
 l  high SAP (serum alk. phosphatase)

**  ================================ CVS

*         1                           Lt. > Rt.   pex 17.04.1978
 d  varicose veins, legs

*         2                                       pex +- 06/1982
 d  thrombophlebitis, leg, lt.                     pex 03.02.1986
 d  thrombophlebitis, left calf

*         3                                       cln since 1972
 d  hypertension, fluctuating          mother      ana at age 30
 f  hypertension                       sister      ana at age 25
 f  hypertension                       150/110     pex 07.12.1977
 l  hypertension                       isotope scan iso 29.04.1980
 l  cardiomegaly                       GRADE 1     pex 13.06.1964
 s  HYPERTENSIVE RETINOPATHY           0,25mgx1 qd tab 1965->1966
 t  DIGOXIN                            40mg qod    tab 1965->1966
 t  FUSID

*         4                           grade 2/6   pex 23.12.1982
 s  systolic murmur

*         5                           echo-cardiogram  eco 22.01.1986
 l  aortic insufficiency                            pex 04.08.1985
 s  aortic insufficiency
```

FIG 43a

```
*          6
s   chest pain                              after effort               ana 31.07.1963
s   chest pain                              retro-sternal              ana 01.01.1981
s   chest pain                              rad. Lt. shoulder          ana 02.03.1983
s   chest pain                              like pressure              ana 16.06.1983
t   ADALAT                                  10mgx3 qd                  tab since 1981

**  ================================= ent

*          1
d   follicular tonsillitis                                             pex 22.6.61-->
l   high ASLO                               350                        bld 28.06.1961

**  ================================= git

*          1
t   appendectomy                                                       sur 4June 1946

*          2
l   narrow gastro-jejun. anastomosis        post op.                   xrs 20.09.1984
t   re-gastro-enterostomy                   bypass stenosis            sur end of 84

**  ================================= gur

*          1
d   urinary tract infections (x3)                                      urn  1-7/1962
d   urinary tract infection                                            urn 25.12.1962
d   urinary tract infection                 B. proteus                 urn 31.05.1964
d   urinary tract infection                 E.coli                     urn ?June 1966
d   urinary tract infection                 Pseudomonas                urn 27.08.1984

*          2
l   small right kidney                      in ultrasound              usd 29.04.1980
l   no visualization, right kidney          isotope scanning           iso 28.07.1980

**  ================================= gyn

*          1
d   menopause                                                          ana at age 43

*          2
d   endometrial glandular hyperplasia                                  cln 06.03.1978
l   uterine curretage                                                  sur 06.03.1978
l   uterine curretage                                                  sur 28.03.1979
l   uterine curretage                       for PMB                    sur 10.12.1980
l   uterine curretage                                                  sur 30.01.1982
l   uterine curretage                       for PMB                    sur 14.05.1985
l   atypical glandular hyperplasia                                     his 28.03.1979
s   post-menopausal bleeding                                           ana at age 48
s   meno-metrorrhagia                                                  ana 24.03.1971
s   vaginal bleeding                                                   ana 27.08.1981
s   post menopausal bleeding                                           ana 03.02.1983
s   post menopausal bleeding                                           ana 10.05.1985

*          3
l   trichomonas vaginalis                   vaginal smear              bct 27.10.1983
```

FIG 43b

```
**  ================================= heb

*       1
1  hepatomegaly                       isotope scan         iso 23.07.1980

*       2
1  septum in gallbladder              in ultrasound        usd 14.06.1985

**  ================================= met

*       1
d  obesity, severe                                         cln since 1947
l  overweight, severe                 136 kg               pex 17.05.1965
l  overweight, severe                 143 kg               pex 17.04.1978
l  overweight, severe                 161 kg               pex 26.10.1983
t  gastric bypass + gastrostomy       for overweight+++    sur 20.12.1983

*       2
l  hyperuricemia                      9.5 mg%              bld 12.08.1982
l  hyperuricemia                      9.4 mg%              bld 17.12.1982
l  hyperuricemia                      7.6-8.9 mg%          bld 01-02/1983
l  hyperuricosuria                    600 mg/24h           urn 18.03.1983
t  allopurinol                        100mgx2              tab since 4/83

**  ================================= mus

*       1
l  BI-MALEOLAR FRACTURE, ANKLE, RT.                        xrs 21.05.1965
t  OPEN REDUCTION OF FRACTURE                              sur 24.05.1965

*       2
d  arthritis, rheumatoid                                   cln 21.01.1964
s  painfull swelling of joints                             ana since 1963

*       3
d  discopathy                         L4-L5                cln since 1971
l  herniation of lumbar discus        L4-L5                xrs 04.06.1971
l  osteophyte, L5                     isotope scan         iso 28.07.1980
s  LBP                                                     ana Since 2/71

*       4
s  shoulder pain                                           ana 01.01.1981
t  VOLTAREN                           50mgx3               tab January/81

*       5
l  DEG. CHANGES, CERVICAL VERTEBRAE                        xrs 00.02.1983
s  cervical pain                                           ana 18.01.1983
s  CERVICAL PAIN                                           ana 28.06.1984

*       6
d  TENNIS ELBOW, RT.                                       cln 18.08.1983

*       7
d  TENNIS ELBOW, LEFT                                      cln 26.09.1985

*       8
t  REPAIR OF POST OP. ABDOM. HERNIA                        sur 02.06.1986
```

FIG 43c

```
**  ================================  psy

*         1
d   schizophrenia, acute episode              hospitalized          cln 07.03.1976
d   psychotic episode                         hospitalized          cln 07.06.1964
d   schizophrenia, acute event                hospitalized          cln 14.06.1986
d   schizophrenia, paranoid                                         cln 2-4/1964
f   schizophrenia                             father                ana at age 55
t   halidol                                                         tab Start 1987
t   phenergan                                                       tab Start 1987

**  ================================  res

*         1
d   chornic obstructive lung disease                                cln 08.06.1983
l   obstructive lung disease                  pul. funct. tests     pft 08.06.1983
s   heavy smoker                              80-100 cig. qd        ana from age13
s   EXERTIONAL DYSPNEA                                              ana since 1977
t   ventolin                                  inhalation            inh 1983 (May)

**  ================================  skn

*         1
d   urticaria after anti-tetanus                                    cln 25.09.1953

*         2
d   urticaria after toxoid                                          cln 02.11.1970

*         3
d   drug eruptions (sulpha and iodine)                              cln August1977

*         4
d   erysipelas cruris, right                                        cln 27.03.1977
d   erysipelas, Lt. leg, recc.                x5                    cln 1978-1983
```

FIG 43d

| 231 |
|---|
| 59   Pellagra   ← 232 |

Steven B. Heymsfield, M.D., John R. Galloway, M.D.

CRITERIA FOR DIAGNOSIS

Poor diet, often compounded by chronic alcoholism, places the patient at risk for niacin deficiency. Skin lesions, alterations in mental status, and diarrhea suggest the diagnosis in such a setting. Niacin deficiency is present when the urinary ratio of $N^1$-methyl-2-pyridine-5-carboxamide to $N^1$-methylnicotinamide is less than one.

CLINICAL MANIFESTATIONS

SUBJECTIVE

Classic pellagra is due to a vitamin deficient diet, most importantly a diet deficient in niacin. The most common clinical setting is the chronic alcoholic who replaces calorie sources rich in vitamins with high-calorie, vitamin-poor alcohol. Dermatitis, diarrhea, and dementia are the hallmark of pellagra. The skin of the extremities becomes reddened when exposed to sun, and with chronic solar exposure, becomes dark and rough. The mouth and tongue become sore. The patient may have esophagitis, steatorrhea and abdominal pain. Hallucinations, anxiety, depression, psychoses, and stupor are frequent but nonspecific manifestations of cerebral involvement.

OBJECTIVE

A symmetric erythematous photodermatitis, especially of the extremities, is the characteristic skin lesion of pellagra. "Cassal's necklace," a band of dermatitis over the anterior neck, is found in some cases. Less specific skin changes include desquamation, hyperpigmentation, and edema. Neurological examination reveals

FIG. 44 the subjective disturbances discussed above and, in some cases, a peripheral neuropathy is present.

A decreased urinary excretion of $N^1$-methyl nicotinamide and $N^1$-methyl-2-pyridone-5-carboxamide is specific for pellagra. Other nonspecific laboratory findings include anemia, hypokalemia, hypocalcemia, hypoalbuminemia, and low plasma tryptophan. The electroencephalogram may show an increase in delta and theta wave activity, especially in those patients showing mental disturbances.

PLANS

DIAGNOSTIC

Classical symptoms are dermatitis, diarrhea, and dementia; however they do not very often appear together in the same patient. Reduction in plasma tryptophan levels is consistent with pellagra (normal concentration is 0.045 μm/mL). Reduced urinary excretion of $N^1$-methylnicotinamide occurs with onset of clinical symptoms and diminished excretion of $N^1$-methyl-2-pyridone-5-carboxamide occurs prior to clinical evidence of pellagra. Neither of these urinary assays are simple to perform nor readily available. Accordingly, the diagnosis is usually established after therapeutic response to nicotinic acid and other nutrients.

THERAPEUTIC

The treatment of pellagra is based on the administration of a high-protein diet in conjunction with niacin supplementation. The diet should consist of 1 g protein/kg body weight. Initially, the fat-intake should be low to avoid steatorrhea. Niacinamide is the preferred form of the vitamin, but niacin and tryptophan are also therapeutic. While the recommended allowance for niacin equivalents is 13–20 mg/day, a dose of 50 mg of niacin in addition to dietary niacin is necessary to reverse a deficient state. Dosages of 3 g/day or more may induce liver damage.

EDUCATION

A high content of niacin and its equivalents is found in liver, lean meat, poultry, eggs, milk, cheese, yeast, whole grain, nuts and legumes. Pellagra develops in chronic alcoholics and in those who consume low-protein diets. Pellagra may be secondary to malabsorption. In those already at risk because of inadequate diet, isoniazid, 6-mercaptopurine, 5-flourouracil, and chloramphenicol may precipitate pellagra.

FOLLOWUP

Following discharge, the patient should be seen every two to three months, and the diet history should be reviewed. If nutrition improves over three or four visits, the counseling program can be minimized to every six months to once a year.

DISCUSSION

BACKGROUND INFORMATION AND BASIC SCIENCE

Nicotinic acid, the by-product of nicotine oxidation, was discovered by Huber in 1867 (Figure 59–1). Pellagra was endemic to the United States during the first four decades of the twentieth century. Joseph Goldberger demonstrated in 1915 that pellagra was a nutritional disorder. In 1937 Elvehjem and coworkers cured black tongue, a related disease in dogs, with nicotinic acid. By 1945, acute cases were seldom seen due chiefly to economic progress.

Niacin is available in three forms: nicotinic acid, nicotinic acid amide, and the amino acid tryptophan which is converted to niacin in a 60:1 ratio.

Nicotinic acid forms the active portion of the coenzymes nicotinamide adenine dinucleotide (NAD) and nicotinamide adenine dinucleotide phosphate (NADP), both of which are necessary for cellular oxidative reactions.

NATURAL HISTORY

Inadequate cellular niacin is ultimately expressed as a dermatitis that starts on the extremities as an erythemous rash aggravated

NIACIN

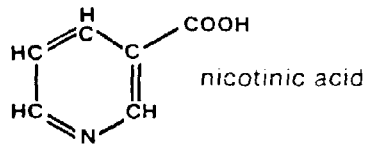

nicotinic acid

Occurrence: liver, lean meat, poultry, eggs, milk, cheese, yeast, whole grain, nuts, legumes

Function: nicotinamide adenine dinucleotide and nicotinamide adenine dinucleotide phosphate are coenzymes to dehydrogenases which function in cellular oxidative reactions Figure 59–1. The chemical structure, occurrence, active form, and functions of Niacin.

FIG. 44a

176  Nutritional disorders by sunlight and eventually leads to hyperpigmentation and exfoliation. If left untreated, the patient progressively weakens from diarrhea and electrolyte disturbances, and death results. However, with proper treatment most patients recover rapidly. Severe cases may suffer irreversible neurological damage. Dietary habits must be improved to prevent relapse.

PREVENTION

Pellagra may be prevented by adequate dietary intake or by the supplementation of niacin equivalents (see "Education"). If alcoholism is the cause of a poor diet, the patient should be educated on the relationship of alcohol abuse to poor diet and pellagra.

COST CONTAINMENT

Nutritional counseling of the undernourished alcoholic patient is the first step in the prevention of this disorder. Niacin is inexpensive in supplement form, and it is easy to obtain in a variety of food sources.

REFERENCES

Bogert LJ, Briggs GM, Calloway DH. Nutrition and physical fitness. 10th ed. Philadelphia: W.B. Saunders Company, 1979;183–91.
Darby WJ, McNutt KW, Todhunter EN. Niacin. Nutr Rev 1975;33(10):289–95.
Desgrosseilliers JP, Shiffman NJ. Pellagra. Can Med Assoc J 1976;115:768–70.
Goldsmith GA. Niacin: antipellagra factor, hypocholesterolemic agent. JAMA 1965;194(2):167–73.
Sauberlich HE, Dowdy RP, Skala JH. Laboratory tests for the assessment of nutritional status. CRC Crit Rev Clin Lab Sci 1973;4:215–340.
Spivak JL, Jackson DL. Pellagra: an analysis of 18 patients and a review of the literature. Johns Hopkins Med J 1977;140:295–309.
Stratigos JD, Katsambas A. Pellagra: a still existing disease. Br J Dermatol 1977;96:99–106.

FIG. 44 b

```
                    PORTABLE HEALTH INFORMATION PACKAGE
                              HEALTH VIEW           233

** ===================================
 *
     PELLAGRA    ← 232                     from TEXTBOOK

** =============================== GIT   234
 *
     DIARRHEA
     ESOPHAGITIS
     STEATORRHEA
     ABDOMINAL PAINS

** =============================== HEM   234
 *
     ANEMIA

** =============================== MET
 *
     N1-METHYL NICOTINAMIDE              1. urn. excr.
     N1-METHYL-2-PYRIDONE-5-CARBOXAMI    1. urn. excr.
     HYPOKALEMIA
     HYPOCALCEMIA
     HYPOALBUMINEMIA
     TRYPTOPHAN, LOW                     < 0.045 nm\ml
     HIGH-PROTEIN DIET                   1 g.prot./kg
     NIACIN                              0.3-1.0 g/day
     LOW FAT DIET (INITIALLY)            avoid diarrhea
     HIGH CONTENT OF NIACIN              liver, meat ++
     FOLLOW-UP                           Q. 2-3 months
     REDUCE ALCOHOL INTAKE               in alcoholics
     MALNUTRITION                        niacin def.
     ALCOHOLISM, CHRONIC
     METHYPYRIDINE/METHYLNICOTINAMIDE    < 1

** =============================== NEP
 *
     DEMENTIA
     HALLUCINATIONS
     ANXIETY
     DEPRESSION
     PSYCHOSIS
     STUPOR
     NEUROPATHY, PERIPHERAL
     DELTA WAVE ACTIVITY                 increased
     THETA WAVE ACTIVITY                 increased
```

FIG. 45

```
**  ================================= ORL

*
    SORE TONGUE
    SORE MOUTH

**  ================================= SKN

*
    SKIN REDDENING, EXTREMITIES            by exp. to sun
    SKIN DARK & ROUGH, EXTREMITIES         chr. solar exp
    PHOTODERMATITIS, ERYTHEMATOUS          symetr. extrem
    "CASSAL'S NECKLACE" DERMATITIS         anterior neck
    DESQUAMATION
    HYPERPIGMENTATION
    SKIN EDEMA
```

FIG. 45a

… # PORTABLE PERSONAL HEALTH INFORMATION PACKAGE

This application claims the benefit of U.S. Provisional Application No. 60/331,098, filed Nov. 8, 2001.

COPYRIGHT NOTICE

A portion of the disclosure of this patent document contains material, which is subject to copyright protection. The copyright owner has no objection to the facsimile xerographic reproduction by anyone, of the patent documents or the patent disclosure in exactly the form it appears in the Patent and Trademark Office patent file or records, but otherwise reserves all copyright rights whatsoever.

BACKGROUND OF THE INVENTION

1. Field of the Invention

The present invention relates, generally, to the field of collection, storage, transfer and display of health data, and more specifically, to the field of collection, storage, transfer and display of health data on portable devices.

2. The Problems

Immediate availability of accurate, reliable past medical history of a patient is important in most health care encounters. Caregivers need data from the past health history of a patient, in order to arrive at the correct diagnosis, institute the appropriate therapy and ensure the continuity of care. In emergency medical situations, incomplete information can lead to disastrous clinical results. Even in routine encounters immediate availability of up-to-date, accurate, and comprehensive health data at the point of care is often extremely important. A physician spends in an average clinic visit about 30% of his time on data collection. Usually, clinicians try to get the relevant data from the past health history of a person, mainly from one or more of the following sources: the patient himself, conventional paper based medical records, a variety of documents (letters, discharge summaries, X-rays, ECGs, laboratory reports, consultants' reports, etc.), computer-stored medical records (on personal computers, traditional mainframe computers, computer based medical record systems, and web-based medical records) and directly from other health care providers. Unfortunately, in most cases there are problems, that prevent clinicians to get all the relevant data from the past health history of patients, at the point of care.

The main problem is that, the personal health records of a person are usually distributed amongst multiple health care providers. A patient may obtain the services of a number of providers when being treated for a single particular illness or injury. Over the course of a lifetime, a patient may receive the services of a large number of providers. Therefore, parts of the health data of one patient may be stored in paper based and/or computer based medical records of his primary care physician, one or more consultants, inpatient departments and outpatient clinics of hospitals, emergency departments, sports medicine clinics, public health clinics, dentists' and optometrists' charts, nursing homes and other institutions such as the armed forces, occupational health programs of employers, schools, colleges, universities etc. In addition, modern transportation for business or travel increases the possibility, that medical service or continuation of care will be needed and documented in medical records in one or more locations anywhere in the world. Therefore, linking, integrating and presenting all the data from the past medical history of a patient, that are stored on multiple paper based records and multiple computer based records, so that the caregiver at the point of care, will have an integrated view of all the data is usually impossible. At best, each one of these sources may be able to supply, only the part of the health information that is recorded and stored in its archives. Unfortunately, even the limited data that caregivers can get from each one of these sources are often incomplete and inaccurate.

Another universal problem that prevents clinicians to get all the relevant data from the past medical history of patients, at the point of care from all health records of a patient, is the fact that very often, one person has different names and/or identification numbers in different paper based and/or computer based medical records. Many countries do not have unique patient identifier systems. Therefore, in these countries, when a person is admitted to a hospital, he receives a patient ID that is used only within that hospital. If a patient is admitted to several hospitals, he will have several patient IDs. In the United States a Social Security Number is not always assigned at the time of birth and therefore, important data collected on newborn babies, are often stored in records that have different ID numbers than the permanent Social Security Numbers. When an unconscious person is admitted to an emergency department without his Social Security Number, data related to that event are recorded and stored in a medical record that is assigned a temporary Social Security Number, that is obviously different from his permanent Social Security Number. If the temporary and permanent Social Security Numbers are not merged in a timely fashion, it becomes very difficult or impossible to access, link and integrate the important health data that are stored on temporary medical records, with data that are documented and stored on permanent records. Also, the same patient may be registered under different names and ID numbers because of typing errors, marriage, divorce or use of pseudonyms. There are many documented cases in which one person has more than one permanent social security number (there are about 280 million Americans and about 360 million active social security numbers). There are also identified cases in which two people have the same Social Security Number. Thus, many people have more than one identifier. Master Patient Indexes cannot solve this problem. They are useful as internal aggregators in health institutions, but not as a way to identify and get access to patient records externally. Therefore, at least part of the personal health data, that are recorded in some of the health records of a person cannot be linked, integrated and used, when these data are needed at the point of care.

Usually, the patients themselves cannot supply all the data that caregivers need at the point of care. Some patients simply do not know the details of their past medical history, because their physicians do not tell them important facts. Other, patients cannot supply the information, because they did not understand what was explained to them. Many caregivers prevent patients to view their own personal records, and patients rarely receive detailed information in written form about their treatment in hospital or specialist clinic. Thus, they must rely on their own understanding of what has happened to them. Therefore, often a significant disparity occurs between perceptions of physicians and patients regarding hospital discharge instructions (Calkins, 1997). In a study done at the Mayo Clinic, patients and physicians were asked to report on major health problems and other problems dealt with during an ambulatory-care encounter. Patients failed to report 68 percent of problems that their physicians listed as being addressed during a specific encounter (Scheitel, 1996). In addition, 54 percent of the "most important health problems" that physicians discussed during the encounter were not even listed among those, that patients recounted after the encounter. In emergency situations, the patient may be unconscious and not be able to provide information. Even if conscious, a patient may be incapable of providing complete, accurate, exact and comprehensive information, when he is tired or painful and can not concentrate. There are many cases in which patients supply unintentionally misleading information. For instance, nine out of ten patients who honestly believe they are seriously allergic to penicillin are mistaken (Saxon, 1987).

The memory of patients is not always reliable. A number of physiological and pathological conditions may be responsible for temporary or permanent loss of memory. Studies have shown, that a patient's ability to recall information presented by physicians in outpatient clinics, ranges from 50 percent at 5 minutes to 56 percent at 1-2 weeks. When patients are exited, tense or frightened in the examining room, they tend to forget to tell the physician the most important facts about their medical problems. In a study of patients' recall of medication information, 60 percent of patients did not know the names of their drugs and 20 percent did not know the purpose of their medications (Ley, 1982). In elderly patients distinct memory impairment is common (Welsh-Bohmer, 1999). Even young and healthy persons may be incapable of providing complete, accurate, exact and comprehensive information related to their past medical history. The recall of injury events, which resulted in seeking treatment from a doctor, nurse or dentist, or going to the hospital for treatment in the previous two years, was studied for a group of 631 thirteen year olds (Langley, 1989). This study showed that 39% of all visits to the accident and emergency department were not recalled. A poisoning study showed that one fifth of the entire previous year's poisoning experience was reported for a one-month period immediately preceding the interview (Wherle, 1960). There are many other studies that document human memory failures (Sharp, 1990). Thus it is clear that the data that patients can supply to caregivers about their past medical history at the point of care, are very often incomplete, inaccurate, or even false and misleading, and can lead to serious errors in diagnosis and therapy.

The paper based medical record, is often not one entity, even within one institution, because data related to accident and emergency visits are very often stored separately, and many other departments and services maintain separate and/or more detailed patient data files that are not part of the central record. Some studies indicate that when scheduled and unscheduled appointments are considered together, the entire medical record is not available 30%-40% of the time. The high rate of unavailability of paper based medical records is attributed mainly to the following causes: patients being seen in two or more clinics on the same day, charts not being forwarded, physicians keeping records in their offices or removing them from their offices, and records being misfiled in the file room. Another reason for unavailability of paper based medical records is, that paper based medical records are usually stored for up to 25 years, depending on state laws. Then, because of limited storage space in their archives, some institutions destroy the old records, X-ray films and other documents, ignoring the fact that the data may be needed many years later for care of elderly patients.

Even in cases, in which a paper based medical record is available at the point of care, extraction of data form the record is usually difficult. The contents of a conventional paper based medical record is often a mixture of admission notes, follow-up reports, laboratory test results, ECG strips, administrative documents, consultants' notes and recommendations, therapy plans, medication records, informed consent forms, flow charts etc. Much of the information in the record is obsolete, redundant and duplicated. Significant parts of the data are handwritten and often illegible. In one study, the main finding was that 50 percent of handwritten emergency department charts could not be properly evaluated due to poor handwriting. Notes pertaining to a single problem may be pages apart, depending on the time intervals between visits. Therefore, dozens of pages must be thumbed through in a paper-based record, in order to find the desired information (Brancati, 1992; Brown, 1988). A study that was conducted in a university hospital clinic, to determine the success with which physicians find patient information using traditional hospital paper based medical records as a source of data, showed that even though the medical records were present 95% of the time in their study, physicians could not find all the information they were looking for, in up to 81% of the visits (Tang, 1994). Therefore, it is not surprising that house officers frequently do not try to obtain previous paper based medical records (Fred, 1994).

Even in cases, in which a paper based medical record is available at the point of care and is easily legible, extraction of data form the record is usually difficult. Notes may be too ambiguous to allow proper interpretation, because data are recorded in narrative style that contains complex expressions. In these narrative expressions that are recorded in natural language, often (24%) two or more data elements are linked together. It is also common (39%) that in natural language one data element may be embedded in another. Studies have shown that these expressions increase the cognitive load and the reader may need more time and effort to extract from these expressions the data elements (Patel, 2000). In a sentence in which each word can have different meanings, the whole sentence may have more than 10 interpretations (van Bemmel, 1997). In the time constraints of most points of care, this may lead to serious errors in interpretation of the meaning of complex notes, which in turn, may lead to errors in medical decisions and actions. Even when each sentence or paragraph is accurately understood, the scattered notes make it difficult to obtain an overview of the complete medical history of a patient, especially in cases of patients that are treated for more than one complaint or disease.

Although paper based medical records are technically transferable, it is a generally accepted principle that the patient record is maintained and owned by the health care institution or practitioner providing care. This principle, which is established by statutes and regulations in many states, grants the provider control over the physical document (CPRI, 1994). Therefore, the paper based medical records of a patient that is treated in one institution, are usually not transferred for use by medical personnel in another institution, especially when the patient needs medical care in another city, country or continent. Theoretically, copies of medical documents carried by the patient, could supply at the point of care, all the data from the past medical history of a patient. Already in 1973 it was suggested, "that legislation be passed to require that a complete and unexpurgated copy of all the medical records, both inpatient and outpatient, be issued routinely and automatically to patients as soon as the services provided are recorded" (Shenkin, 1973). This suggestion is not practical, because it is very difficult to carry paper copies of complete medical records and also, because the fact that there are caregivers that prevent patients to view and copy their own personal records. Thus, most patients do not carry with them at all times, paper copies of all their medical records, discharge summaries, roentgenograms, electrocardiograms, letters, reports of laboratory tests and procedures.

Timely access to patient data that are stored on computers is very often prevented from caregivers that need fast access to the data at the point of care, mainly by one or more of the following reasons: absence of the necessary hardware or software at the point of care, lack of interoperability of hardware or software between multiple vendor systems from various sources that use different formats and standards (which also change over time), lack of access to a reliable communication network, data protection policies and lack of adequate skills required to use the system. Thus, for instance, a physician that is called to examine and treat a person in an emergency situation in the middle of the street, a paramedic in the field or a nurse visiting an elderly patient at his home, may not have immediate access to the relevant data, because of lack of access to the necessary hardware, even if they are authorized to access the data of the relevant remote computer.

Many caregivers cannot use computer based medical record systems efficiently, mainly because these systems are often difficult to learn and difficult to use (Sittig, 1999). A typical screen in most electronic medical record systems contains dozens of icons and pull down menus, which the user is supposed to know well, in order to use them for many tasks, such as entry and retrieval of administrative, clinical, scientific, financial and statistical data, and also scheduling, typing letters, prescriptions and reports, sending and receiving e-mails, etc. Although vendors describe these programs as user-friendly, they are usually complex. Many studies have shown that computer based interactions take longer than paper based interactions (Krall, 1995) and that users sometimes avoid documentation of details, if they feel that it will take too much of their time and effort.

In most electronic medical records data are clustered in groups that are not oriented to clinical scenarios. In order to enter or retrieve data that they need, related to one problem, clinicians, need usually to use many screens. They have to know which one of the many screens show laboratory test results and which show reports of X-ray examination, which screens show diagnoses and which show treatments or procedures, etc. In order to get all the data that they need to review and deal with one problem, they must usually "jump" from one screen to another. Thus, most computer based medical records do not enable every user, at the point of care, to see in one view all the data that he needs, before he makes a decision. This may lead to delays and errors in medical decisions and actions.

Even in cases, in which those barriers do not exist, it may be difficult to get accurate data, mainly because of the methods of data entry in computer based health records. In most of them data are recorded and stored by selecting terms from one or more lists of a variety of classifications, lexicons, data dictionaries, nomenclatures, and structured coded controlled vocabularies that are presented on the screen. Using coded data entry does not allow caregivers to express the complaints of their patients in the patients' own words. Using controlled terminologies from a list to enter data, do not allow caregivers to record exactly what they themselves want to express in their natural professional language. Also, very often clinicians cannot record important observations using coded data entry, because there are no codes to do it (Chute, 1998). Thus, data that are recorded using classifications, nomenclatures, and structured coded controlled vocabularies, are often not accurate and incomplete. Data entry by selecting an option from a list may also increase the risk of entering errors that are difficult or almost impossible to detect. For instance, it is very easy to click option 1 in a list (that stands for "yes") instead of option 2 (that stands for "no") or to click option 3 in a menu (that stands for "electrophoresis") instead of option 4 (that stands for "electrolytes"), which may have serious consequences when these erroneous data are used by clinicians, at the point of care, to make a diagnoses or decide on diagnostic procedures or treatments.

Use of predefined date-fields to record time in computer based systems, may result in confusion. For example, a calendar date is expressed in the United States in the MM/DD/YY format. In Europe the DD/MM/YY format is used. In other countries the YY/MM/DD, the DD/MM/YYYY or a variety of other formats are used to represent dates. Thus, 07/01/21 may mean "Jul. 1, 1921 ", "Jan. 7, 1921 " and even "Jan. 21, 1907 ", depending on the country and the format used. Use of predefined date-fields, does not allow accurate documentation of temporal uncertainty and multiple temporal granularities, and may result in entering inaccurate or even false information. For instance, when a patient does not know or does not remember the exact day and month of an event, clinicians try to document the event using the MM/DD/YY as 00/00/YY, or even better as ??/??/YY. Unfortunately, very often the software does not allow to enter such "invalid" dates, ignoring the fact that in collecting data, we are often faced with answers from a patient, expressed in natural language, which cannot fit into any predefined date field. Therefore, the users are driven to enter a false day and month, to satisfy the system. Entering such inaccurate or false data may confuse a physician about the time sequence of events, from the past medical history of a patient, and may have serious consequences, when these data are used by clinicians, to make diagnoses or decide on diagnostic procedures or treatments.

The protection of privacy, confidentiality and access control to patient information in paper based and computer based medical records are often inadequate. Usually, a patient cannot maintain anonymity. In most cases, at the time of registration, a patient must provide personal identifying information such as name, date of birth, address, telephone number, marital status, occupation, ID number etc. Very often, patients have limited control or no control on the security, confidentiality and access to these personal health data, which are stored in patient records. Authorized users of health records, mainly those that have "role based access" to patient specific information, and who are not directly involved in patient care, may abuse their privileges by accessing information for inappropriate reasons or uses, whether to view records of friends, neighbors, or coworkers. There is also a pervasive use of compiled health information for marketing purposes, which constitutes a serious invasion of a person's privacy, and against which it is very difficult to fight. Many cases are reported in the media. These universal problems, of misuse and unauthorized disclosure of personal health data, that many people consider to be one of their most important secrets, has caused patients to withhold from recording in medical records clinically important, but sensitive personal information, because they think that if the information will be known, it might threaten their employment, insurability or credit rating. Also, parents, under some conditions, may withhold information about a child from medical professionals for the same reasons (MacFarlane, 1992). Furthermore, physicians are being forced to censor essential chart information that might harm the patient. For example, a physician may hesitate to record that a prominent executive has become a sloppy dresser, although this might be a valuable clue to incipient dementia.

The security of patient information in paper based and in computer based medical records can be protected by a combination of policies, procedures, and a variety of technological measures. Implementation of the necessary measures is often complex and expensive. Therefore only a limited number of health care institutions are able to install all the necessary components and use them adequately. Protecting the privacy and security of sensitive patient information on remote computers requires that the digital identity of the patient, physician and clinic or hospital be authenticated before the patient's clinical information is released to the patient-approved physician. In institutions that install such methods and procedures, the protective measures themselves are often significant barriers to the timely access to patient data at the point of care (Overhage, 2002). This situation is very common. Caregivers that are not affiliated with a specific institute (that work in another institute, another city, country or continent) are usually not authorized in advance to access the data that are recorded and stored in computer systems of that institute, and therefore can not use patient specific data that are stored in that institute, when they need the data at the point of care.

Another serious problem with computer based medical record systems is that they have many secondary uses, ranging from billing and statistics to clinical research and national health policy development. The imposition of cost control and reimbursement regulations, often force users to enter inaccurate, incomplete and even false clinical information into the personal medical records of their patients, because they require the information to be framed in arbitrarily unrealistic terms and classes. For instance, when a physician believes that a given patient should be hospitalized, and the admission criteria require a respiratory rate of 34 per minute and the treatment standards call for cardiac rhythm electronic monitoring and intravenous therapy, he may be tempted to enter false data, to satisfy the admission criteria (Burnum, 1989). After such inaccurate, incomplete or false data are recorded in medical records, and due to hiding of important data, it may be difficult or even impossible to detect that the data are unreliable. Obviously, using inaccurate, incomplete or false data at the point of care, may lead to serious errors in diagnosis and therapy.

Clinical reporting represents a major cost to the health care industry, in terms of both dollars and time. Writing detailed discharge summaries, referral letters and consultation reports by hand onto paper has two significant disadvantages: it is time consuming and may be illegible. Dictating, printing, reviewing, and approving printed medical documents are time-consuming processes. The transcription services used by many physicians as a mechanism for generating clinical documentation are also expensive and error-prone. While they fulfill the traditional purpose of documenting patient encounters, it is difficult or impossible to integrate them with other records of the (increasingly electronic) longitudinal patient record. In most cases, these documents contain only part of the data that caregivers need at the point of care.

Sending information such as referral letters, discharge summaries, and copies of documents to the point of care by regular mail is often very slow (Tulloch, 1975; Bado, 1984; Penney, 1988). A study that looked at all hospital discharge communications concerned with acute admissions from one general practice, found that over half the patients contacted their general practitioners after discharge, before the general practitioner had received information about the hospitalization. The general practitioner received no information for 11% of the discharged patients (Mageean, 1986). Therefore, primary care physicians are frequently unaware of the discharge plans for their hospitalized patients. Specifically, because discharge summaries are not readily accessible, the primary care physician responsible for the post-discharge care of a patient has no quick and reliable access to information about a recent hospitalization. Information such as the reason for the hospitalization, test results, diagnosis, and discharge medications may have a profound impact on how the patient is managed in clinic post-discharge. Additionally, the inpatient physician has no reliable way of communicating requests, such as further testing needed, to the outpatient physician (Moore, 1997).

Transmitting documents to the point of care by standard fax machines is not secure. Faxes may be easily sent to the wrong place by an error in dialing (Genesen, 1994). Faxes may also be misdirected by pressing the wrong speed-dial button, and thus enable inadvertent disclosure of sensitive personal medical data of a person to his employers, coworkers and others, whose fax numbers are used often by the sender. These common problems with faxing may prevent timely arrival of important personal data of a person that are sent to the point of care. Interception and unauthorized capture of faxes during transmission on phone lines is extremely easy, and neither the senders nor the receivers, know when this happens. Faxes that are printed on thermal paper may fade and become illegible after a relatively short period. Because of these problems, it is not recommended to transmit personal health information, on standard fax machines. Secure fax devices can authenticate the sender and receiver, encrypt the faxes before transmission, and store faxes in electronic mailboxes that can be opened by the user only by entering a user ID and PIN to get the faxes out. Unfortunately, these systems are expensive and enable to transmit faxes securely only within a closed network of fax machines, in which secure fax devices are installed. Therefore only a limited number of health care institutions are able to install and use them.

Internet access to patients' records, using PC based browsers, is not possible in many situations, mainly because of the absence of the necessary hardware or software at the point of care, lack of access to a reliable communication network and lack of adequate skills required to use the system. In addition, in order to be able to access the data, the person requesting the information must know his patient's web address (URL), and the system must confirm the requestor's "need to know" and the identify the patient (Schoenberg, 2000). If the requester does not know the URL and cannot supply the relevant identifying data, he cannot gain access to the needed health data. Also, caregivers that need immediate access to important data at the point of care cannot rely on web-based transmission of patient specific data, because Internet paths consistently show large time-of-day and day-of-week variability. The effective transmission capacities of network pathways are generally reduced during the business day. This appears to be directly related to the much higher level of use during the day. The transmission capacities are the greatest during the night or early morning hours. Typically, for web sites tested in the United States and other G7 countries, the effective transmission capacities are reduced on the order of 40 to 95 percent during local business hours compared with weekend and other off-peak hours. The data suggest that even high-bandwidth (e.g., 10 to 45 Mbps) Internet pathways may suffer from significant capacity reductions because of traffic congestion during peak hours, probably reflecting a loaded Internet infrastructure in some geographic regions (Wood, 1998).

E-mail messages are inherently insecure, and may suffer during transmission from unauthorized or accidental modification, destruction and disclosure. Unencrypted, unauthenticated e-mail messages may be corrupted or incomplete, or may incorrectly identify the sender. Currently, standard e-mail systems do not use encryption and strong authentication methods. Many standard e-mail systems use store-and-forward protocols, that leave copies of messages on various insecure servers and end-user hard drives. E-mail messages may be misdirected by mistakes such as clicking the e-mail address of another person or by selecting the "reply all" option, which sends e-mails to the sender's and also to one or more other e-mail addresses. These problems may enable inadvertent disclosure of sensitive personal medical data of a person to his employers, coworkers and others, whose e-mail addresses are used often by the sender. Patients or physicians who use e-mail for medical data interchange in the workplace are not assured confidentiality and may unintentionally expose sensitive details of illness or social circumstances to an employer because, legally e-mail systems allow the employer access to all messages generated and read by employees. Further, patients using family e-mail accounts at home may lack privacy from spouses, children, or parents.

Receiving the relevant past medical history of a patient by direct telephone communication from the point of care, with other clinicians, is often impossible. Most caregivers at the point of care do not have the time to find telephone numbers of the relevant clinicians and to contact them. The phone call interrupts workflow and requires the receiver to be available. Health information that caregivers receive by phone calls from patients is often not entered into the medical record and is therefore not available at the point of care. Also, information that is communicated by unprotected telephones, may be heard by unauthorized people, on parallel connected lines and neither the senders nor the receivers, know when this happens. But, even if a caregiver at the point of care succeeds to contact another caregiver by protected telephone line and gets data from the past medical history of a patient, it might be extremely dangerous to rely on these data. Communication failures are a large contributor to adverse clinical events and outcomes (Coiera, 2000). In a retrospective review of 14,000 in-hospital deaths, communication errors were found to be the lead cause, twice as frequent as errors due to inadequate clinical skill (Wilson, 1995). Furthermore, about 50 percent of all adverse events detected in a study of primary care physicians were associated with communication difficulties (Bhasale, 1998).

Consumer health records are usually created and maintained by individual patients on the web. The documentation is based upon the patient's own understanding of his health conditions, medications, problems, allergies, vaccination history, etc. Although consumer health records may contain important data, most caregivers do not use them at the point of care. They cannot rely on data that are entered by laypersons, for decisions on diagnoses, procedures and therapy, because these data are usually inaccurate and incomplete (Kim, 2002). In addition, the protection of the privacy, confidentiality, security and access control to web based consumer health records is often inadequate (Marshall, 1999). In PC based consumer health record systems, the software and the data are stored on the hard disk of the personal computer at the patient's home (Denton, 1999). Therefore, these data cannot be easily accessed from remote sites.

Accessing, linking and presenting patient data that are distributed across multiple hospitals and health maintenance organizations, primary care physicians and specialists' clinics, pose very complex technical and non-technical problems. These include problems of interoperability between multiple vendor systems from various sources that use different formats and standards (which also change over time), access control, routine maintenance of hardware and software, data protection laws, regulations and policies, downtime issues, training of the technical and clinical users, incompatible standards for linking and integrating patient data that are stored on multiple heterogeneous component systems and on paper based legacy systems. A variety of national and international organizations such as ISO 251, CEN 215, ASTM, HL7, CCOW, CORBA, and many others are developing standards that are supposed to enable the merger of the individual data elements stored in heterogeneous computer based systems and the provision of a patient view, rather than an organizational view of patient information. Unfortunately, the standards used in different local, regional and national organizations are often incompatible. Therefore timely access, to at least parts of the data that are stored on computer based medical records systems of large integrated health maintenance organizations, is often difficult or impossible, in many points of care.

Thus, although enormous amounts of personal health data are collected and stored for each patient in a variety of health record systems and documents, in most cases there are problems that prevent clinicians to get all the relevant data from the past health history of patients at the point of care, when the patient is seen by physicians and other health care professionals. These are very common universal problems and they have very serious consequences for patients, caregivers, insurers and society at large.

3. The Consequences

Absence of all the relevant data from the past medical history of patients at the point of care may cause critical delays in diagnosis and treatment and waste of time of the patient and caregivers. In the absence of these data, at the point of care, a patient must waste time in giving the same history time and time again, and a physician must spend during an average clinic visit 30%-40% of his time on data collection. When a physician examines a new patient that suffers from a few chronic diseases, it may take from about 15 minutes to an hour or more to collect all the relevant data from the patient and from medical records and relevant documents.

In the absence of relevant data from the past medical history of patients at the point of care, the patient must submit to the same diagnostic tests and procedures repeatedly, and insurance companies waste enormous amounts of money on unnecessary and potentially dangerous tests. In 1987 it has been estimated, that of the approximately $30 billion spent each year in the United States for medical tests, as much as 60% of that amount ($18 billion) is wasted on unnecessary tests; i.e., those which, for a given patient, would not be needed if the physician had the benefit of a reliable medical history.

In the absence of all the relevant data from the past medical history of patients at the point of care, caregivers must make decisions with minimal, inaccurate, incomplete and imprecise information or even no data. Without information, dangerous treatments may be undertaken by caregivers on a balance of risk basis, allergies and sensitivities to certain foods and drugs may not be known, and previous test results may be ignored. Lack of information about the need of a patient to receive life maintaining drugs may cause abrupt discontinuation of essential drugs such as anti coagulants, anti epileptics, anti hypertensives, anti diabetics, anti arrhythmics and corticosteroids. This may result in erroneous and harmful treatment of the person allergic to some drug, and/or in need of some drug such as insulin for the diabetic person, or digitalis for a person of heart-failure indications and the like, and even cause life threatening situations, which may necessitate repeated hospitalizations.

In the absence of up-to-date, accurate, and comprehensive relevant health data from the past medical history of a patient, at the point of care, caregivers may make fatal errors. A report from the National Academy of Sciences' Institute of Medicine, cited studies showing that between 44,000 and 98,000 people die each year in hospitals in the United States, because of mistakes by medical professionals. Even when using the lower estimate, more people die each year in the United States from medical errors than from motor vehicle accidents, breast cancer, or AIDS. Each day, more than 250 people die in the United States, because of mistakes—the equivalent of a major airplane crash each day and every day. Countless more people are injured, according to the Institute of Medicine, which ranked medical errors the eighth most common cause of death in the United States. The annual financial cost is enormous with estimates running as high as $29 billion dollars a year just for preventable medical mistakes. In fact, it is clear that the magnitude of the problem is understated in the report of the Institute of Medicine, mainly because the study concentrated only on data from hospitals and did not collect data on medical errors that occur in other places in which Americans receive health care, such as nursing homes and ambulatory care centers. Extrapolation of these American data to the 6 billion people in the world gives frightening figures.

4. Prior Art Solutions

To solve these very common and very serious universal problems that are caused by unavailability of data from the past medical history of a patient at all points of care, enormous amounts of time, money, efforts and ingenuity were invested by innumerable commercial bodies, academic institutes, national and international organizations and individuals, over decades in developing devices and methods, by which health information could accompany a patient to all health care encounters. These prior art devices include a variety of eye readable paper based data cards, patient held paper based records and booklets, lockets, pendants, necklaces, bracelets and wrist bands that carry paper based printed information, microfilm devices, bar code cards, magnetic stripe cards, health watches, integrated circuit smart cards, optical memory cards, hybrid cards, PCMCIA cards, floppy disks, portable computers, personal digital assistants (PDAs), cellular telephones, devices that carry a personal ID number and a telephone number, which emergency medical personnel can use to call an emergency response center, in order to get information about a person's health problems, medical CD cards, implantable chips, and many other devices and methods.

Each one of these prior art portable personal health information devices and methods, can at best supply only part of the personal health data of a person—but no one of the them can provide instant access to a complete, accurate and up-to-date health information of a person, whenever the information is needed, at all times, at all points of care, anywhere in the world, for all health care professionals. Also, no one of these portable personal health information devices and methods, enable to record, link, integrate, display and print in a variety of clinically relevant organized forms, all the health data of a person from birth to death, collected from all paper based medical records, computer based medical records, and all other sources of information, including personal informal paper based notes, verbal communications, phone calls and e-mails.

SUMMARY OF THE INVENTION

The invention is a portable personal health information package owned by a person, which enables him to carry his complete health information in his pocket at all times, and grant his caregivers instant access to his health data whenever they are needed, at all points of care anywhere in the world.

The invention provides all the elements needed to use it instantly anywhere in the world with no exception: a database management software program and a personal database file, which are contained in a portable computer readable storage device, a data recording form, and a printed health view.

OBJECTS AND ADVANTAGES

From reading the background of the invention, which describes the universal problems of access to patient data at the points of care, several advantages of my personal health information package become evident regarding collection, storage, transfer, retrieval and display of personal health data, access control, hardware, software, security, ease of use and cost—as summarized in the following paragraphs.

The invention provides a printed structured summary of the owner's health history ("health view") that is instantly eye readable and displays all the data that are stored on the computer readable storage device of the package, organized in clinically relevant clusters in a compact form. It enables all caregivers at all points of care to have instantly a clear integrated view of all the health problems of the owner.

The invention provides a data recording form, which enables caregivers to write by pen or pencil health data of the owner, in a structured form as an intermediate step, when they do not want or cannot use a personal computer due to any cause or reason, and in the absence of a personal computer at the point of care.

The invention enables to print new blank data recording forms and a new updated structured summary of the owner's health history, at any time anywhere in the world, with any standard printer connected to any standard personal computer. It can also, print any part of the data that are stored electronically on the portable computer readable storage device, organized by body organ systems and types and subtypes of data, in a compact manner that is instantaneously eye-readable.

The package provides a preprinted paper label already affixed to the surface of the computer readable storage device, for sticking a picture of the owner and for recording personal identification data of the owner such as name, ID number, telephone number and signature, that can eliminate mistakes in identifying the owner.

The invention provides a software program that uses in all of its standard functions only the RAM of a PC, which cannot store information after the electricity has been turned off, even for a fraction of a second. Therefore, the system does not leave any personal data of the owner in the computer of the user of the system.

The invention does not demand to install the software before using the system. It contains the complete application software program on a portable computer readable storage device, ready for use instantly with any PC, anywhere in the world.

The invention does not demand investments in hardware to use the system anywhere. It is usable with any existing standard personal computer with a standard 3.5 inch floppy drive and a printer, which are available almost everywhere—without any additional hardware or communication infrastructure.

The new system works fast even with very old computers that have very slow processors, and do not have a hard disk, because both the database management software program and the owner's personal database file are resident on the portable computer readable storage device during the operation of the system.

The invention enables making one or more backup copies of all the components of the package at all points of care and anywhere else, ready for immediate use, and thus prevents the serious problems that are created when the original copy is lost, damaged, or stolen.

The invention enables direct entry of all data elements by all caregivers, in one uniform standard simple method, and thus can improve the accuracy of the information and reduce errors and misinterpretations of data. The method enables to record each data element within seconds.

The invention works with data from all medical fields and specialties, with no exception. It eliminates the need to customize the methods of data recording and display to meet the needs of each department and individuals' needs and interests.

The invention enables to add, edit, update, re-organize, browse, search, display and print in an organized form all the personal health data of the owner, from birth to death, collected from all medical records, and all other sources of information, including personal informal paper based notes, verbal communications, phone calls and e-mails.

The invention enables every caregiver with no exception to record all findings, tests, diagnoses, therapies and any other health data, in his own professional language and all complaints of the owner and any other information provided by him, in the owner's own words. Thus, it eliminates the risks of errors in diagnoses and therapies associated with use of controlled vocabularies.

The invention enables every caregiver to record exact time, as well as temporal uncertainty and multiple temporal granularities, for each and every data element, even if it cannot fit into any standard "valid" date field. It prevents entering inaccurate and even false dates, which are often due to the use of predefined date-fields to record time in computer based systems.

The invention enables to link and integrate all health data of the owner from all sources, even if the owner is registered in each of them under a different name or ID number, due to typing errors, marriage, divorce or use of pseudonyms.

The system clusters, organizes and presents entered data elements instantly and automatically. It does not demand any order or sequence in data entry, in order to get the data presented in clinically relevant clusters. Well-defined data elements as well as puzzling unexplained data elements that are related to each other, are displayed in clinically relevant groups, in a clear, concise layout.

The invention enables caregivers to quickly review all or any part of the data, from the past health history of the owner, before proceeding with the anamnesis and examination and prior to making any decision on further tests, procedures and treatments. It provides a simple and rapid searching method, which enables caregivers to find single and groups of data elements and to gain an overview of data by specialty, within seconds.

The invention enables caregivers selected by the owner, to view on a screen of a personal computer and/or print parts of the data that they need to perform their task, usually with one click of a button, in a clear, concise, clinically relevant organized layout, which can support their diagnostic and management decisions.

The invention can save caregivers enormous amounts of time by enabling them to see the owner without waiting for the paper medical record to be transported from either the paper record archive ("record room") or from any other location to the point of care. It can improve productivity of caregivers. It can save time and money by reducing number of paper chart pulls.

The invention negates the dependency of caregivers on receiving discharge summaries from hospitals by regular mail or by fax. It precludes the loss of time, effort, cost and risks of getting the medical history of the owner by telephone. It precludes the risks of getting the medical history of the owner by E-mail.

The invention can save caregivers enormous amounts of time and effort by preventing recollecting data from the patient and from multiple paper based records, computer based medical records and documents, in every health encounter and repeatedly organizing the same data.

The invention can prevent the need of caregivers to spend time and effort in comparing disparate, inconsistent and contradictory data of the health history of the owner, collected from multiple paper based and computer based health records and documents, and trying to decide which are accurate and reliable.

The invention can prevent the loss of time, effort, inconvenience and waste of enormous amounts of money by patients and insurers on repetitions of unnecessary tests and procedures and on unnecessary hospitalizations, due to absence of all the relevant data from the past medical history of patients at the point of care.

The invention can prevent critical delays in diagnosis and treatment, abrupt discontinuation of essential drugs, adverse drug events and erroneous and harmful treatments, and even and avoid the unnecessary loss of life due to unavailability of essential data in emergency situations.

The invention enables sharing all the health data of the owner among all caregivers that are directly involved in his care in primary, secondary and tertiary care facilities. This can improve the communication and cooperation among all caregivers of the owner anywhere and enables continuity of care in an uninterrupted and coordinated manner, at all points of care.

The invention can reduce or even eliminate the need to write detailed descriptions of the past medical history of the owner in discharge summaries and referral letters by attaching it's printouts to short letters. It can also, improve the quality and decrease effort and cost of writing and dictating letters and other documents.

The new invention gives the owner absolute control on the availability, completeness, accuracy, integrity, privacy, confidentiality, security, backups and access to his personal health data that are stored on the package, and on the security of the portable computer readable device and the software that is stored on it.

The invention enables the owner to allow caregivers that are directly involved in his care, instant access to all his health data that are stored on the package in computer readable and eye readable forms, while preventing access or restricting access of others only to specific data, based on their specific roles.

The invention enables the owner to have two or more packages. For example, one for his psychiatric and/or sexual problems, one for his heart problems and one or more additional packages for his other health problems. The owner's caregiver can link and integrate data from two or more packages at any time.

The invention enables the owner to maintain absolute anonymity. One or all of the personally identifying data can be changed or removed completely by the owner on all or any one of the components of the package, whenever the owner wants, within seconds anywhere.

The invention enables the owner to view all his personal health data that are stored on the package, gain understanding of his own health status, enhance the owner's compliance with his caregivers' instructions and allow him to become a full participant in his care. It can improve the communication between the owner and his caregivers.

The invention enables the owner to ensure that his caregivers will correct inaccurate data and add missing data, but prevents him from unnoticed adding, changing or erasing data by himself. Only caregivers record data. This contributes to the reliability and trustworthiness of the data.

The invention enables the owner to make decisions about his health care. It gives the owner the freedom to change his caregiver or get a second opinion consultation or a specialist's advice anywhere in the world, for confirmation of a diagnosis or treatment, without the agreement of his primary caregivers.

The invention enables consultants in all medical fields and specialties, with no exception anywhere in the world, to use all or any part of the data that are stored on the package to make timely, well-informed and efficient decisions about the owner's health problem(s).

Use of the invention does not interfere with the communication and interactions between the caregiver and the patient during an encounter. It does not demand any change in the organization of documents in health records or in the organization of data layout in health documents and thus enables caregivers to focus on the health problems presented at the encounter.

The invention can function everywhere: in all hospitals, all primary care clinics, all private physicians' offices, all emergency sites (e.g. at the home of a person or at the point of an accident, in the middle of a street), all nursing homes and all other points of care, with no exception.

The cost of manufacturing a complete package, according to the preferred embodiment of the invention is very low, since the computer readable storage device is the regular low cost ubiquitous 3.5 inch floppy diskette and the reader/writer is the ubiquitous floppy disk drive. It is also, very simple and easy to manufacture the package anywhere, without any special equipment.

The invention is very easy to learn within few minutes anywhere with no exception. It enables caregivers to obtain hands-on self-training with blank packages, at their convenience during non-patient care hours. Few simple screens enable all caregivers to carry out all its functions.

The invention is very easy to use. The system boots up automatically and displays the main menu screen, when the computer readable device is inserted into the reader/writer and the user types a one-character command and presses the Enter key of the keyboard. It provides few straightforward options on each screen.

The invention does not demand local organizational change to use the system. It does not interfere with any local policies and procedures for protecting security, privacy and confidentiality of health information. It does not demand any change in the way caregivers work, and does not interfere with their routines.

The package carries the owner's health data, but is not a health or medical record, and thus is not bound by any regulations or laws relevant to health records. Therefore, it can be used by all health care professionals, at all points of care anywhere in the world without legal delays.

The invention can be used by clinicians to extract, organize, display and print health data collected from paper based and computer based textbooks and/or medical journals, in a clear, concise, clinically relevant organized layout, which can help studying the medical literature.

In addition, the system of the present invention includes the following further advantages:

It can convey instantly all relevant health information at all points of care to all caregivers, when the owner cannot do so.

It can quicken and improve the quality of triage decisions at all points of care anywhere in the world.

It enables to exploit the rich information contained in medical narratives extracted from text of health documents.

It can be used for organizing, searching, and displaying electronically data that are stored in conventional paper based health records.

It enables to make real the patient's ownership of his data, while allowing the caregiver keep the original health records and documents.

It gives the users immediate benefit, by instantly organizing and presenting entered data elements by problems in a clear, concise layout.

It can be used as a powerful teaching tool in all subspecialties of human and veterinary medicine for students and graduated clinicians alike.

These and further and other objects, features and advantages of the invention will become apparent from consideration of the disclosure, which includes the above and ongoing written description of the specification, with the claims and the drawings.

BRIEF DESCRIPTION OF THE DRAWINGS

FIG. 2 is an example of prompting during the "make a backup" process.

FIG. 3 is an example of a first screen display of "browse-edit data" screen (with help).

FIG. 3a is the same help tool bar as in FIG. 3.

FIG. 4 is an example of a first screen display of "browse-edit data" screen (without help).

FIG. 5, as shown in FIG. 4, further shows an example of options (Bottom selected).

FIG. 6 is an example of a last screen display of "browse-edit data" screen (without help) and options (Top selected).

FIG. 7, as shown in FIG. 4, further shows an example of options (Lock selected).

FIG. 8 is an example of a first screen display of "browse-edit data" screen (columns 1-5 locked+column 10 after column 5).

FIG. 9 is an example of a first screen display of "browse-edit data" screen (columns 1-4 locked+column 7-9 after column 4).

FIG. 10, as shown in FIG. 4, further shows an example of options (Record No. 19 selected).

FIG. 11 is an example of a display of "browse-edit data" screen (with record 19 on top).

FIG. 12, as shown in FIG. 4, further shows an example of options (Freeze Date selected).

FIG. 13, as shown in FIG. 4, further shows an example of options (Find MET selected).

FIG. 14 is an example of a display of "browse-edit data" screen (with first MET SYS on top).

FIG. 16 is an example of a screen display of the musculoskeletal system (option "13. MUS" was selected).

FIG. 17 is an example of a screen display of the skin system (option "17. SKN" was selected).

FIG. 19 is an example of a screen display of family history (option "1. FAMILY HISTORY" was selected).

FIG. 20 is an example of a screen display of signs and symptoms (option "2. SIGNS & SYMPTOMS" was selected).

FIG. 21 is an example of a screen display of laboratory and other tests (option "3. LABS & TESTS" was selected).

FIG. 22 is an example of a screen display of diagnoses (option "4. DIAGNOSES" was selected).

FIG. 23 is an example of a screen display of all treatments (option "5. ALL TREATMENTS" was selected).

FIG. 24 is an example of a screen display of tablets only (option "6. TABLETS (only)" was selected).

FIG. 25 is an example of a screen display of blood tests (option "7. BLOOD TESTS" was selected).

FIG. 27 is an example of a screen display of all X-ray examinations (SUB=XRS).

FIG. 28 is an example of a "search & display" screen for SUB=PEX.

FIG. 29 is an example of a screen display of all findings in physical examinations (SUB=PEX).

FIG. 30 is an example of a "search & display" screen for DATA=CHEST PAIN.

FIG. 31 is an example of a screen display of all chest pain events (DATA=CHEST PAIN).

FIG. 33 is an example of a vertical ADD NEW DATA screen (without help).

FIG. 34 is an example of a horizontal "add new records?" prompt at end of file.

FIG. 35 is an example of a horizontal "add new records" screen at end of file.

FIG. 36b shows incomplete entries. FIG. 36c shows question prompts for completing entries. FIG. 36d shows a screen with completed entries.

FIG. 37 is an example of a HEALTH VIEW of a patient for 1995-2000.

FIG. 38 is an example of a HEALTH VIEW of the same patient for 1-6/2001.

FIG. 39 is an example of a HEALTH VIEW of the same patient for 1995-6/2001.

FIG. 40 is an example of a BLANK FORM.

FIG. 41 is an example of a database structure.

FIG. 42 is an example of data elements in order of recording (1,2,3 . . . 62).

FIG. 43 is an example of data elements in organized order (63, 61, 62, 57, 58.60, 8, 6 . . . 46).

FIG. 43a-43d are examples of data shown in FIG. 43, presented as a printed HEALTH VIEW FIGS. 44, 44a and 44b are examples of a chapter on Pellagra in a textbook.

FIGS. 45 and 45a show data extracted form the text of FIGS. 44, 44a and 44b organized by the present invention.

DETAILED DESCRIPTION OF THE INVENTION

Figure 1:
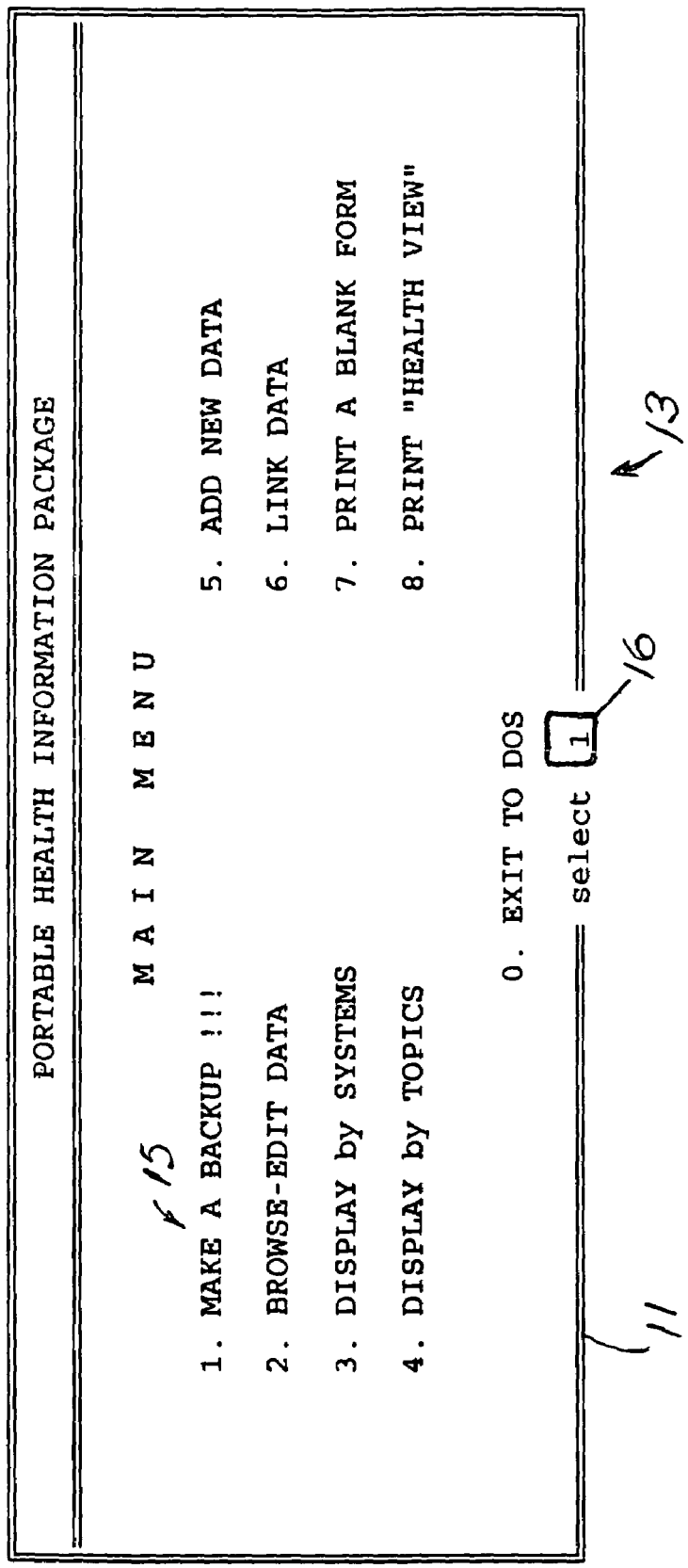
FIG. 1 is an example of a main menu screen.

The preferred portable personal health information package provides a method for handling personal health data, that enables instant access to the full, complete, accurate and up-to-date health information of the owner or any part of it, whenever the information is needed, at all times, at all points of care anywhere in the world, for all health care professionals, in computer readable and eye readable forms. The package comprises a database management software program and a personal database file, which are contained in a portable computer readable storage device, a data recording form, and a health view printout. The database management software program is resident on the portable computer readable storage device during its operation, and uses only the RAM of a PC, but does not use the hard disk in all of its standard functions. The database management software program enables the user of the system to record, update, link, integrate and display health data of the owner from birth to death, collected from all paper based medical records, computer based medical records, and all other sources of information, including personal informal paper based notes, verbal communications, phone calls and e-mails. It enables the system to record and store electronically each health data element directly onto the portable computer readable storage device, as one record in the personal database file of the database management software program and also allows browsing, adding, editing, searching, displaying and printing in an orderly fashion all or any part of the health data of the owner, and the health view printout. The data recording form enables a user to write by hand onto paper each health data element in one compact, simple, universal, standard structure. This can be done as an intermediate step, when a caregiver does not want, or cannot use a personal computer at the point of care to record and store the data directly on the computer readable storage device. The health view printout is a structured summary of the owner's health history, and displays all the data that are stored electronically on the portable computer readable storage device, organized by body organ systems and types and subtypes of data, on paper in a compact manner that is instantaneously eye-readable. The package contains a preprinted paper label already affixed to the surface of the computer readable storage device, for holding a photographic image of the owner and for recording identification data of the owner such as name, ID number, telephone number and signature, that can eliminate mistakes in identifying the owner. The invention operates with any existing standard personal computer anywhere, and can use a variety of portable programmable detachable computer readable devices, that can store and carry the personal database file and the database management software program, including optical memory cards, floppy disks, flash memory cards, PCMCIA cards and other computer readable storage devices with comparable storage capacity. The preferred embodiment uses a conventional 3.5 inch floppy disk as a portable computer readable storage device, since it is ubiquitous, cheap and uses the ubiquitous 3.5 disk drive of any type of personal computer as a reader/writer. The cost of a complete package, in which the computer readable storage device is a 3.5 inch floppy disk, is minimal. The package is intended to be carried by a person at all times, so as to be available for use to all health care providers at all points of care, and thus reduces the cost and improves the quality of health care. The owner has absolute control over the availability, completeness, accuracy, integrity, privacy, confidentiality, security and access to his health data that are stored on the package. While the preferred embodiment of the invention is recording, storing, organizing, displaying and printing health data of human beings, it can also be used for health data of animals. Alternative embodiments include variations of the invention for storage and retrieval of other types of data, such as machine maintenance data, and a variety of personal data such as, curriculum vitae, addresses and telephone numbers, birthdays, anniversaries etc. The cost of manufacturing a complete package, in which the computer readable storage device is a 3.5 inch floppy disk, is minimal.

A detailed description of the invention will be more readily understood by reference to the accompanying drawings.

FIG. 1 shows a "MAIN MENU" screen 13, which appears after inserting the computer readable device into the appropriate reader/writer, typing a command and pressing the Return or Enter key of the keyboard. A main menu 11 is shown on a computer screen 13, with options 15 for selecting 16 from main menu. Keying in selecting position 16 a number associated with an option and pressing the Enter key of the keyboard selects that option.

FIG. 2 shows a screen 17 with questions 18, 20, 21 to be answered and instructions 19 to follow, for making a backup copy of the device. This screen 17 also enables labeling the device electronically, and changing or deleting the electronic label at any time.

FIG. 3 shows a screen 23 displayed after selecting 16 the option "2. BROWSE-EDIT DATA" from the main menu 11 in FIG. 1. This screen 23 allows the user to scroll through the database horizontally and vertically, and edit and add records. Use of this screen 23 also enables editing data elements and marking data elements for deletion. The help tool bar 25 is shown at the top. The first screen 23 of the owner's health history 27 is displayed. The data elements 29 are numbered according to numbers of problems 31 in human body systems 33. A specific label marks each body system 33. CVS 32 means cardiovascular system. Question marks ("???") 34 mean that the body system 33 to which the particular data element belongs is unknown. Data elements 35 of the health history are presented. In the column headings, SQ 37 stands for sequence of data elements within a topic. The dates of occurrence are listed in columns 41.

FIG. 3a shows the help tool bar 25 shown at the top of FIG. 3, which provides assistance on how to browse and navigate the cursor, move up and down in the database, mark for deletion individual fields and records and also set a variety of additional options.

FIG. 4 shows the same screen 23 as FIG. 3 without the help tool bar 25 (FIG. 3) and with more data elements 29 displayed. The name, address and birth date of the owner are shown on the line 42 under the heading.

FIG. 5 shows the same screen 23 as FIG. 4 with an optional control tool bar 43, which permits rapid locating of records or locking. Option 44 "Bottom" is selected, which switches to the last record of the owner's health history, as shown at the bottom of FIG. 6.

FIG. 6 shows the last screen 23a of the owner's health history 23 of FIG. 5 showing more data elements 29. The last record 29a of the owner's health history is shown at the bottom. Option "Top" 52 is selected, which switches the display to the first record of the owner's health history, which is shown at the top of FIG. 5.

FIG. 7 is the same screen 23 as FIG. 5, with the option control tool bar 45 requesting a particular number of columns to lock to the left of the screen, even when the user pans to the right using the appropriate navigation keys on the keyboard of his PC.

FIG. 8 shows a screen 47 similar to screen 23 in FIG. 5, with five left columns locked and sixth last column 49 indicating sources of data elements 29. Ten columns are provided. Less than ten are displayed at any time.

FIG. 9 shows screen 50 similar to FIG. 5, with the six left columns locked, and an additional seventh column 51 ("TIME") displaying time of day of occurrences.

FIG. 10 shows a screen 23 with a control bar. Selecting "Record No." 54 presents box 53 for requesting a particular record number (19) entered in space 56.

FIG. 11 shows a screen 55 displaying a selected record 57 and sequential records.

FIG. 12 shows a screen 23 with the option control tool box 61 appearing by selecting freeze 59, requesting to freeze a particular field ("DATE"). A caregiver inserts what field to freeze, and the software locks the selected field for easier editing of the same field in all records.

FIG. 13 shows the screen 23 with "Find" 63 selected to display the option control tool box 65, requesting to find and quickly move the highlighting to a particularly selected body system "MET" (metabolic) 64.

FIG. 14 shows the screen 67 showing organized entries, starting with the first metabolic MET 66 data element. The MET (metabolic) data elements 29 are followed with data elements related to another body system MUS 68 (musculoskeletal).

Figure 15:
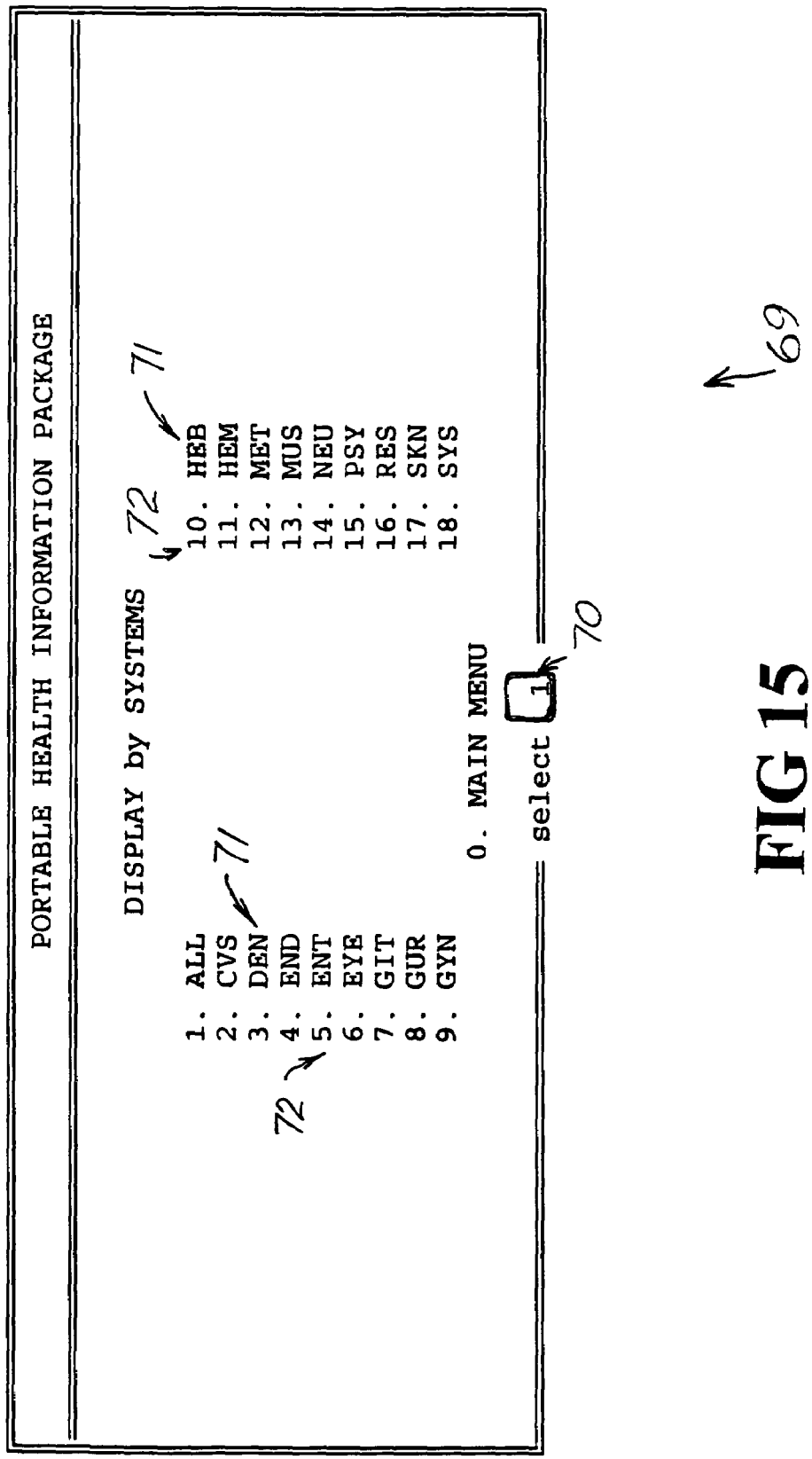
FIG. 15 is an example of a "display by systems" menu.

FIG. 15 is a "DISPLAY by SYSTEMS" menu screen 69, which shows the systems 71 available for selecting by inserting a number in space 70. Keying a number 72 associated with a system 71 selects and displays that system. The menu screen 69 was selected by keying 3 in space 16 on main screen 13, as shown in FIG. 1.

FIG. 16 shows screen 73 in which the caregiver has selected MUS 75 (musculoskeletal) by keying the number 13 in space 70 while screen 69 (FIG. 15) is displayed.

FIG. 17 shows a screen 77 in which 17 SKN (skin) 79 has been selected from the screen shown in FIG. 15.

Figure 18:
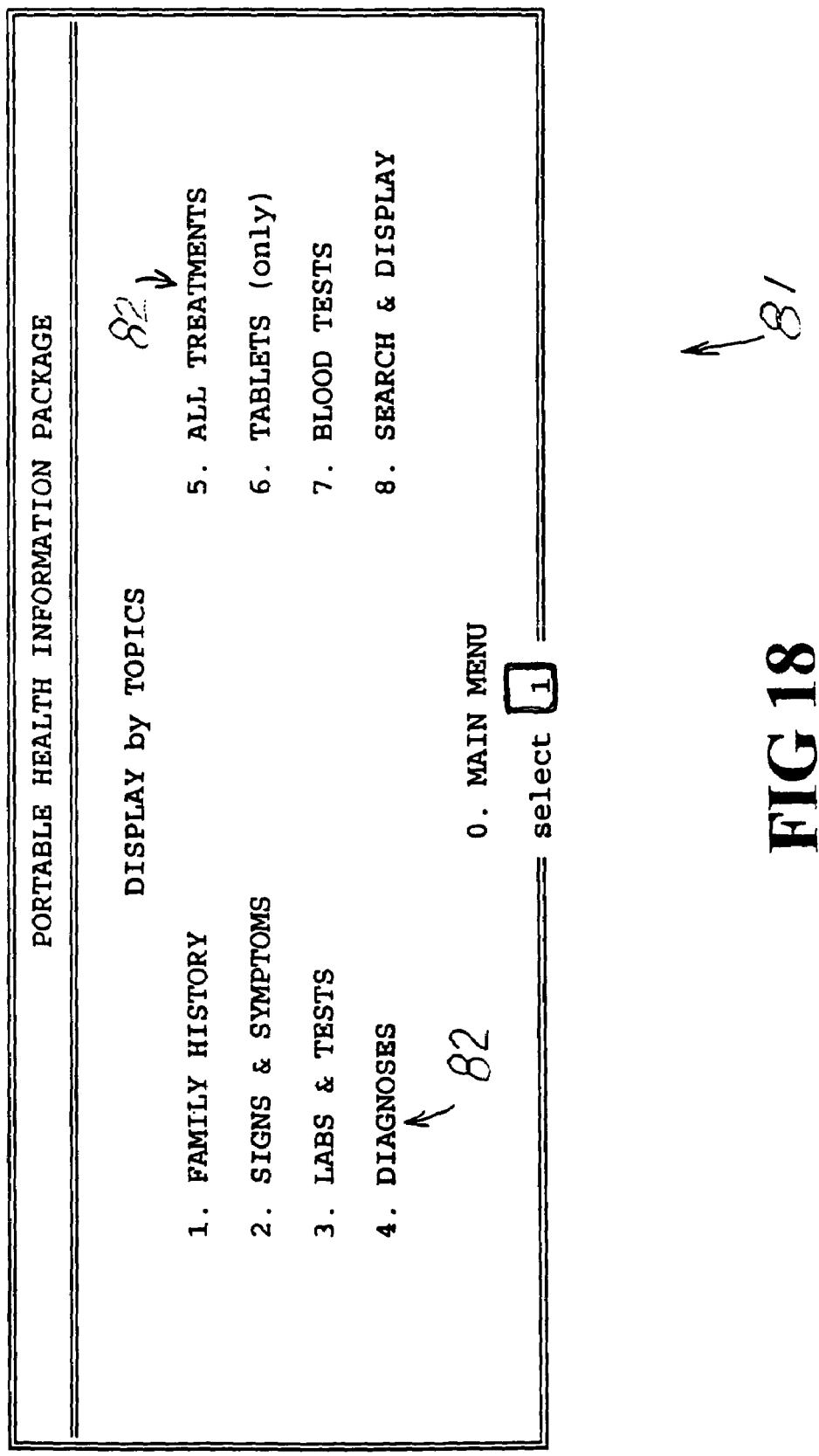
FIG. 18 is an example of a "display by topics" menu.

FIG. 18 shows a screen 81, which appears when option 4, "Display by Topics", is selected from the main menu 11 of screen 13 in FIG. 1. Topics 82 are available for selection.

FIG. 19 shows a screen 83, which appears when the option 1, Family History, is selected from the topics screen 81 shown in FIG. 18. The letter "f" 84 in the third column denotes family history.

FIG. 20 shows a screen 85, which appears when the option 2, Signs and Symptoms, is selected from the topics screen 81 shown in FIG. 18. The letter "s" 86 in the third column denotes signs and symptoms.

FIG. 21 shows a screen 87, which appears when option 3, Labs and Tests, is selected from the topics screen 81 shown in FIG. 18. The letter "l" 88 in the third column denotes laboratory and test results.

FIG. 22 shows a screen 89, which appears when option 4, Diagnoses, is selected from the topics screen 81 shown in FIG. 18. The letter "d" 90 in the third column denotes diagnoses.

FIG. 23 shows a screen 91, which appears when option 5, All Treatments, is selected from the topics screen 81 shown in FIG. 18. The letter "t" 92 in the third column denotes treatments.

FIG. 24 shows a screen 93, which appears when option 6, Tablets (only), is selected from the topics screen 81 shown in FIG. 18. The letters "tab" 94 in the sixth column denote tablets.

FIG. 25 shows a screen 95, which appears when option 7, Blood Tests, is selected from the topics screen 81 shown in FIG. 18. The letters "bld" 102 in column 6 denote blood tests.

Figure 26A:
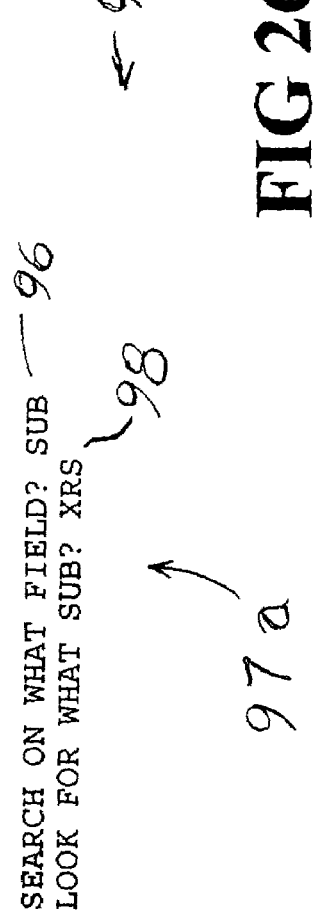
FIGS. 26 and 26a are examples of a search & display screens for selecting SUB=XRS.
Figure 26:

FIG. 26 shows a screen 97 when option 8, "SEARCH & DISPLAY", is selected from the "DISPLAY by TOPICS" screen 81 shown in FIG. 18. Screen 97 provides dialog prompts 97a for selecting specific data elements in specific fields, as shown on screen 97 in FIG. 26a, in which the field SUB (subject) 96 and XRS (x-rays) 98 have been selected in response to the prompts 97a.

FIG. 27 shows screen 99, which appears in response to the selections shown on screen 97 in FIG. 26, which displays the findings in all XRS (x-rays) 98 in column 5, from all body systems 100 in the first colum.

FIG. 28 shows a screen 101 similar to that shown in FIGS. 26 and 26a in which the field SUB (subject) 103 and PEX (physical examination) 105 have been selected.

FIG. 29 shows screen 107, which is displayed when SUB and PEX have been selected on screen 101. All entries of physical examinations 105 from all body systems 100 are shown grouped together.

FIG. 30 is a screen 109 similar to those shown in FIGS. 26 and 28, in which the DATA field 111 and CHEST PAIN 113 have been selected.

FIG. 31 shows a subsequent screen 115, which shows entries 117 of chest pain as selected by screen 109.

Figure 32:
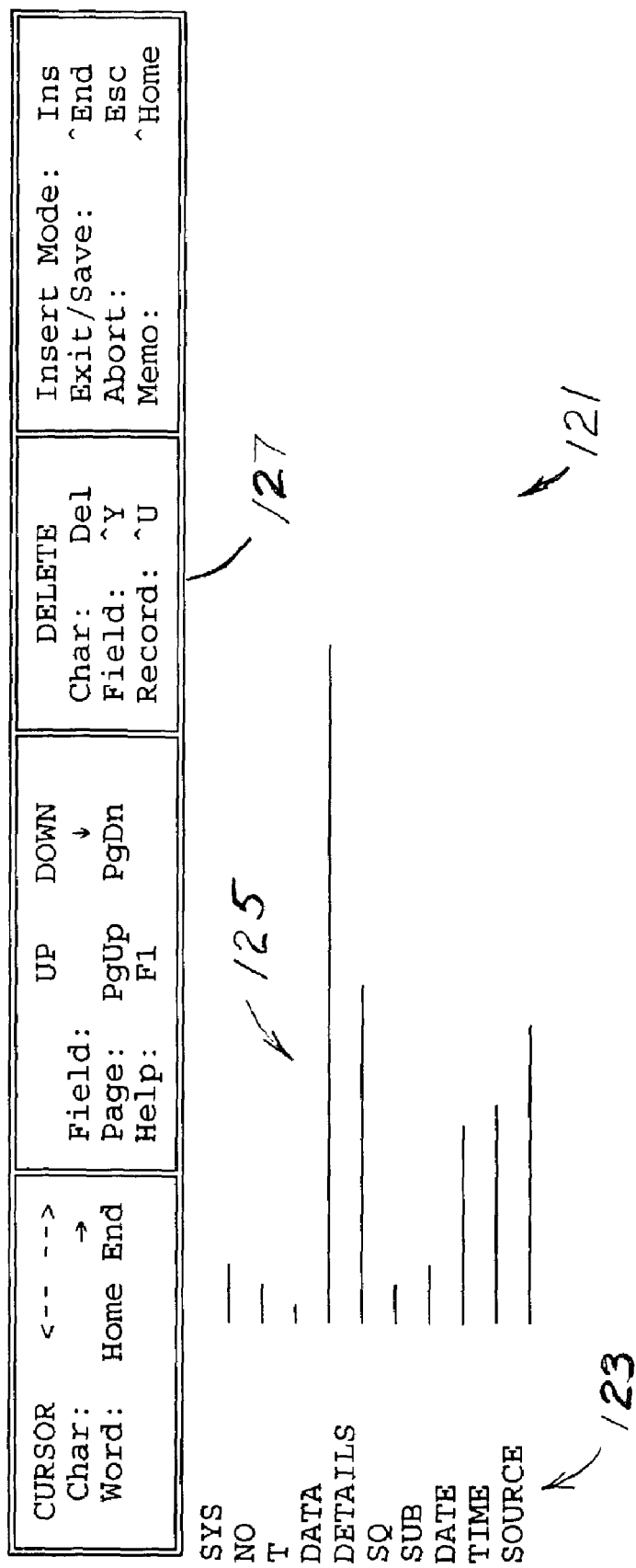
FIG. 32 is an example of a vertical ADD NEW DATA screen (with help).

FIG. 32 shows a screen 121, which is displayed when option 5, ("ADD NEW DATA"), has been selected from main menu 11 on screen 13 in FIG. 1. Screen 121 has prompts 123 for filling in new data. The lines 125 provide the limit lengths of the new data entries. The help tool bar 127 is shown at the top. Once filled in completely, the new data on the screen 121 is entered by pressing the ENTER on the PC keyboard, and a new screen 121, is displayed for filling in more new data.

FIG. 33 shows a screen 131, which is the same as FIG. 32 without the help tool bar. The number of the entry "NO" 128 denotes number of problem in body system SYS 129.

FIG. 34 shows a screen 133 with entries, which are displayed when the user browses down to the end of entries in FIG. 4, by pressing the "down" arrow of the PC keyboard. This screen prompts the user "Add new records? (Y/N)". If the user answers "Y" in space 137, a screen 141 appears with a blank bottom line 143, as shown in FIG. 35. The user adds a new record in the spaces 145 provided. As soon as the "ENTER" key of the keyboard is pressed, a new blank bottom line 143 appears for adding another record, and the cursor 135 jumps to a position at the beginning of the three-letter SYS field, column one, for labeling the system to which the new data element belongs.

Figures 36, 36A:
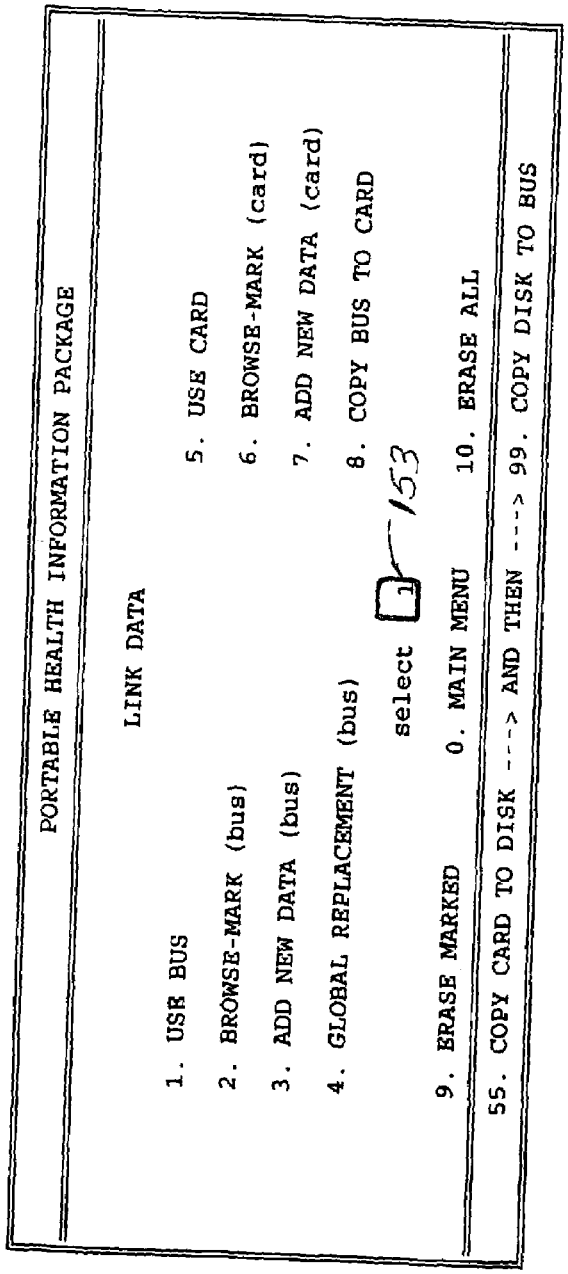
FIG. 36 is an example of a LINK DATA screen.
FIG. 36a is an example of prompting during the "GLOBAL REPLACEMENT (bus)" process.

FIG. 36 shows screen 151, which appears when option "6. Link Data" is selected from the main menu 11 on screen 13 shown in FIG. 1, and which is used to link and integrate data from two computer readable devices in cases in which one person has two (or more) computer readable devices. That may happen, for instance, when a patient is treated without having his old permanent device, and a caregiver gives him a new temporary personal health information package. The owner may also decide to have two (or more) computer readable devices and printed overviews—one computer readable device and health view for his very sensitive data, such as his psychiatric and/or sexual problems and another computer readable device and health view for his other health problems. In this way he can ensure that his dentist or ophthalmologist will not have access to information on his psychiatric or sexual problems, both in the computer readable display and on printouts. The owner may decide to link and integrate data from the two (or more) computer readable devices at any time. Screen 151 can also be used for browsing, adding and editing data elements on a bus file and on the permanent database file, for global replacement of fields in all data elements on the "bus file", as well as for erasing individual data elements in the "bus file" and on the "permanent data file".

Linking and integrating data from an old device and a new device is performed in a few steps:

Step 1: One of the devices (the old or the new) is inserted into the slot of the reader/writer, followed by pressing the ENTER key on the PC keyboard.

Step 2: When the "MAIN MENU" screen 13 of FIG. 1 appears, the option "LINK DATA" "is selected by typing the appropriate number, 6, in space 16 and pressing the ENTER key.

Step 3: When the "LINK DATA" screen 151 (FIG. 36) appears, the option "COPY CARD TO DISK" is selected by typing the appropriate number, 55, in space 153 and then pressing the ENTER key. That creates a temporary copy of the data file on the hard disk of the PC.

Step 4: From screen 151 of FIG. 36, the option "MAIN MENU" is selected by typing the appropriate number, 0, on the keyboard and pressing the ENTER key, which causes the display of main menu 11 screen 13 of FIG. 1.

Step 5: From the MAIN MENU screen 13 of FIG. 1, the keying of option 0, "EXIT TO DOS", is selected, which is followed by the appearance of the DOS prompt.

Step 6: The computer readable storage device is ejected from the reader/writer by pressing the "device ejection" button of the reader/writer.

Step 7: Steps 1 and 2 are performed with the second device.

Step 8: When the "LINK DATA" screen 151 of FIG. 36 appears, the option, 99, "COPY DISK TO BUS", is selected by typing the appropriate number, 99, and pressing the ENTER key. This initiates two consecutive actions: The temporary copy of the first data file that was created on the hard disk of the PC in Step 3, is copied from the hard disk of the PC to a temporary bus file on the second device. The copy of the data file that was created on the hard disk of the PC in Step 3 is erased.

Step 9: The option, 8, "COPY BUS TO CARD" is selected by typing the appropriate number, 8, and pressing the ENTER key. This initiates instant linkage and integration of all the data elements from the old device and the new device into one data file.

Step 10: Selecting the option 6, ("BROWSE-MARK (card)"), shows that all the data from the two devices are integrated, so that data that are related to each other, that were originally recorded on two devices, are grouped together by body organ systems, problems, types and subtypes on the second device.

Step 11: Selecting option 1, ("1.USE BUS"), and then selecting option 10, "ERASE ALL", by typing the appropriate number and pressing the ENTER key, cleans the bus file from data.

Step 12: From screen 151 of FIG. 36, the option 0, "MAIN MENU", is selected by typing the appropriate number, 0, and pressing the ENTER key, which causes the display of screen 13 of FIG. 1.

Step 13: When the PC is connected to a printer, selecting the option 8, "PRINT HEALTH VIEW", from the main menu screen 13 of FIG. 1, will print an updated integrated summary of all the data that were recorded on both the first device and the second device.

Step 14: Selecting the option 1, "MAKE A BACKUP", from the main menu screen 13 of FIG. 1 initiates creating an identical copy of the integrated device. If the first device is inserted into the reader/writer during the backup process, it will become an identical copy of the second (integrated) device, and thus both the first device and the second device will contain all the data from the two devices.

Selecting the option 2, "BROWSE-MARK (bus)", or the option 6, "BROWSE-MARK (card)", by typing the appropriate number and pressing the ENTER key, cause the display of screen 23 of FIG. 3, which enables browsing, editing data elements and marking data elements for deletion on the bus file or on the permanent file respectively. The help tool bar 25 shown at the top of screen 23 of FIG. 3 provides assistance on how to browse and navigate the cursor, move up and down in the database, mark for deletion individual fields and records and also set a variety of additional options. Browsing and editing the permanent file and the bus file is highly recommended immediately after step 8 and before step 9.

Selecting the option 4, "GLOBAL REPLACEMENT (Bus)", from screen 151 of FIG. 36 causes the display of screen 152 of FIG. 36a, which shows questions XX, YY and ZZ to be answered for replacement of the data content of a selected field in all records of the bus file, quickly in a single step. Using the global replacement function can save a caregiver the tedious, time-consuming and error prone task of retyping the three letters in the SYS field in the first column for every one of many data elements related to one specific system, that he needs to record in an encounter. For example, FIG. 36b shows a series of data elements that a physician recorded in the bus file without typing the three letters for labeling the system in the SYS field and the date of occurrence for each data element in the DATE field. FIG. 36d shows the same series of data elements of FIG. 36b, after answering the questions of FIG. 36a, requesting replacement of the blank SYS and DATE fields as shown in FIG. 36c. Then selecting the option 8, "COPY BUS TO CARD", on screen 151 shown in FIG. 36 by typing the appropriate number and pressing the ENTER key initiates instant linkage and integration, of all the data elements from the bus file and the permanent file into one data file.

Deleting individual records from the permanent and the bus database files involves two steps. In the first step, the user marks one or more specific records using the appropriate BROWSE screen according to the instructions presented in the help toolbar 25 as shown at the top of the screen 23 of FIG. 3. Permanent deletion of individual data elements, which were previously marked for deletion in the "bus file" or in the "permanent data file" is done by selecting the option 1, "USE BUS", or 5, "USE CARD", respectively from screen 151 of FIG. 36, and then selecting the option "ERASE MARKED", by typing the appropriate number, 9, and pressing the ENTER key.

Selecting the option "ERASE ALL", from screen 151 of FIG. 36, by typing the appropriate number, 10, and pressing the ENTER key, cleans the selected file from the data. Once a file is deleted, it cannot be recalled. Therefore, in order to prevent unintentional deletion of data, the user is questioned if he really wants to delete the data on the file, before this command is executed.

FIGS. 37, 38 and 39 illustrate the linkage and integration of two HEALTH VIEWs of a person that has two personal health information packages. The first (old) device screen 161 in FIG. 37 contains data for the period 1995-2000, and the second (new) device screen 163 in FIG. 38 contains data for the period 1-6/2001.

FIG. 37 shows a printed HEALTH VIEW 161, which was printed by selecting the option 8, ("PRINT HEALTH VIEW"), from main menu screen 13 of FIG. 1, using the first (old) owner's device containing data for the period 1995-2000.

FIG. 38 shows a printed HEALTH VIEW 163, which was printed by selecting the option 8, ("PRINT HEALTH VIEW"), from main menu screen 13 of FIG. 1, using the second (new) owner's device containing data for the period 1-6/2001.

FIG. 39 shows a printed HEALTH VIEW 171 that combines health views 161 and 163, which was printed by selecting the option 8, ("PRINT HEALTH VIEW"), from main menu screen 13 of FIG. 1, using the integrated device, after linking and integrating data from an old device and a new device. Health views 161, 163 and 171 list all of the entries by systems 167 and topics 169 within the systems for the specific periods.

FIG. 40 is a blank data recording form 181, which may be printed from information on the portable computer readable device by selecting the option 7, "PRINT A BLANK FORM", from the MAIN MENU 11 on screen 13 shown in FIG. 1. Data recording form 181 has spaces in columns headed SYS (system) 183, NO (number of problem in system) 185, T (topic) 187, Data 189, Details 191, SQ (sequence) 193, SUB (subject) 195 and DATE+TIME 197. A line 198 is provided at the bottom for an identification, signature and date of the person entering the information, if desired. Spaces 199 at the top provide the owner's identification and telephone number, and spaces 200 provide for recording first date and last date of occurrence of data that are recorded on the data recording form.

FIG. 41 shows screen 201, showing a database structure containing field numbers 203, field names 205, field types 207, and field widths 209. The fields are columns in the screens and printouts.

FIG. 42 shows a screen 211 or printout, which lists recorded entries 213 by chronological sequence 214 of entry of the data.

FIG. 43 shows a screen 221 that lists entries grouped in clusters according to systems 222.

FIG. 43a shows a printed HEALTH VIEW 225, in which the name, address and date of birth of the owner are displayed in the first line 226. All unexplained data are labeled with three question marks (???) 227 and are displayed clearly at the top of the screen, clustered in clinically relevant groups, by problem numbers, and thus draw the caregivers attention immediately. FIGS. 43b, 43c and 43d are continuations of the printed HEALTH VIEW shown in FIG. 43a.

FIGS. 44, 44a and 44b show an example of a chapter in a textbook 231, which describes a disease.

FIGS. 45 and 45a show a screen 233 or printout, which presents the symptoms, laboratory test results, treatments and all other relevant data elements extracted from the text shown in screen 231 of FIGS. 44 and 44a-b, grouped into systems 234 using the present invention for convenient use by a health caregiver studying the disease or for teaching the disease to students.

Figure 46:
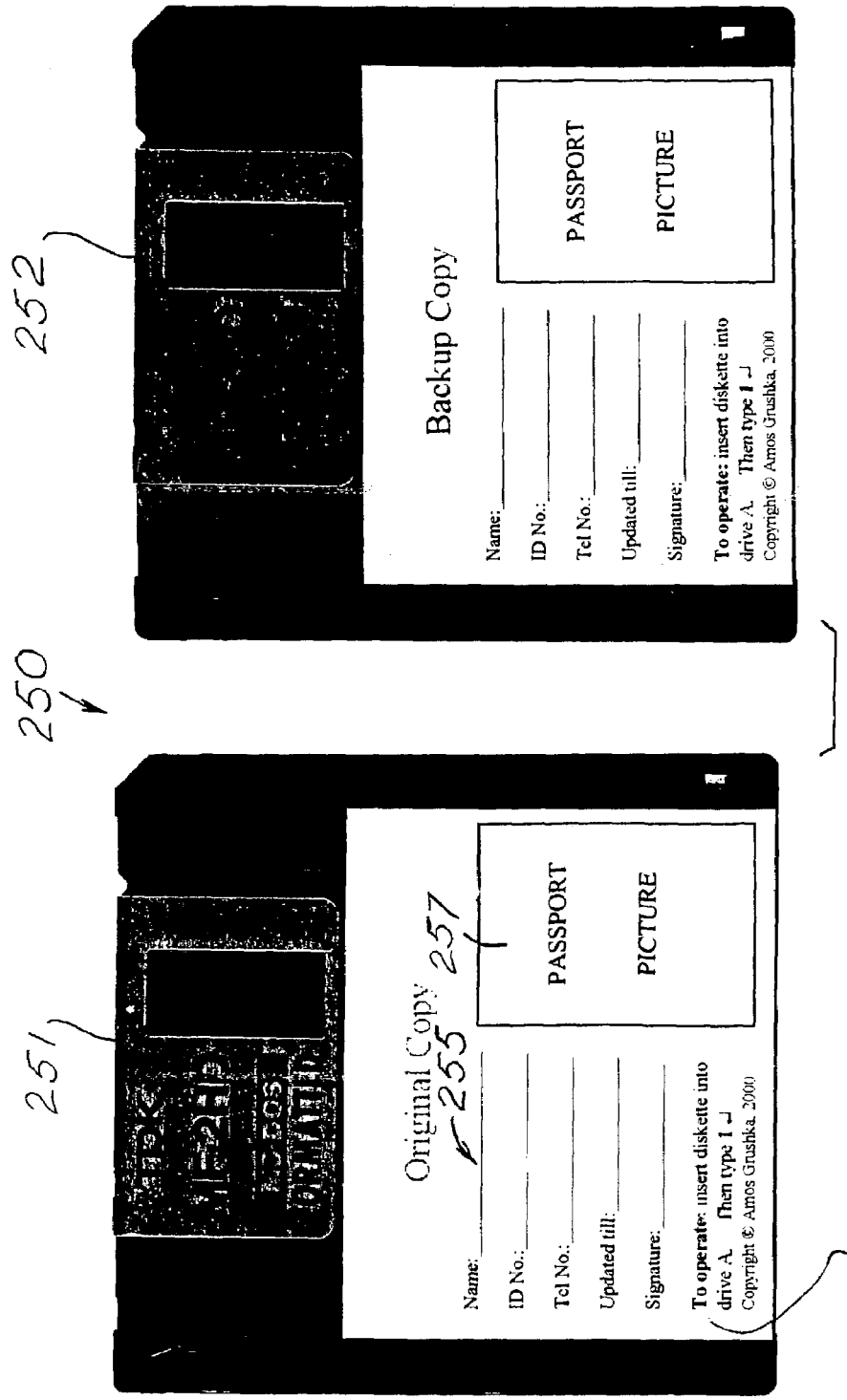
FIG. 46 is a depiction of a computer readable device 251 with complete instructions for operation.

FIG. 46 shows a system 250 on a device 251, which is a computer readable storage device. Complete and simple instructions 253 are provided on the bottom of the identification labels. The entire operation is controlled by the database management software program, which is resident on the portable computer readable storage device 251 during its operation, and uses only the random-access memory (RAM) of a PC, but does not use the hard disk or the windows operating system in all of its standard functions. Since a RAM of a PC cannot store information after the electricity has been turned off, even for a fraction of a second, the system works outside of the hard drive of a computer, leaving no permanent records in the computer. Device 251 includes all of the necessary software and instructions and includes software for printing a blank form for later use and a health view for the caregiver's use and for the owner's review. Device 252 is a backup copy of device 251. Personal data may be provided in spaces 255. A passport photo or thumbprint or any selected identifier may be provided in space 257.

Figure 47:
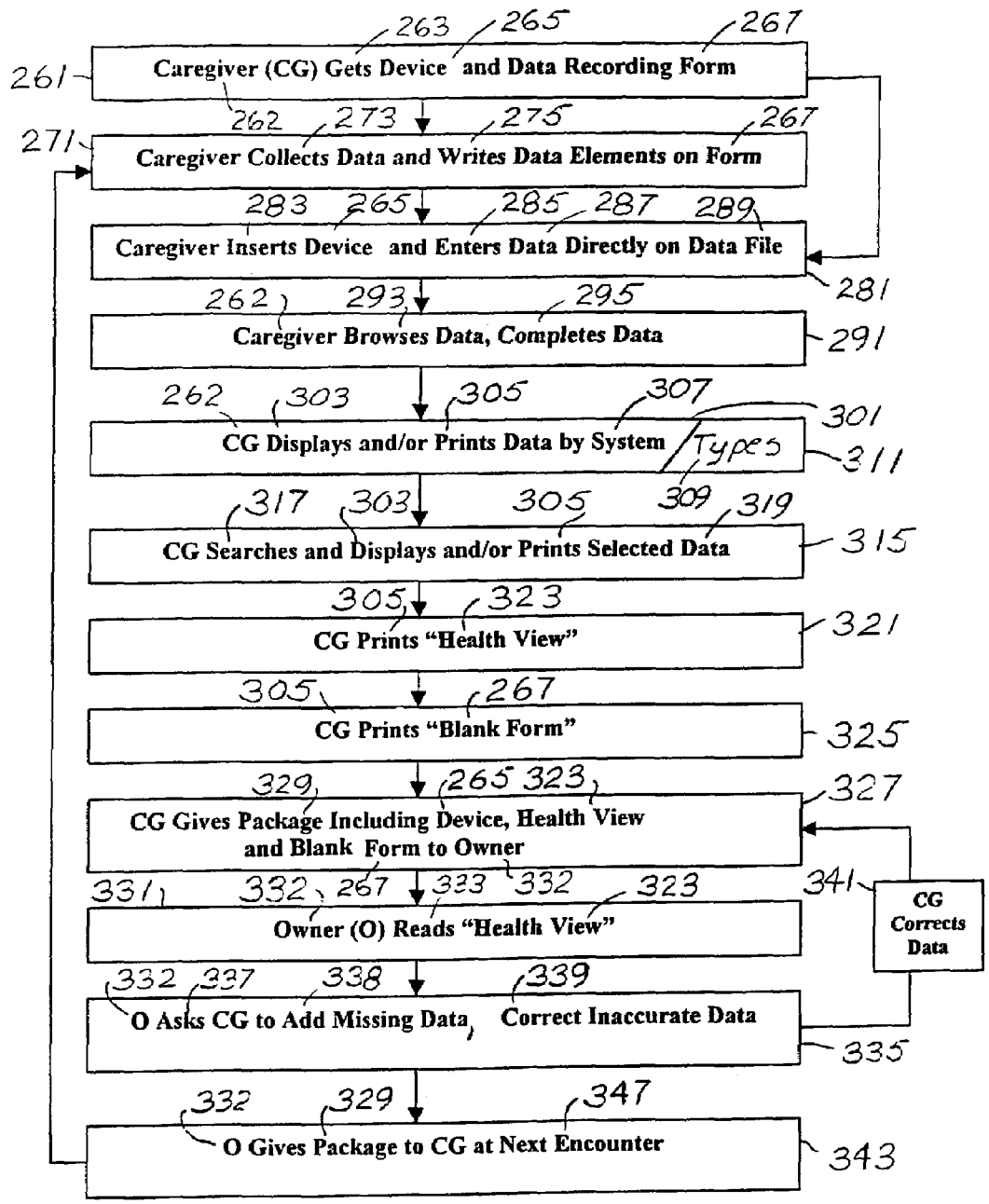
FIG. 47 is a flow-chart describing use of the system.

FIG. 47 is a flow-chart 260 showing steps of using the invention. In the first step 261 the caregiver (CG) 262 gets 263 a device 265 and gets or prints from the device inserted in a PC a data recording form 267, also called a blank form.

In the second step 271 the caregiver 262 collects 273 data and writes 275 data elements on the form 267. In the next step 281, the caregiver inserts 283 the device 265 into the reader/writer of his computer and, using the computer (PC) keyboard, enters 285 data elements 287 directly in the data file 289 in the device.

In the next step 291, the caregiver 262 browses 293 the data and completes 295 the data.

Next, in step 301 the caregiver (CG) 262 displays 303 and/or prints 305 the data by systems 307. The systems 307 in this step are the body systems 234 shown in FIG. 45, for example.

In the next step 311 the caregiver displays 303 and/or prints 305 the data by types 309, for example pain or chest pain.

Next, in step 315 the caregiver searches 317 and displays 303 and/or prints 305 selected data 319.

In step 321 the caregiver prints 305 a health view 323.

In step 325 the caregiver prints 305 a blank form 267.

In step 327 the caregiver gives a package 329 to the owner. Package 329 includes a device 265 with recorded data and software, a health view 323 and a blank form 267.

In step 331 the owner 332 reads 333 the health view 323. The owner 332 may be a person whose records are included in the health view 323 and device 265, or the owner of an animal or a flock or herd of animals whose records are included in the device 265 and health view 323.

In step 335 the owner asks 337 the caregiver to add 338 missing data or to correct 339 inaccurate data. The caregiver corrects or adds the data in step 341, and steps 327, 331 and 335 are repeated.

In step 343 the owner 332 gives the package 329 to a caregiver at the next encounter 347, which may be a scheduled or emergency visit, or a visit for laboratory work or updates. Then steps 271 and sequential are repeated.

Figure 48:
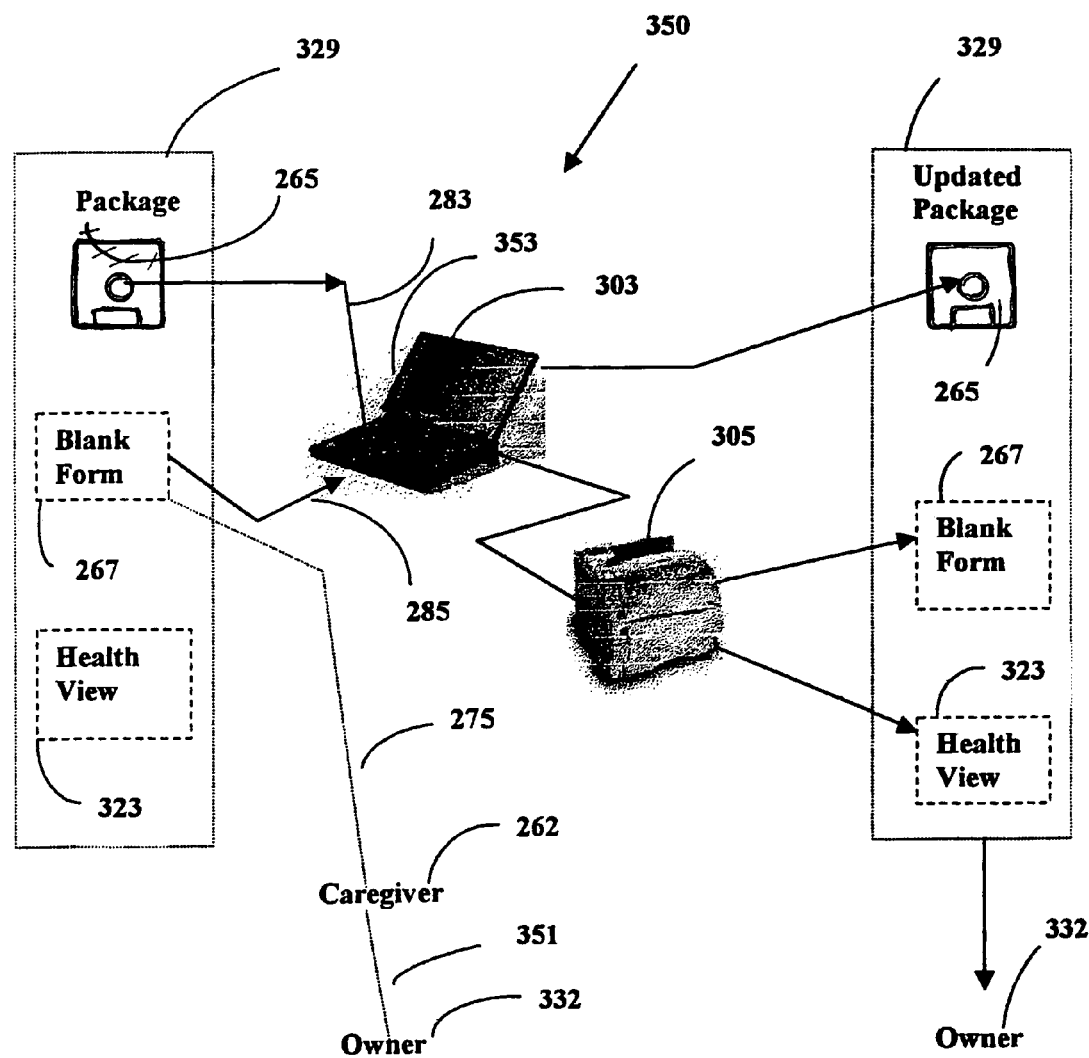
FIG. 48 schematically shows an example of using the new system.

In FIG. 48 the system 350 is shown.

A package 329, which includes a health view 323, a blank form 267 and a storage device 265, is provided by or to the caregiver 262.

In the first instance, before any use, the device 265 contains the software but no records. Usually in that case the caregiver has the device 265 and form 267.

If the system has been used previously by the owner 332, the owner gives the package 329, which includes the health view 323, to the caregiver.

This provides 351 information to the caregiver 262, who enters 275 the information on form 267. The caregiver inserts 283 the device 265 into a computer 353 and enters 285 data from the form 267 via the keyboard directly into the RAM or the computer and into the data file of the device 265. The caregiver reviews and corrects the entered data. The caregiver displays 303 the data and prints 305 a new blank form 267 and an updated health view 323, and provides the updated device 265 from the computer. The new blank form 267, the updated health view 323 and the updated device 265 provide the updated package 329, which is ready to be given to a caregiver on the owner's next encounter with a caregiver.

Figure 49:
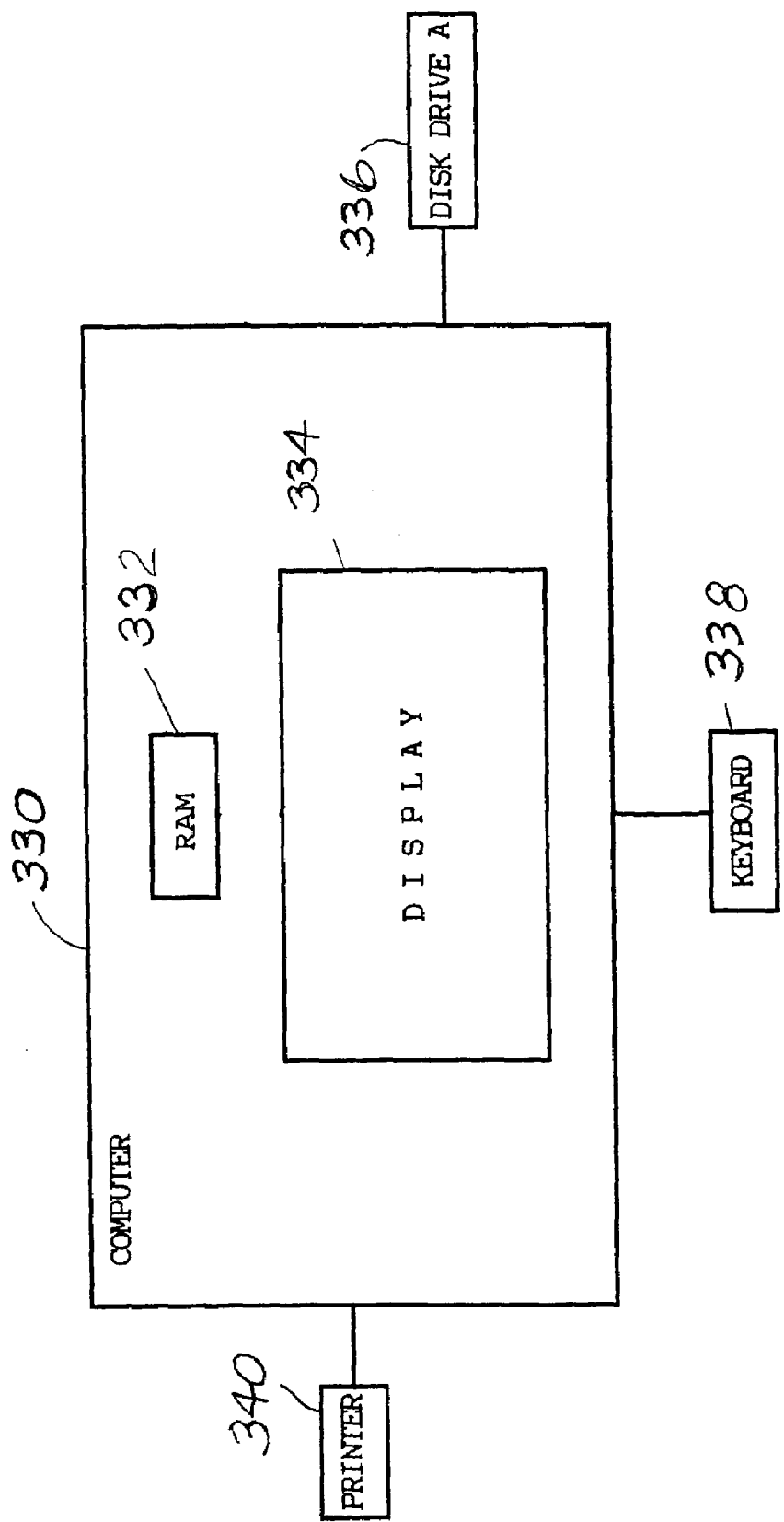
FIG. 49 is a schematic representation of the new system.
Figure 50:
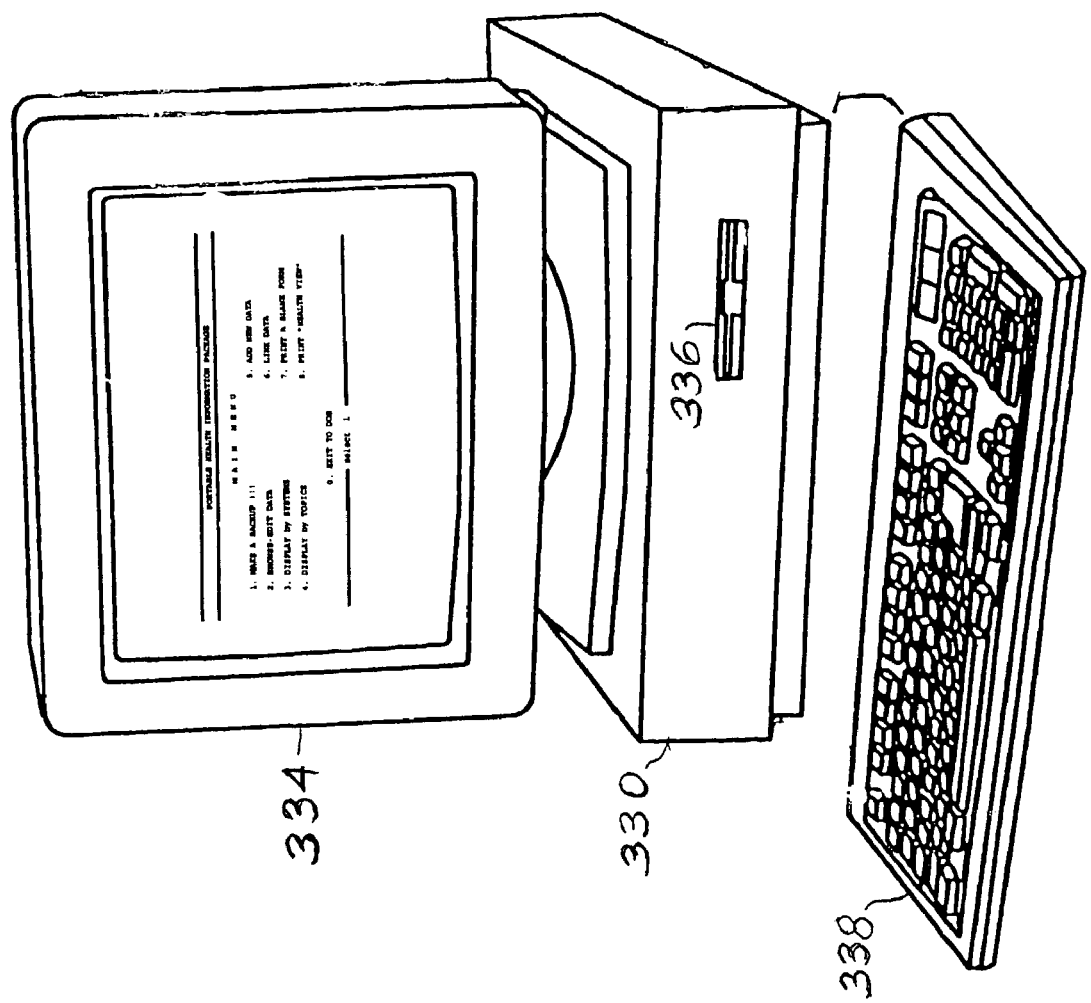
FIG. 50 is a schematic representation of a computer using the new invention.

Referring to FIGS. 49 and 50, a computer 330 has a random access memory (RAM) 332 and a display 334. A disc drive 336 accepts a portable computer readable and writeable device. A keyboard 338 connected to the computer 330 controls selection of screens and input of data. Once the device has been placed in the drive 336, the keyboard operator keys the number "1" and "Enter". The system automatically starts and displays the main menu screen shown in FIG. 1. A printer 340 is connected to the computer and prints out blank forms and health views upon selection by the computer operator's keystrokes on the keyboard 338.

Figure 51:
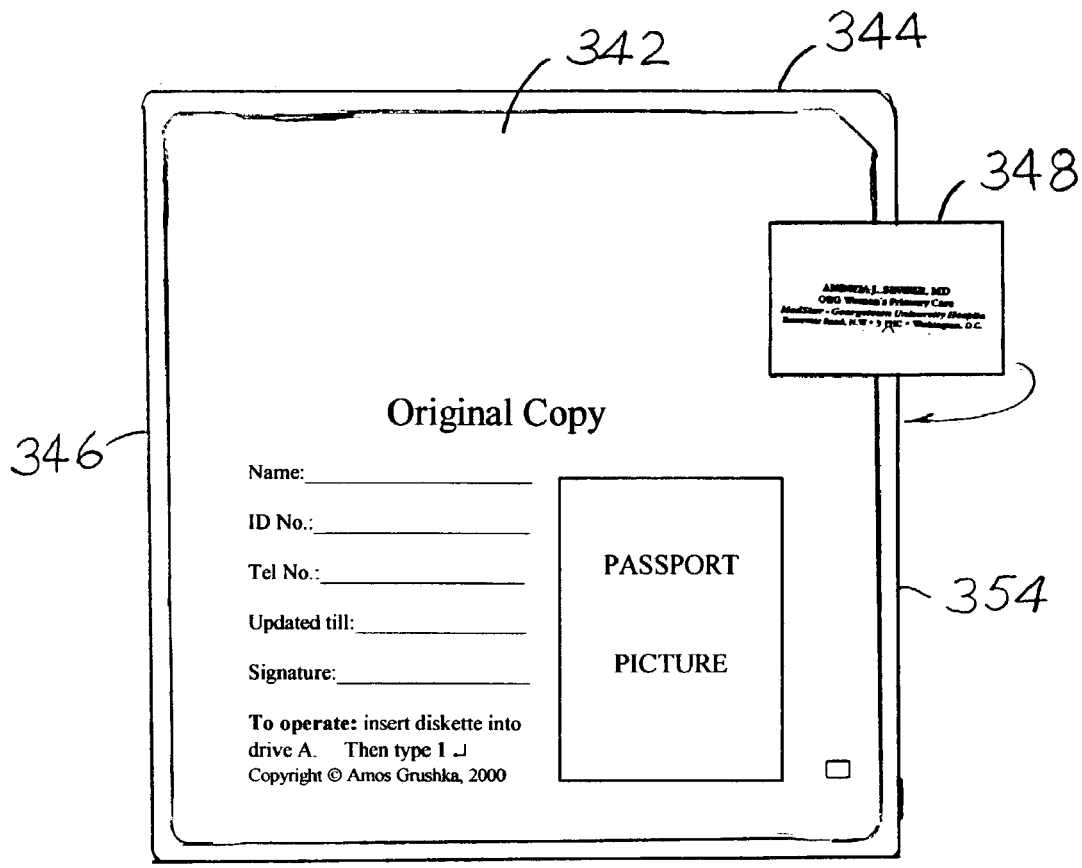
FIG. 51 shows a computer readable device in a case with a seal.

FIG. 51 shows a computer readable and writeable device 342, which is contained in a transparent case 344 with a living hinge along one side 346. Before a caregiver returns the updated computer readable and writeable device 342 to the owner, the device is placed in the case, and the case is closed and sealed. One form of sealing is shown in which a label 348 with the caregiver's identification is wrapped around the openable edges 354 of the case 344. The label 348 is permanently adhered to opposite sides of the case near the openable edges 354. The owner carries the device 342 in the sealed case 344. The device 342, in the closed and sealed case is given to the next healthcare provider. The condition of the seal indicates whether the case has been opened.

Figure 52:
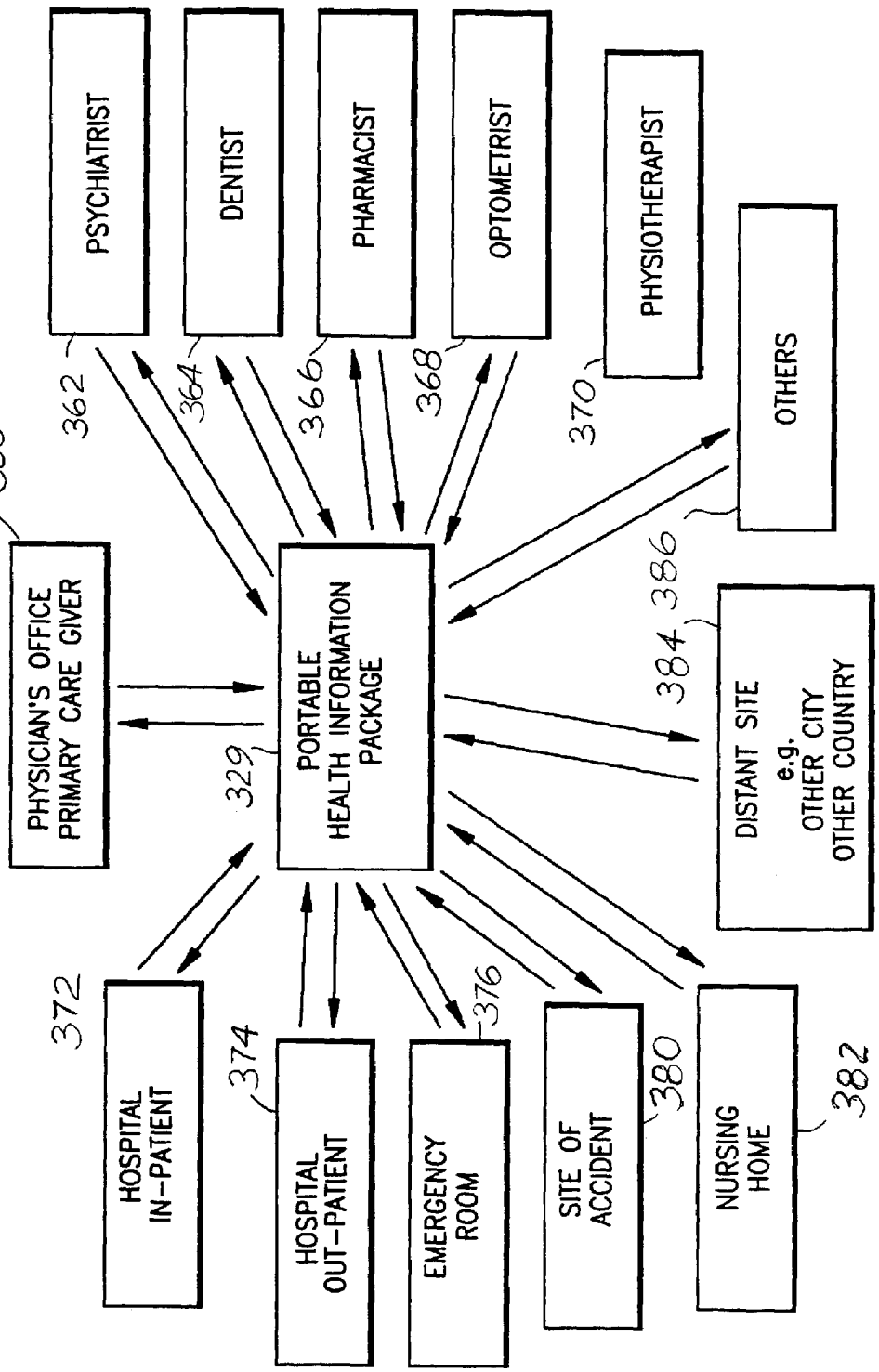
FIG. 52 is a schematic representation of use and input of information in the portable health information package by medical care professionals.

Referring to FIG. 52, the portable health information package 329 may be handed back and forth from the owner to the primary care giver physician's office 360, to a psychiatrist 362, a dentist 364, a pharmacist 366, optometrist 368, physiotherapist 370, a hospital facility for inpatients 372 or outpatients 374, or an emergency room 376. The package 329 may be used at the site of an accident 380, in a nursing home 382, at a distant site 384 in another city or country, or by other caregivers 386.

In the preferred embodiment, each data element is recorded as one structured free text record in the personal database file, which when printed can fit one horizontal line in a standard 8½×11" or A4 size page. As shown in FIG. 41, each record comprises ten character-type fields 203, which are used to record data elements. Each field has a predefined length. The data are recorded in all fields as characters, even in fields that contain date data. A label of a body system is recorded in the SYS field by three characters. The number of the problem in a body system is recorded in the NO field with up to two characters. The type of data is recorded in the T field, using one character. The data are recorded in the DATA field with up to thirty-four characters. Details of data are recorded in the DETAILS field using up to seventeen characters. The sequence of topics in a problem is recorded in the SQ field by up to two characters. The subject of the data is recorded in the SUB field by up to three characters. The date of the occurrence of each data element is recorded in the DATE field by up to ten characters. The time of the occurrence of each data element is recorded in the TIME field by up to eleven characters. The source of each data element is recorded in the SOURCE field by up to fifteen characters. Thus, each data element is recorded as one record in the personal database by up to ninety-nine characters, as shown in screen 201 of FIG. 41.

Although one can use any characters to label body systems, in the preferred embodiment, it is recommended, as shown in screen 69 of FIG. 15, to use the following character combinations 71 to label body systems in the system (SYS) field: CVS=cardiovascular system; DEN=dental system; END=endocrine system; ENT=ear, nose and throat systems; EYE=eye (ophthalmic) system; GIT=gastrointestinal system; GUR=genitourinary system; GYN=gynecologic system; HEB=hepato-biliary system; HEM=hematologic system; MET=metabolic and nutritional conditions; MUS=musculoskeletal system; NEU=neurologic system;

PSY=psychiatric conditions; RES=respiratory system; SKN=skin (dermatologic) system; SYS=systemic conditions; ALL=all body systems. Using the recommended character combinations when recording data elements enables instant clustering of data elements by body system in the database file, and also displaying data by systems by selecting the appropriate number 1-18 in screen 69 of FIG. 15. For instance, FIG. 16 shows screen 73, which displays only data related to the musculoskeletal system because the caregiver has selected option 13, ("13.MUS"), in screen 69 of FIG. 15. FIG. 17 shows screen 77, which displays only data related to the skin (dermatologic) system because the caregiver has selected option 17, ("17.SKN"), in screen 69 of FIG. 15.

If a data element cannot be classified and its cause is unknown, it is recommended to label the body system (SYS) of the data element with three question marks (???). This ensures that unexplained data will be instantly displayed clearly at the top of the browse screen 23 as shown in FIG. 3 and at the top of the health view printout as shown in FIG. 43a, and thus draw the caregivers attention immediately. All data elements labeled with three question marks (???) are displayed clearly at the top of the screens in FIGS. 3-5, 7-10, 12-13, 20, 21, 25, 29, 43 and 43a.

In the preferred embodiment of the present invention, personal identification data of the owner can be added to the components of the package in four simple methods. The name, ID number, telephone number, signature of the owner and the date in which the data were last updated can be hand written on the preprinted paper label already affixed to the surface of the portable computer readable device, shown in FIG. 46. A passport picture of the owner can be glued on the preprinted paper label already affixed to the surface of the portable computer readable device, shown in FIG. 46. A short personal identification label of the owner, such as his name, his ID number or a telephone number can be recorded electronically on the portable computer readable device, by selecting option 1, ("1.MAKE A BACKUP"), as shown in screen 13 of FIG. 1, and then answering questions 18 and 20, and then following instructions 19 in screen 17 of FIG. 2. The name, address and date of birth of the owner can be recorded electronically as a record in the portable personal database file, by selecting option 5, ("5.ADD NEW DATA"), in screen 13 of FIG. 1, and then recording the name in the data field leaving the system field (SYS) blank. This ensures that the name, address and date of birth of the owner will be displayed clearly as the first line of the browse screen as shown in FIG. 3 and at the top of the HEALTH VIEW printout as shown in FIG. 43a, and thus draw the caregivers attention immediately. One or all of the personal identification data can be changed or removed completely on any one of the components of the package, whenever the owner wants, using the same simple methods within seconds anywhere, and thus enables him to maintain anonymity.

Although one can use any characters to label types of data, in the preferred embodiment, it is recommended, to use the following characters to label types of data: F=family history; S=signs and symptoms; L=laboratory examinations and tests; D=diagnoses; T=all treatments. Although one can use any other characters to label subjects, in the preferred embodiment, it is recommended, to use the following characters combinations to label the most common subjects: BLD=blood; TAB=tablet. Using the recommended characters when recording data elements enables instant clustering of data elements by types of data and subjects in the database file, and also displaying data by selecting the appropriate numbers in screen 81 of FIG. 18. For instance, FIG. 19 shows screen 83, which displays only family history data 84 because the caregiver has selected option 1, ("1.FAMILY HISTORY"), in screen 81 of FIG. 18. FIG. 20 shows screen 85, which displays only signs and symptoms data 86 because the caregiver has selected option 2 ("2.SIGNS & SYMPTOMS") in screen 81 of FIG. 18.

Although in the preferred embodiment of the present invention it is possible to record on one portable computer readable storage device more than eight thousand data elements, which is in most cases more than necessary for all the health data of the owner from birth to death with no exception, it is recommended to record only abnormal and normal relevant health data elements. Recording only abnormal and normal relevant health data elements has significant advantages. It reduces the work needed to enter data, and enables every caregiver to view and/or print an overview of the complete medical history of a patient, or only the relevant data that he needs to perform his task, usually with one click of a button, in a clear, concise layout, which can support his diagnostic and management decisions.

The invention provides a simple, standard, fast, accurate and very easy uniform method for recording each and every health data element with no exception, using structured professional free text, in computer readable and in eye readable forms by all caregivers, at all points of care anywhere in the world.

Each and every health data element of the owner, with no exception, is recorded quickly in one simple standard form by all caregivers at all points of care, anywhere in the world, with no exception. Every caregiver records all findings, tests, diagnoses, therapies and any other health data, in his own natural professional language, at all points of care, anywhere in the world. Caregivers record all complaints of the owner and any other information provided by him, in the owner's own words, at all points of care, anywhere in the world. Every caregiver records exact time, as well as temporal uncertainty and multiple temporal granularities, for each and every data element, even if it cannot fit into any standard "valid" date field.

It is usable with any existing personal computer, even computers that have very slow processors and do not have a hard disk.

Backup of all or any one of the components of the package can be easily done within seconds anywhere.

In the preferred embodiment, the portable device is inserted into the reader/writer. The presentation of the health data elements is organized according to the body organ systems for presenting the health data elements further grouped by topic and sequenced according to the labeling designations. The presentation displays the health data elements according to any other labeling designations of the data elements in any of the fields. The health data elements are displayed and printed according to the labeling designations, by body systems, problem number, topics and sequence of the topics.

Health data elements are recorded to the health data file, including attributes of health information data in fields in the health data elements. Health data elements and the fields of health information in the health data file are recorded in a standard universal structure, which stores identifications of fields and body organ system designations in the portable health data file in the portable device.

In the preferred embodiment, in order to link and integrate data from two portable computer readable devices, the recorded health data elements are temporarily transferred from one portable device into the hard disk of a personal computer. The second portable device is inserted into the appropriate reader/writer, and the health data elements are transferred from the hard disk to the second portable device. A search of the health data elements is performed in the health data file for specific attributes in the health data fields of the health data file.

The need to link and integrate data from two devices occurs when one part of the health information of the owner is stored on one device and another part of his health information is stored on another device. This happens when the owner does not have with him the old device at the point of care, and his caregiver records new data on a new temporary device.

In one embodiment, application files are included in the portable device. Displaying the applications files includes display screens on the display screen of the computer for selecting organizations and presentations of the data elements according to specific attributes and fields. The applications files also provide organizing and presenting the health data elements by body organ system, problem number, topic, sequence and subject.

In one embodiment, the display has attributes of health information in fields in the health data elements and includes the health information data in fields of body organ system, problem number, topic data, details data, sequence of topic presentation, subject data, date data and time data.

In one embodiment, the portable device is inserted into an appropriate reader/writer and may print out a form from the portable device for a user to use for recording data elements.

In another embodiment, the device is inserted in an appropriate reader/writer. This enables application software from the portable device to control the data processing system, the application files and the health data files in the portable device by commands to a random access memory connected to the reader/writer.

In another embodiment, the portable device is inserted in an appropriate reader/writer, temporarily transferring the data processing system. The application files and the health data files may be transferred from the portable device. The portable device is removed from the reader/writer. A second portable device is inserted in the reader/writer for transferring the data from the random access memory to the second portable device.

In one embodiment, the present invention includes displaying each health data element as one line on a display screen. The health data elements are stored and organized, including organizing the health data elements into groups according to body organ system designation when the displaying of the health data elements occurs.

In one embodiment, each health data element may be printed as one line on a printout. The health data elements may also be stored and organized, including organizing the health data elements into groups according to at least one of the body organ system designations when the printing of the health data elements occurs.

In another embodiment, the present invention is a personal health data package apparatus including a programmable detachable portable computer readable and writable device, a data processing system in the portable device, a health data file in the portable device, health data elements recorded in the health data file, the health data elements, further comprising attributes of health information data in fields in the health data elements, the health data elements and the fields of health information being stored in the health data file, identifications of fields stored in the portable device, and body organ system designations stored in the portable device.

In this embodiment, the recorded health data elements include recordings of abnormal and normal relevant health data elements. The portable device is inserted into the appropriate reader/writer. The health data elements are organized according to the body organ systems for presenting the health data elements according to the body organ systems.

Another embodiment utilizes a display for displaying the health data elements according to body organ systems, a printer for printing the health data elements according to body organ systems, and a hard disc for temporarily transferring the recorded health data elements from the portable device into the hard disc. A second portable device may be inserted in the reader/writer, for transferring the health data elements from the hard disc to the second portable device.

One embodiment includes an application file in the portable device having search commands for searching the health data elements in the health data file for specific attributes in specific fields in the health data file. The present invention also includes applications files in the portable device.

The applications files include display screens for selecting organizations and presentations of the health data elements according to specific attributes and fields.

In one embodiment, the health data elements are stored in the portable device and are organized when presented by body organ system, problem number, topic, sequence and subject.

In another embodiment, the attributes of the health information are stored as data in the fields and the health data elements in fields of body organ system, problem number, topic data, details data, sequence, date data and time data. Information is stored in the portable device for printing out a form for a user to use for recording data elements.

In one embodiment, the portable device inserted in a reader/writer enables application software to control the data processing system, the application files and the health data files in the portable device with commands to a random access memory connected to a drive.

In one embodiment, portable device is inserted in a reader/writer for temporarily transferring the data processing system, the application files and the health data files in the portable device to the random access memory before removing the portable device from the reader/writer. A second portable device inserted in the drive for transferring the data from the random access memory to the second portable device.

While the preferred embodiment of the invention is recording, storing, organizing, displaying and printing health data of human beings, alternative embodiments include variations of the invention for storage and retrieval of other types of data, such as health data of animals, and a variety of personal data of humans and animals or groups of animals. The cost of manufacturing a complete package, in which the computer readable storage device is a 3.5-inch floppy disk, is minimal.

In the preferred embodiment, the portable personal health information package uses standard 3.5-inch floppy disks as a portable computer readable storage device, and standard 3.5 disk drives of any personal computer as reader/writers, for storage of the complete database management software program and the owner's personal health data file, ready for use with any standard personal computer.

The present invention further includes a data processing system in the portable device, a health data file in the portable device. The present invention records health data elements to the health data file, including attributes of health information data in fields in the health data elements, stores health data elements and the fields of health information in the health data file, all in one in a standard universal structure, stores identifications of fields in the portable device and stores Body organ system designations in the portable health data file in the portable device.

The present invention records abnormal and normal relevant health data elements. The portable device may also be inserted into reader/writer. The presentation of the health data elements can be organized according to the body organ systems for presenting the health data elements further grouped by topic and sequence according to the labeling designations. The presentation may also display the health data elements according to any other labeling designations of the data elements in any of the fields. The user may print the health data elements according to the labeling designations, by body systems, problem number, topic and sequence of the topics.

In the present invention, the recorded health data elements may be temporarily transferred from the portable device into a hard disc of a personal computer. A second portable device may be inserted into the appropriate reader/writer, and the health data elements may be transferred from the hard disc to the second portable device.

The present invention allows for a search of the health data elements to be performed in the health data file for specific attributes in the health data fields of the health data file.

Application files may be included in the portable device. Displaying the applications files may include display screens on the display screen of the computer for selecting organizations and presentations of the data elements according to specific attributes and fields. Providing the applications files may also provide organizing and presenting the health data elements by body organ system, problem number, topic, sequence and subject.

The display has attributes of health information in fields in the health data elements and includes the health information data in fields of body organ system, problem number, topic data, details data, sequence of topic presentation, subject data, date data and time data.

The portable device may be inserted into an appropriate reader/writer and may print out a form from the portable device for a user to use for recording data elements.

The portable device may further be inserted in an appropriate reader/writer. This enables application software from the portable device to control the data processing system, the application files and the health data files in the portable device by commands to a random access memory connected to the reader/writer.

The portable device may also be inserted in an appropriate reader/writer and temporarily transferring the data processing system. The application files and the health data files may be inserted in the portable device. The portable device may be removed from the reader/writer. A second portable device may be inserted in the reader/writer for transferring the data from the random access memory to the second portable device.

The present invention includes displaying each health data element as one line on a display screen. The health data elements are stored and organized, including organizing the health data elements into groups according to at least one body organ system designation when the displaying of the health data elements occurs.

Each health data element may be printed as one line on a printout.

The health data elements may also be stored and organized, including organizing the health data elements into groups according to at least one of the body organ system designations when the printing of the health data elements occurs.

The present invention is a personal health data package apparatus including a programmable detachable portable computer readable and writable device, a data processing system in the portable device, a health data file in the portable device, health data elements recorded in the health data file, the health data elements, further comprising attributes of health information data in fields in the health data elements, the health data elements and the fields of health information being stored in the health data file, identifications of fields being stored in the portable device, and body organ system designations being stored in the portable device.

The recorded health data elements include recordings of abnormal and normal relevant health data elements.

The portable device is inserted into the appropriate reader/writer. The health data elements are organized according to the body organ systems for presenting the health data elements according to the body organ systems.

The present invention includes a display for displaying the health data elements according to body organ systems, a printer for printing the health data elements according to body organ systems, and a hard disc for temporarily transferring the recorded health data elements from the portable device into the hard disc. A second portable device may be inserted in the reader/writer, for transferring the health data elements from the hard disc to the second portable device.

The present invention also includes an application file in the portable device having search commands for searching the health data elements in the health data file for specific attributes in specific fields in the health data file. The present invention also includes applications files in the portable device.

The applications files include display screens for selecting organizations and presentations of the health data elements according to specific attributes and fields.

In the present invention, the health data elements are stored in the portable device and are organized when presented by body organ system, problem number, topic, sequence and subject.

In the present invention, the attributes of the health information data in the fields and the health data elements in fields of body organ system, problem number, topic data, details data, sequence, date data and time data. Information is stored in the portable device for printing out a form for a user to use for recording data elements.

The present invention includes a portable device in a reader/writer enabling application software for controlling the data processing system, the application files and the health data files in the portable device with commands to a random access memory connected to a drive.

The present invention includes inserting a portable device in a reader/writer for temporarily transferring the data processing system, the application files and the health data files in the portable device to the random access memory before removing the portable device from the reader/writer, and a second portable device inserted in the drive for transferring the data from the random access memory to the second portable device.

The new system enables a computer to record, link and integrate health data of a memory device of an individual from birth to death, collected from all paper-based medical records, computer-based medical records, and all other sources of information.

The new system enables a person to carry with him at all times his complete health information, and allows him to grant his caregivers instant access to all or any part of his health data, whenever the information is needed at all points of care, anywhere in the world with no exception.

The new memory device placed in a computer can print an updated structured summary of the owner's health history from birth to death, which displays his health data, organized by body organ systems and types and subtypes of data that is instantaneously eye-readable.

The new system enables every caregiver to view and/or print only the relevant data that he needs to perform his task, usually with one click of the button, in a clear, concise layout, which can support diagnostic and health management decisions.

The new method and apparatus enables a patient to view all his own health information, correct inaccurate data, add missing data, gain understanding of his own health, and have absolute control over the privacy, confidentiality, security, backups and access to his personal health data.

The package works fast even with very old computers that have slow processors, and do not have a hard disk, because the database management software program and a personal database file are contained in a portable computer readable storage device, and the database management software program is resident on the portable computer readable storage device during its operation, and uses only the RAM of a PC.

The new system uses a variety of portable programmable detachable computer readable/writable memory devices to store and carry the personal database file and the database management software program. The devices include, without limitation, optical memory cards, floppy disks, flash memory cards, PCMCIA cards and other computer readable storage devices with comparable storage capacity.

Other Embodiments of the Invention

While the preferred embodiment of the invention is recording, storing, organizing, displaying and printing health data of human beings, alternative embodiments include variations of the invention for storage and retrieval of other types of data, such as health data of animals, machine maintenance data, and a variety of personal data such as, curriculum vitae, addresses and telephone numbers, birthdays, anniversaries etc.

While the preferred embodiment of the invention uses a conventional 3.5 inch floppy disk as a portable computer readable storage device, the invention can use a variety of other portable programmable detachable computer readable devices, to store and carry the personal database file and the database management software program, including optical memory cards, flash memory cards, PCMCIA cards and other computer readable storage devices with comparable storage capacity.

The invention is independent of any specific hardware or software. If in the future any other new types of personal computer, portable programmable detachable computer readable/writable device, or software language will gain wide acceptance, then it will be possible to use them worldwide, as parts of the present invention.

CONCLUSIONS, RAMIFICATIONS, AND SCOPE OF THE INVENTION

The reader will see that the portable personal health information package of the present invention can overcome today anywhere in the world, many very common universal problems, that prevent caregivers form getting all the relevant data from the past health history of patients at all points of care, which innumerable commercial bodies, academic institutes, national and international organizations and countless individuals, tried to solve and failed.

The invention has the potential to greatly improve communication among caregivers, alter dramatically how patient healthcare information will be accessed, transmitted and used, and improve the way information is shared within the medical community. The invention can improve the quality and reduce the cost of healthcare given to the owner of the package, anywhere in the world. There are no technical, financial or legal barriers that can prevent immediate widespread use of the package anywhere in the world. Therefore, it is possible to begin to use the system immediately, anywhere in the world with no exception—in poor countries and in rich countries alike, and the vision that many millions of people would carry their personal health information package can be realized. Widespread use of the invention can have a dramatic positive effect upon public health and cost containment, and will be highly beneficial to for patients, caregivers, insurers and society at large, worldwide.

While the above description contains many specificities, these should not be construed as limitations on the scope of the invention, but rather as exemplifications of the preferred embodiments thereof. Many other variations are possible. Accordingly, the scope of the invention should be determined not by the embodiments illustrated, but by reference to the accompanying claims and their legal equivalents.

I claim:

1. A method for handling personal health data, comprising:
providing a personal detachable portable computer readable and writeable memory device;
providing applications software self contained in the portable device, the applications software including functions of recording the data, organizing the data according to body organ systems, browsing, displaying, printing and editing wherein the device does not require external software except a disc operating system and wherein the portable device uploads the self-contained software which is used to record the data, organize the data according to body organ systems, browse, display, print and edit the personal health data;
providing a health data file in the portable device;
recording health data elements in the health data file;
providing attributes of health information data in fields of health information in the health data elements;
storing the health data elements in the fields of health information as records in the health data file in a standard universal structure;
storing identifications of the fields of health information in the portable device; and
storing body organ system designations in the health data file in the portable device.

2. The method of claim 1, wherein the recording comprises recording abnormal and normal relevant health data elements.

3. The method of claim 1, further comprising connecting the portable device to a personal computer and presenting the health data elements.

4. The method of claim 3, the self contained applications software functions further comprising organizing presentation of the health data elements according to the body organ systems for presenting the health data elements further grouped by topic and sequence according to labeling designations.

5. The method of claim 3, wherein the presenting further comprises the displaying of the health data elements according to other labeling designations of the data elements in any of the fields.

6. The method of claim 3, wherein the presenting further comprises the printing of the health data elements according to the labeling designations, by body systems, problem number, topic and sequence of the topics.

7. The method of claim 3, further comprising:
temporarily transferring the recorded health data elements from the portable device into a hard disc of a personal computer;

connecting a second portable device to the personal computer; and transferring the health data elements from the hard disc to the second portable device.

8. The method of claim 3, wherein the self contained software further includes functions of performing a search of the health data elements in the health data file for specific attributes in the health data fields of the health data file.

9. The method of claim 1, wherein the providing of applications software further comprises providing display screens on a display of a personal computer for selecting organizations and presentations of the data elements labeled by specific attributes in the fields.

10. The method of claim 1, the applications software further comprising organizing and presenting the health data elements by body organ system, problem number, topic, sequence and subject.

11. The method of claim 1, wherein the providing of attributes of health information in fields in the health data elements comprises providing the health information data in fields of body organ system, problem number, topic, data, details, sequence of topic presentation, subject, date, time and source.

12. The method of claim 1, further comprising connecting the portable device to a personal computer, printing out a form from the portable device for a user and using the form for recording data elements.

13. The method of claim 1, further comprising connecting the portable device to a personal computer and enabling the applications software from the portable device to control the applications software and the health data file in the portable device by commands to a random access memory of the personal computer.

14. The method of claim 1, further comprising connecting the portable device to a personal computer and temporarily copying the health data file in the portable device to a hard disc of the personal computer, removing the portable device from the personal computer, connecting a second portable device to the personal computer and transferring the data from the hard drive to the second portable device.

15. The method of claim 1, further comprising displaying each health data element as one line on a standard display screen.

16. The method of claim 15, further comprising organizing the health data elements into groups according to at least one of the body organ system designations when the printing of the health data elements occurs.

17. The method of claim 15, further comprising storing the health data elements and organizing the health data elements into groups according to at least one body organ system designation when the displaying of the health data elements occurs.

18. The method of claim 1, further comprising printing each health data element as one line on a standard paper printout.

19. The method of claim 1 further comprising:
providing a package containing the memory device,
providing an instruction for using the device in the package,
providing a health data view printed record in the package, and
providing a printed written data recording form in the package.

20. Personal health data package apparatus, comprising:
a portable, detachable computer readable and writable device;
applications software self contained in the portable device, the applications software including functions of recording the data, organizing the data according to body organ systems, browsing, displaying, printing and editing wherein the device does not require external software except a disc operating system and wherein the portable device uploads the self-contained software which is used to record the data, organize the data according to body organ systems, browse, display, print and edit the personal health data;
a health data file in the portable device;
health data elements recorded in the health data file:
the health data elements further comprising attributes of health information data in fields in the health data elements;
the health data elements and the fields of health information being stored in the health data file;
identifications of fields stored in the portable device; and
body organ system designations stored in the portable device.

21. The apparatus of claim 20, wherein the recorded health data elements comprise recorded abnormal and normal relevant health data elements.

22. The apparatus of claim 20, wherein the portable, detachable computer readable and writable device is connected to a personal computer.

23. The apparatus of claim 22, wherein a display of the personal computer displays the health data elements according to body organ systems on the screen display of the personal computer.

24. The apparatus of claim 22, further comprising a printer connected to the personal computer for printing the health data elements according to body organ systems on the display of the personal computer.

25. The apparatus of claim 22, further comprising a hard disc in the personal computer for temporarily storing the recorded health data elements from the portable device into the hard disc of the personal computer, a second portable device connected to the personal computer, the health data elements being transferred from the hard disc to the second portable device.

26. The apparatus of claim 22, further comprising the applications software in the portable device having search commands for searching the health data elements in the health data file for specific attributes in specific fields in the health data file.

27. The apparatus of claim 20, wherein the applications software further comprise display screens for selecting organizations and presentations of the health data elements according to specific attributes and fields.

28. The apparatus of claim 20, wherein the health data elements are stored in the portable device and are organized by the applications software in the portable device when presented by body organ system, problem number, topic, sequence and subject.

29. The apparatus of claim 20, wherein the attributes of the health data elements are grouped according to body organ system, problem number, topic, data, details, sequence, date, time and source.

30. The apparatus of claim 20, wherein the applications software stored in the portable device includes functions for printing out a form for a user to use for recording data elements.

31. The apparatus of claim 20 further comprising:
a package containing the memory device,
an instruction for using the device in the package,
a health data view printed record in the package, and
a printed written data recording form in the package.

32. Personal health data package apparatus, comprising:
a portable, detachable personal computer readable and writable device;
applications software self contained in the portable device, the applications software including functions of browsing, displaying, printing and editing wherein the device does not require external software except a disc operating system and wherein the portable device uploads the software which is used to browse, display, print and edit the personal health data;
a health data file in the portable device;
health data elements recorded in the health data file;
the health data elements further comprising attributes of health information data in fields in the health data elements;
the health data elements and the fields of health information being stored in the health data file;
identifications of fields stored in the portable device; and
body organ system designations stored in the portable device,
further comprising a personal computer for receiving the portable device,
wherein the health data elements are organized in the personal computer by the applications software self contained in the portable device according to the body organ systems for presenting the health data elements according to the body organ systems.

33. The apparatus of claim 32 further comprising:
a package containing the memory device,
an instruction for using the device in the package,
a health data view printed record in the package, and
a printed written data recording form in the package.

34. A method for handling personal health data, comprising:
providing a personal portable memory device;
providing a health data file in the portable memory device;
providing applications software self contained in the portable memory device;
the applications software including functions of recording the data, organizing the data according to body organ systems, browsing, displaying, printing and editing wherein the device does not require external software except a disc operating system and wherein the portable device uploads the self-contained software which is used to record the data, organize the data according to body organ systems, browse, display, print and edit the personal health data;
recording health data elements in the health data file;
providing attributes of health information data in fields of health information in the health data elements;
storing the health data elements in the fields of health information as records in the health data file;
storing identifications of the fields of health information; and
storing body organ system designations in the health data file.

35. The method of claim 34, wherein the recording comprises recording abnormal and normal relevant health data elements.

36. The method of claim 34, wherein the storing comprises storing in the portable device and further comprising connecting the portable device to a personal computer and presenting the health data elements in a display of the personal computer and controlled by the applications software in the portable device.

37. The method of claim 34, further comprising the applications software stored in the portable device having functions for organizing presentation of the health data elements according to the body organ systems for presenting the health data elements further grouped by topic and sequence according to labeling designations.

38. The method of claim 34, wherein the applications software stored in the portable device has functions for displaying the health data elements according to other labeling designations of the data elements in any of the fields.

39. The method of claim 34, wherein the applications software stored in the portable device has functions for printing the health data elements according to the labeling designations, by body systems, problem number, topic and sequence of the topics.

40. The method of claim 34, further comprising:
temporarily transferring the recorded health data elements from a first portable device into a hard disc of a personal computer;
connecting a second portable device to the personal computer; and
transferring the health data elements from the hard disc to the second portable device.

41. The method of claim 34, further comprising the applications software stored in the portable device having functions for performing a search of the health data elements in the health data file for specific attributes in the health data fields of the health data file.

42. The method of claim 34, wherein the applications software stored in the portable device has functions for providing display screens on a display of a personal computer for selecting organizations and presentations of the data elements labeled by specific attributes in the fields.

43. The method of claim 34, further comprising the applications software stored in the portable device having functions for organizing and presenting the health data elements by body organ system, problem number, topic, sequence and subject.

44. The method of claim 34, wherein the applications software stored in the portable device has functions for providing of attributes of health information in fields in the health data elements comprises providing the health information data in fields of body organ system, problem number, topic, data, details, sequence of topic presentation, subject, date, time and source.

45. The method of claim 34, further comprising connecting the portable memory device file in personal computer, printing out a form from the health data file for a user and using the form for recording data elements.

46. The method of claim 34, further comprising connecting the portable device with the health data file and the applications software in an appropriate personal computer and enabling the applications software for controlling the applications software and the health data file by commands to a random access memory of the personal computer.

47. The method of claim 34, wherein the portable device is a first portable device, connecting the first portable device to a personal computer and temporarily accessing the applications software and the health data file in the first portable device as data by a random access memory and a hard disc, removing the first portable device from the personal computer, connecting a second portable device to the personal computer and transferring, linking and integrating the data from the hard disc via the random access memory to the second portable device.

48. The method of claim 34, further comprising displaying each health data element as one line on a standard display screen.

49. The method of claim 48, further comprising storing the health data elements and organizing the health data elements into groups according to at least one body organ system designation when the displaying of the health data elements occurs.

50. The method of claim 34, further comprising printing each health data element as one line on a standard paper printout.

51. The method of claim 34 further comprising:
providing a package containing the memory device,
providing an instruction for using the device in the package,
providing a health data view printed record in the package, and
providing a printed written data recording form in the package.

52. A method for handling personal health data, comprising:
providing a personal portable memory device;
providing a health data file in the portable memory device;
providing applications software self contained in the portable memory device;
the applications software including functions of browsing, displaying, printing and editing wherein the device does not require external software except a disc operating system and wherein the portable device uploads the software which is used to browse, display, print and edit the personal health data;
recording health data elements in the health data file;
providing attributes of health information data in fields of health information in the health data elements;
storing the health data elements in the fields of health information as records in the health data file;
storing identifications of the fields of health information; and
storing body organ system designations in the health data file,
further comprising displaying each health data element as one line on a display screen,
further comprising the applications software stored in the portable device having functions for organizing the health data elements into groups according to at least one of the body organ system designations when the printing of the health data elements occurs.

53. The method of claim 52 further comprising:
providing a package containing the memory device,
providing an instruction for using the device in the package,
providing a health data view printed record in the package, and
providing a printed written data recording form in the package.

54. Personal health data package apparatus, comprising:
a portable memory device;
applications software self contained in the portable memory device, the applications software including functions of recording health data, organizing the data according to body organ systems browsing, displaying, printing and editing wherein the device does not require external software except a disc operating system and wherein the portable device uploads the self-contained software which is used to record the data, organize the data according to body organ systems, browse, display, print and edit the personal health data;
a health data file stored in the portable device;
health data elements recorded in the health data file;
the health data elements further comprising attributes of health information data in fields in the health data elements;
the health data elements and the fields of health information being stored in the health data file;
identifications of fields stored in the portable device;
body organ system designations stored in the portable device; and
operating software stored in the portable device.

55. The apparatus of claim 54, wherein the recorded health data elements comprise recorded abnormal and normal relevant health data elements.

56. The apparatus of claim 54, wherein the portable memory device is connected to a personal computer for receiving the health data file from the personal portable memory device.

57. The apparatus of claim 56, further comprising a printer connected to the personal computer for printing the health data elements according to body organ systems.

58. The apparatus of claim 56, wherein the portable device is a first portable device and is connected to the personal computer, further comprising a hard disc for temporarily transferring the recorded health data elements from the first portable device into the hard disc under control of the self contained applications software, a second portable device connected to the personal computer, the health data elements being transferred linked and integrated from the hard disc to the second portable device under control of the self contained applications software.

59. The apparatus of claim 56, wherein the health data elements are organized according to the body organ systems by the applications software stored in the portable device for presenting the health data elements according to the body organ systems.

60. The apparatus of claim 54, wherein the applications software further comprise functions for presenting display screens and for selecting organizations and presentations of the health data elements according to specific attributes and fields.

61. The apparatus of claim 54, wherein the health data elements are stored in the portable device and are organized when presented by a personal computer controlled by the stored applications software into body organ system, problem number, topic, sequence and subject.

62. The apparatus of claim 54, wherein the attributes of the health information data in the fields have indications and the health data elements in fields of body organ system, problem number, topic, data, details, sequence, date, time and source.

63. The apparatus of claim 54, further comprising the applications software stored in the portable device having functions for printing out a form for a user to use for recording data elements.

64. The apparatus of claim 54 further comprising:
a package containing the memory device,
an instruction for using the device in the package,
a health data view printed record in the package, and
a printed written data recording form in the package.

65. A method for handling personal health data, comprising:
providing a personal detachable portable computer readable and writeable memory device;
providing applications software self contained in the portable device, the applications software including functions of recording the data, organizing the data according to body organ systems, browsing, displaying, printing and editing wherein the device does not require external software except a disc operating system and wherein the portable device uploads the self-contained software which is used to record the data, organize the data according to body organ systems, browse, display, print and edit the personal health data;

providing a health data file in the portable device;

recording health data elements in the health data file;

providing attributes of health information data in fields of health information in the health data elements;

storing the health data elements in the fields of health information as records in the health data file in a standard universal structure;

storing identifications of the fields of health information in the portable device;

storing body organ system designations in the health data file in the portable device; and providing a package containing the personal portable memory device, a printed health view and a data recording form for enabling a new health data element in a standard structure.

66. The method of claim 65, wherein the standard structure of the data recording form has limited spaces for writing entries of system, number, data, details, date and time.

67. The method of claim 66, wherein the health data elements within the portable device have standard structure of the fields of health information in the health data elements.

68. The method of claim 67, wherein each of the data health elements is structurally limited to a number of characters that fit in one line on the printed health view.

69. The method of claim 65 further comprising:

providing a package containing the memory device, providing an instruction for using the device in the package, providing a health data view printed record in the package, and providing a printed written data recording form in the package.

* * * * *